US008247419B2

(12) United States Patent
Lee et al.

(10) Patent No.: US 8,247,419 B2
(45) Date of Patent: Aug. 21, 2012

(54) METHODS OF IDENTIFYING AND TREATING INDIVIDUALS EXHIBITING MUTANT KIT PROTEIN

(75) Inventors: Francis Y. Lee, Yardley, PA (US); Michael C. Heinrich, Lake Oswego, OR (US)

(73) Assignees: Bristol-Myers Squibb Company, Princeton, NJ (US); Oregon Health and Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 753 days.

(21) Appl. No.: 11/921,781

(22) PCT Filed: Jun. 9, 2006

(86) PCT No.: PCT/US2006/022564
§ 371 (c)(1),
(2), (4) Date: Apr. 2, 2009

(87) PCT Pub. No.: WO2006/135790
PCT Pub. Date: Dec. 21, 2006

(65) Prior Publication Data
US 2009/0221601 A1 Sep. 3, 2009

Related U.S. Application Data

(60) Provisional application No. 60/689,113, filed on Jun. 9, 2005, provisional application No. 60/736,668, filed on Nov. 15, 2005, provisional application No. 60/748,418, filed on Dec. 8, 2005.

(51) Int. Cl.
*A61K 31/497* (2006.01)
(52) U.S. Cl. .................................. 514/252.14
(58) Field of Classification Search ......................... None
See application file for complete search history.

(56) References Cited

U.S. PATENT DOCUMENTS

| | | | |
|---|---|---|---|
| 6,011,029 A | 1/2000 | Ding et al. | |
| 6,440,707 B1 | 8/2002 | Kwok et al. | |
| 6,458,540 B1 | 10/2002 | Ramberg | |
| 6,596,754 B1 | 7/2003 | Hara et al. | |
| 7,125,875 B2 | 10/2006 | Das et al. | |
| 2004/0253205 A1 | 12/2004 | Yamamoto et al. | |
| 2005/0009891 A1 | 1/2005 | Lee | |
| 2005/0054617 A1 | 3/2005 | Moussy et al. | |
| 2005/0215795 A1 | 9/2005 | Chen et al. | |
| 2006/0019256 A1* | 1/2006 | Clarke et al. | 435/6 |
| 2006/0094728 A1 | 5/2006 | Lee | |
| 2006/0235006 A1 | 10/2006 | Lee et al. | |
| 2006/0251723 A1 | 11/2006 | Gao et al. | |

FOREIGN PATENT DOCUMENTS

| | | |
|---|---|---|
| WO | WO 03/070234 A1 * | 8/2003 |
| WO | WO 2004/015130 | 2/2004 |
| WO | WO 2004/085388 | 10/2004 |

OTHER PUBLICATIONS

Schittenhelm et al. (Blood Nov. 16, 2005 106(11), Pt.1, pp. 938A-939A).*
Shivakrupa et al. (Cancer Research Aug. 1, 2003, 63:4412-4419).*
Wiesenthal (http://weisenthal.org/feedback.html, Feb. 4, 2002).*
Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Embleton et al (Immunol Ser, 1984, 23:181-207).*
Tian, J. et al. (Physiol Genomics, 2004, 17:170-182).*
Zips et al. (In vivo, 2005, 19:1-7).*
Fiskus et al. (Clin. Cancer. Res. 2006, 12(19): 5869-5878).*
Akin et al., "The biology of Kit in disease and the application of pharmacogenetics," The Journal of Allergy and Clinical immunology, 114(1):13-19 (2004).
McKinzie et al., "Detection of rare K-ras codon 12 mutations using allele-specific competitive blocker PCR," Mutation Research, 517(1-2):209-220 (2002).
Orou et al., "Allele-Specific Competitive Blocker PCR: A One-Step Method With Applicability to Pool Screening," Human Mutation, 6(2):163-169 (1995).
Alderborn, A., et al., "Determination of single-nucleotide polymorphisms by real-time pyrophosphate DNA sequencing," *Genome Research*, 2000, 10:1249-1258.
Akin C, et al. "A novel form of mastocytosis associated with a transmembrane c-kit mutation and response to imatinib," *Blood*, 2004, 103(8):3222-3225.
Akin C and Metacalf DD. "Systemic Mastocytosis," *Annual Review of Medicine*, 2004, 55:419-432.
Armstrong, B., et al., "Suspension arrays for high throughput, multiplexed single nucleotide polymorphism genotyping," *Cytometry*, 2000, 40:102-108.
Banér, J., et al. "Signal amplification of padlock probes by rolling circle replication," *Nucleic Acids Research*, 1998 26:5073-5078.
Baner, J. et al.,"More keys to padlock probes: mechanisms for high-throughput nucleic acid analysis," *Current Opinion in Biotechnology*, 2001, 12:11-15.
Beaudet, L., et al., "Homogeneous assays for single-nucleotide polymorphism typing using AlphaScreen," *Genome Research*, 2001, 11:600-608.
Beghini A, et al. "KIT activating mutations: incidence in adult and pediatric acute myeloid leukemia, and identification of an internal tandem duplication," *Haematologica*, 2004, 89(8):920-925.
Bouchie, A., "Haplotype map planned," *Nature Biotechnology*, 2001, 19:704.

(Continued)

*Primary Examiner* — Peter J Reddig
(74) *Attorney, Agent, or Firm* — Ropes & Gray LLP; Karen Mangasarian; Brian M. Gummow

(57) ABSTRACT

The invention described herein relates to methods of identifying and treating individuals with protein tyrosine kinase associated disorders that have, or may, become resistant to treatment with a kinase inhibitor such as imatinib due to a gain-of-function mutation in KIT tyrosine kinase.

12 Claims, 23 Drawing Sheets

OTHER PUBLICATIONS

Bray, M., et al. "High-throughput multiplex SNP genotyping with MALDI-TOF mass spectrometry: practice, problems and promise," *Human Mutation*, 2001, 17:296-304.

Brown, P. & Botstein, D., "Exploring the new world of the genome with DNA microarrays," *Nature Genetics*, 1999, 21:33-37.

Cai, H. et al., "Flow cytometry-based minisequencing: a new platform for high-throughput single-nucleotide polymorphism scoring," *Genomics*, 2000, 66:135-143.

Cargill, M. et al. "Characterization of single-nucleotide polymorphisms in coding regions of human genes," *Nature Genetics*, 1999, 22:231-238.

Chan, W. & Nie, S., "Quantum dot bioconjugates for ultrasensitive nonisotopic detection" *Science*, 1998, 281:2016-2018.

Chen, X., et al., "Fluorescence polarization in homogeneous nucleic acid analysis," *Genome Research*, 1999, 9:492-498.

Chen, J. et al., "A microsphere-based assay for multiplexed single nucleotide polymorphism analysis using single base chain extension," *Genome Research*, 2000, 10:549-557.

Chou TC and Talalay P. "Quantitative analysis of dose-effect relationships: the combined effects of multiple drugs or enzyme inhibitors," *Advances in Enzyme Regulation*, 1984, 22:27-55.

Corless CL, et al. "Biology of gastrointestinal stromal tumors," *Journal of Clinical Oncology*, 2004, 22(18):3813-3825.

Debiec-Rychter M, et al. "Use of c-KIT/PDGFRA mutational analysis to predict the clinical response to imatinib in patients with advanced gastrointestinal stromal tumours entered on phase I and II studies of the EORTC Soft Tissue and Bone Sarcoma Group," *European Journal of Cancer*, 2004, 40:689-95.

Dong, S. et al., "Flexible use of high-density oligonucleotide arrays for single-nucleotide polymorphism discovery and validation," *Genome Research*, 2001, 11:1418-1424.

Fan, J. et al., "Parallel genotyping of human SNPs using generic high-density oligonucleotide tag arrays," *Genome Research*, 2000, 10:853-860.

Faruqi, F. et al. "High-throughput genotyping of single nucleotide polymorphisms with rolling circle amplification," *BMC Genomics*, 2001, 2:4.

Fulton, R., et al., "Advanced multiplexed analysis with the FlowMetrix™ system," *Clinical Chemistry*, 1997, 43:1749-1756.

Genbank Accession No. gi|NP_000213, Oct. 12, 2008.

Genbank Accession No. gi|34084, Oct. 21, 2004.

Gerry, N. et al., "Universal DNA microarray method for multiplex detection of low abundance point mutations," *Journal of Molecular Biology*, 1999, 292:251-262.

Gibson, N. et al., "A homogeneous method for genotyping with fluorescence polarization," *Clinical Chemistry*, 1997, 43:1336-1341.

Griffin, T. & Smith, L., "Single-nucleotide polymorphism analysis by MALDI-TOF mass spectrometry," *Trends in Biotechnology*, 2000, 18:77-84.

Griffin, T., et al., "Genetic analysis by peptide nucleic acid affinity MALDI-TOF mass spectrometry," *Nature Biotechnology*, 1997, 15:1368-1372.

Griffin, T., et al., "Direct genetic analysis by matrix-assisted laser desorption/ionization mass spectrometry," *Proceedings of the National Academy of Sciences U S A*, 1999, 96:6301-6306.

Gut, I.,"Automation in genotyping of single nucleotide polymorphisms," *Human Mutation*, 2001, 17:475-492.

Hacia, J., "Resequencing and mutational analysis using oligonucleotide microarrays," *Nature Genetics*, 1999, 21:42-47.

Haff, L. & Smirnov, I., "Single-nucleotide polymorphism identification assays using a thermostable DNA polymerase and delayed extraction MALDI-TOF mass spectrometry," *Genome Research*, 1997, 7:378-388.

Hall, J. et al., "Sensitive detection of DNA polymorphisms by the serial invasive signal amplification reaction," *Proceedings of the National Academy of Sciences U S A*, 2000, 97:8272-8277.

Halushka, M. et al., "Patterns of single-nucleotide polymorphisms in candidate genes for blood-pressure homeostasis," *Nature Genetics*, 1999, 22:239-247.

Han, M., et al., "Quantum-dot-tagged microbeads for multiplexed optical coding of biomolecules," *Nature Biotechnology*, 2001, 19:631-635.

Hatch, A., et al., "Rolling circle amplification of DNA immobilized on solid surfaces and its application to multiplex mutation detection," *Genetic Analysis*, 1999, 15:35-40.

Head, S. et al., "Nested genetic bit analysis (N-GBA) for mutation detection in the p53 tumor suppressor gene," *Nucleic Acids Research*, 1997, 25:5065-5071.

Heinrich MC, et al. "Biology and genetic aspects of gastrointestinal stromal tumors: KIT activation and cytogenetic alterations," *Human Pathology*, 2002, 33(5):484-495.

Heinrich MC, et al. "Inhibition of c-Kit Receptor Tyrosine Kinase Activity by STI 571, a Selective Tyrosine Kinase Inhibitor," *Blood*, 2000, 96(3):925-932.

Heinrich MC, et al. "Kinase mutations and imatinib response in patients with metastatic gastrointestinal stromal tumor," *Journal of Clinical Oncology*, 2003, 21(23):4342-4349.

Heinrich MC, et al. "PDGFRA activating mutations in gastrointestinal stromal tumors," *Science*, 2003, 299(5607):708-710.

Hensel, M. et al., "Simultaneous identification of bacterial virulence genes by negative selection," *Science*, 1995, 269;400-403.

Herschlag, D., "RNA chaperones and the RNA folding problem," *Journal of Biological Chemistry*, 1995, 270:20871-20874.

Hirschhorn, J. et al., "SBE-TAGS: an array-based method for efficient single-nucleotide polymorphism genotyping," *Proceedings of the National Academy of Sciences U S A*, 2000, 97:12164-12169.

Hoatlin ME, et al. "The Fanconi anemia group C gene product is located in both the nucleus and cytoplasm of human cells," *Blood*, 1998, 91(4):1418-1425.

Hsu, T., et al., "Genotyping single-nucleotide polymorphisms by the invader assay with dual-color fluorescence polarization detection," *Clinical Chemistry*, 2001, 47:1373-1377.

Iannone, M. et al., "Multiplexed single nucleotide polymorphism genotyping by oligonucleotide ligation and flow cytometry," *Cytometry*, 2000, 39:131-140.

Jackson, P., et al., "Mass spectrometry for genotyping: an emerging tool for molecular medicine," *Molecular Medicine Today*, 2000, 6:271-276.

Jiang-Baucom, P., et al., "DNA typing of human leukocyte antigen sequence polymorphisms by peptide nucleic acid probes and MALDI-TOF mass spectrometry," *Analytical Chemistry*, 1997, 69:4894-4898.

Kemmer K, et al. "KIT mutations are common in testicular seminomas," *The American Journal of Pathology*, 2004, 164(1):305-313.

Kokoris, M. et al., "High-throughput SNP genotyping with the Masscode system," *Molecular Diagnosis*, 2000, 5:329-340.

Kwok, P., "High-throughput genotyping assay approaches," *Pharmacogenomics*, 2000, 1:95-100.

Ladner, D. et al., "Multiplex detection of hotspot mutations by rolling circle-enabled universal microarrays," *Laboratory Investigation*, 2001, 81:1079-1086.

Landegren, U., et al., "Reading Bits of Genetic Information: Methods for Single-Nucleotide Polymorphism Analysis," *Genome Research*, 1998, 8:769-776.

Latif, S., et al., "Fluorescence polarization in homogeneous nucleic acid analysis II: 5'-nuclease assay," *Genome Research*, 2001, 11:436-440.

Lawley, W. et al., "Detection of an activating c-kit mutation by real-time PCR in patients with anaphylaxis," *Mutation Research*, 2005, 572:1-13.

Li, J. et al., "Single nucleotide polymorphism determination using primer extension and time-of-flight mass spectrometry," *Electrophoresis*, 1999, 20:1258-1265.

Lindblad-Toh, K. et al., "Large-scale discovery and genotyping of single-nucleotide polymorphisms in the mouse," *Nature Genetics*, 2000, 24:381-386.

Lindroos, K., et al., "Minisequencing on oligonucleotide microarrays: comparison of immobilisation chemistries," *Nucleic Acids Research*, 2001, 29:E69-9.

Lipshutz, R., et al., "High density synthetic oligonucleotide arrays," *Nature Genetics*, 1999, 21:20-24.

Little, D., et al., "Mass spectrometry from miniaturized arrays for full comparative DNA analysis," *Nature Medicine*, 1997, 3:1413-1416.

Little, D. et al. "MALDI on a chip: analysis of arrays of low-femtomole to subfemtomole quantities of synthetic oligonucleotides and DNA diagnostic products dispensed by a piezoelectric pipet," *Analytical Chemistry*, 1997, 69:4540-4546.

Livak, K., "Allelic discrimination using fluorogenic probes and the 5' nuclease assay," *Genetic Analysis*, 1999, 14:143-149.

Lizardi, P. et al., "Mutation detection and single-molecule counting using isothermal rolling-circle amplification," *Nature Genetics*, 1998, 19:225-232.

Lombardo LJ, et al. "Discovery of N-(2-chloro-6-methyl-phenyl)-2-(6-(4-(2-hydroxyethyl)-piperazin-1-yl)-2-methylpyrmidin-4-ylamino)thiazole-5-carboxamide (BMS-354825), a dual SRC/ABL kinase inhibitor with potent antitumor activity in preclinical assays," *Journal of Medicinal Chemistry*, 2004, 47: 6658-6661.

Longley BJ and Metcalf DD. "A Proposed Classification of Mastocytosis Incorporating Molecular Genetics," *Hematology-Oncology Clinics of North America*, 2000, 14(3):697-701.

Lyamichev, V. et al., "Polymorphism identification and quantitative detection of genomic DNA by invasive cleavage of oligonucleotide probes," *Nature Biotechnology*, 1999, 17:292-296.

Lu L, et al. "Retroviral-mediated gene transduction of c-kit into single hematopoietic progenitor cells from cord blood enhances erythroid colony formation and decreases sensitivity to inhibition by tumor necrosis factor-alpha and transforming growth factor-beta1," *Blood*, 1999, 94(7):2319-2332.

Ma Y, et al. "The c-KIT mutation causing human mastocytosis is resistant to STI571 and other KIT kinase inhibitors; kinases with enzymatic site mutations show different inhibitor sensitivity profiles than wild-type kinases and those with regulatory-type mutations," *Blood*, 2002, 99(5):1741-1744.

Marras, S., et al., "Multiplex detection of single-nucleotide variations using molecular beacons," *Genetic Analysis*, 1999, 14:151-156.

Mein, C. et al., "Evaluation of single nucleotide polymorphism typing with invader on PCR amplicons and its automation," *Genome Research*, 2000, 10:330-343.

Metcalfe, DD, "Classification and diagnosis of mastocytosis: current status," *Journal of Investigative Dermatology*, 1991, 96:2S-4S.

Metcalfe, DD and Akin C. "Mastocytosis: Molecular Mechanisms and Clinical Disease Heterogeneity," *Leukemia Research*, 2001, 25(7):577-582.

Michael, K., et al., "Randomly ordered addressable high-density optical sensor arrays," *Analytical Chemistry*, 1998, 70:1242-1248.

Myakishev, M., et al., "High-throughput SNP genotyping by allele-specific PCR with universal energy-transfer-labeled primers," *Genome Research*, 2001, 11:163-169.

Nikiforov, T. et al., "Genetic Bit Analysis: a solid phase method for typing single nucleotide polymorphisms," *Nucleic Acids Research*, 1994, 22:4167-4175.

Nilsson, M. et al., "Padlock probes: circularizing oligonucleotides for localized DNA detection," *Science*, 1994, 265:2085-2088.

O'Farrell AM, et al. "SU11248 is a novel FLT3 tyrosine kinase inhibitor with potent activity in vitro and in vivo," *Blood*, 2003, 101(9):3597-3605.

Ohnishi, Y. et al., "A high-throughput SNP typing system for genome-wide association studies," *Journal of Human Genetics*, 2001, 46:471-477.

Pastinen, T. et al., "A system for specific, high-throughput genotyping by allele-specific primer extension on microarrays," *Genome Research*, 2000, 10:1031-1042.

Pease, A. et al., "Light-generated oligonucleotide arrays for rapid DNA sequence analysis," *Proceedings of the National Academy of Sciences U S A*, 1994, 91:5022-5026.

Ranade, K. et al., "High-throughput genotyping with single nucleotide polymorphisms," *Genome Research*, 2001, 11;1262-1268.

Ronaghi, M., et al., "A sequencing method based on real-time pyrophosphate," *Science*, 1998, 281:363 and 365.

Ronaghi, M., "Pyrosequencing sheds light on DNA sequencing," *Genome Research*, 2001, 11:3-11.

Ross, P., et al., "High level multiplex genotyping by MALDI-TOF mass spectrometry," *Nature Biotechnology*, 1998, 16:1347-1351.

Ross, P., et al., "Discrimination of single-nucleotide polymorphisms in human DNA using peptide nucleic acid probes detected by MALDI-TOF mass spectrometry," *Analytical Chemistry*, 1997, 69:4197-4202.

Sapolsky, R. et al., "High-throughput polymorphism screening and genotyping with high-density oligonucleotide arrays," *Genetic Analysis*, 1999, 14:187-192.

Sauer, S. et al., "A novel procedure for efficient genotyping of single nucleotide polymorphisms," *Nucleic Acids Research*, 2000, 28:E13.

Sauer, S. et al., "Full flexibility genotyping of single nucleotide polymorphisms by the Good assay," *Nucleic Acids Research*, 2000, 28:E100.

Schittenhelm M., et al. "BMS-354825 potently inhibits the kinase activity of KIT activation loop mutations associated with systemic mastocytosis and induces apoptosis of mastocytosis cell lines," *Blood*, 2004, 104(11): 666A.

Schittenhelm M., et al. "Dasatinib (BMS-354825), a multi-targeted kinase inhibitor, inhibits the kinase activity or wild-type, juxtamembrane, and activation loop mutant KIT isoforms associated with malignancies," *Blood*, 2005, 106(11): 938A-939A.

Schittenhelm M., et al. "Dasatinib (BMS-354825), a dial SRC/ABL kinase inhibitor, inhibits the kinase activity or wild-type, juxtamembrane, and activation loop mutant KIT isoforms associated with malignancies," *Cancer Research*, 2006, 66(1): 473-481.

Shah NP, et al. "BMS-354825 is a SRC/ABL inhibitor with high nanomolar activity against the KIT D816V mutation, which drives systemic mastocytosis and is imatinib-resistant," *Blood*, 2004, 104(11):228A.

Shah NP, et al. "Dasatinib (BMS-354825) inhibits KIT D816V, an imatinib-resistant activating mutation that triggers neoplastic growth in most patients with systemic mastocytosis," *Blood*, 2006, 108(1): 286-291.

Shah NP, et al. "Overriding imatinib resistance with a novel ABL kinase inbitor," *Science*, 2004, 305(5682): 399-401.

Shoemaker, D., et al., "Quantitative phenotypic analysis of yeast deletion mutants using a highly parallel molecular bar-coding strategy," *Nature Genetics*, 1996, 14:450-456.

Shumaker, J., et al., "Mutation detection by solid phase primer extension," *Human Mutation*, 1996, 7:346-354.

Sotlar, K. et al., "One-step detection of c-kit point mutations using peptide nucleic acid-mediated polymerase chain reaction clamping and hybridization probes," *American Journal of Pathology*, 2003, 162(3):737-746.

Southern, E., Maskos, U. & Elder, J., "Analyzing and comparing nucleic acid sequences by hybridization to arrays of oligonucleotides: evaluation using experimental models," *Genomics*. 1993. 13:1008-1017.

Steemers, F., et al., "Screening unlabeled DNA targets with randomly ordered fiber-optic gene arrays," *Nature Biotechnology*, 2000, 18:91-94.

Sun, X., et al., "A new MALDI-TOF based mini-sequencing assay for genotyping of SNPS." *Nucleic Acids Research*, 2000, 28:E68.

Syvänen, A. et al., "Convenient and quantitative determination of the frequency of a mutant allele using solid-phase minisequencing: application to aspartylglucosaminuria in Finland," *Genomics*, 1992, 12:590-595.

Talpaz M, et al. "Hematologic and cytogenetic responses in imatinib-resistant accelerated and blast phase chronic myeloid leukemia (CML) patients treated with the dual SRC/ABL kinase inhibitor BMS-354825: Results from a phase I dose escalation study." *Blood*, 2004, 104(11): 10A.

Tang, K. et al., "Chip-based genotyping by mass spectrometry," *Proceedings of the National Academy of Sciences U S A*, 1999, 91:10016-10020.

Taranenko, N. et al., "Laser desorption mass spectrometry for point mutation detection," *Genetic Analysis*, 1996, 13:87-94.

Tefferi A and Pardanani A. "Clinical, Genetic, and Therapeutic Insights Into Systemic Mast Cell Disease," *Current Opinion in Hematology*, 2004, 11(1):58-64.

Tillib, S. & Mirzabekov, A., "Advances in the analysis of DNA sequence variations using oligonucleotide microchip technology." *Current Opinions in Biotechnology*, 2001, 12:53-58.

Tse KF, et al. "Constitutive activation of FLT3 stimulates multiple intracellular signal transducers and results in transformation," *Leukemia*, 2000, 14(10):1766-1776.

Tsuchihashi, Z. & Brown, P., "DNA strand exchange and selective DNA annealing promoted by the human immunodeficiency virus type 1 nucleocapsid protein," *Journal of Virology*, 1994, 68:5863-5870.

Valent P, et al. "Mast Cell Proliferative Disorders: Current View on Variants Recognized by the World Health Organization," *Hematology-Oncology Clinics of North America*, 2003, 17(5):1227-1241.

Valent P, et al. "Mastocytosis: pathology, genetics, and current options for therapy," *Leukemia and Lymphoma*, 2005, 46(1):35-48.

Wang, D. et al., "Large-scale identification, mapping, and genotyping of single-nucleotide polymorphisms in the human genome," *Science*, 1998, 280:1077-1082.

Whitcombe, D., Newton, C. & Little, S., "Advances in approaches to DNA-based diagnostics," *Current Opinions in Biotechnology*, 1998 9:602-608.

Winzeler, E. et al., "Direct allelic variation scanning of the yeast genome," *Science*, 1998, 281:1194-1197.

Ye, F. et al. "Fluorescent microsphere-based readout technology for multiplexed human single nucleotide polymorphism analysis and bacterial identification," *Human Mutation*, 2001, 17:305-316.

Yee KW, et al. "SU5416 and SU5614 inhibit kinase activity of wild-type and mutant FLT3 receptor tyrosine kinase," *Blood*, 2002, 100(8):2941-2949.

Yee KW, et al. "Synergistic effect of SU11248 with cytarabine or daunorubicin on FLT3 ITD-positive leukemic cells," *Blood*, 2004, 104(13):4202-4209.

Zhong, X., et al., "Visualization of oligonucleotide probes and point mutations in interphase nuclei and DNA fibers using rolling circle DNA amplification," *Proceedings of the National Academy of Sciences U S A*, 2001 98:3940-3945.

\* cited by examiner

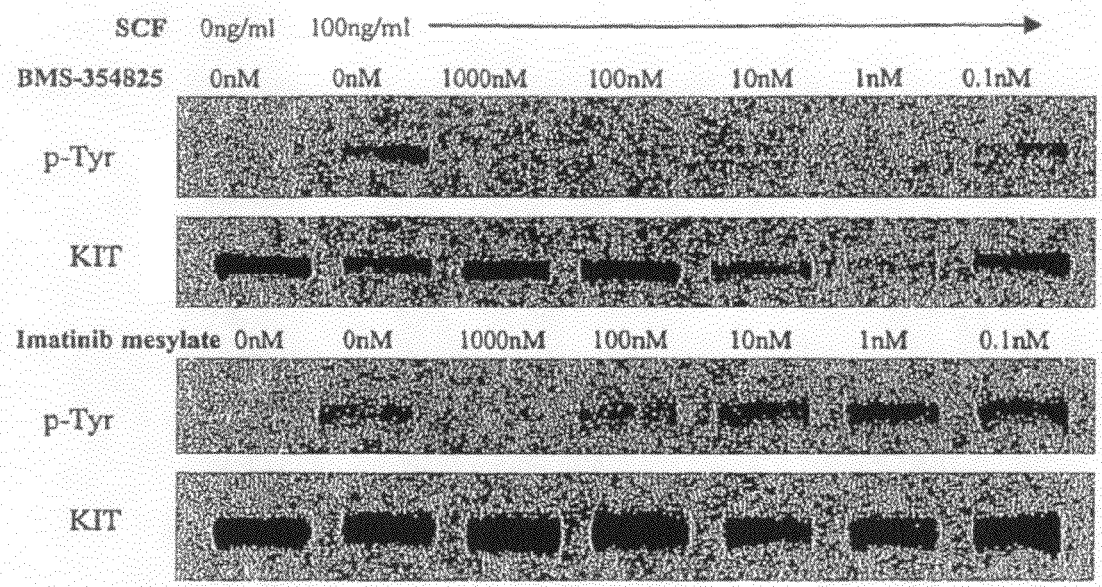
FIG. 1A
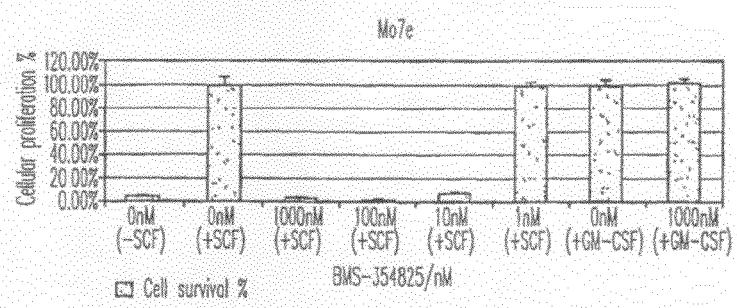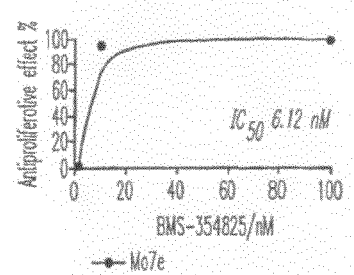
FIG. 1B

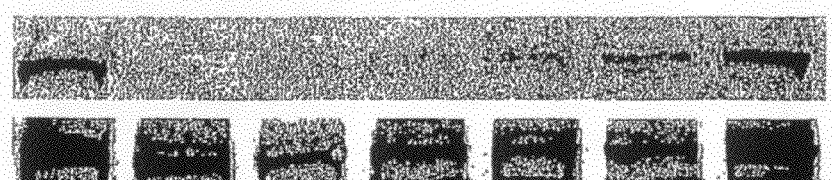
FIG. 2A
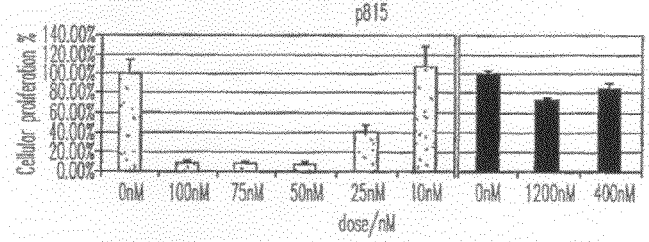 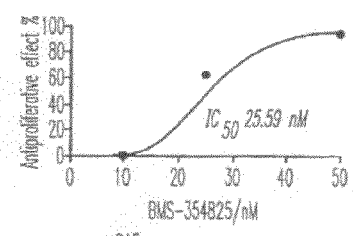
FIG. 2B
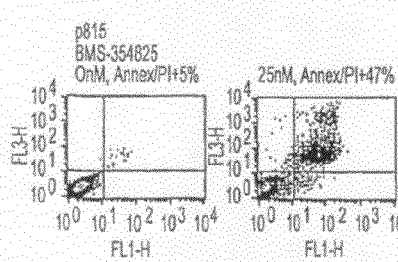 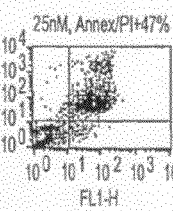 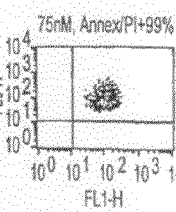 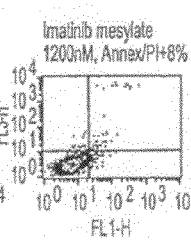 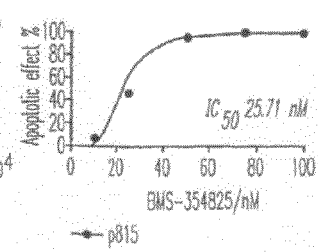
FIG. 2C Ba/F3 KIT D816V
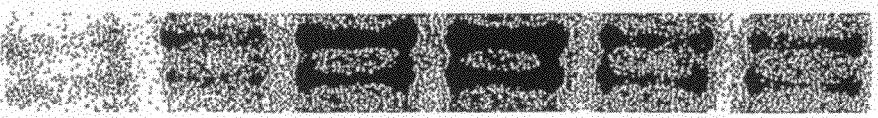
Ba/F3 KIT D816F
Ba/F3 KIT D816Y
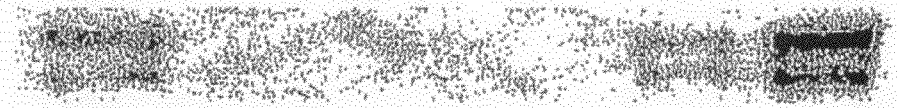
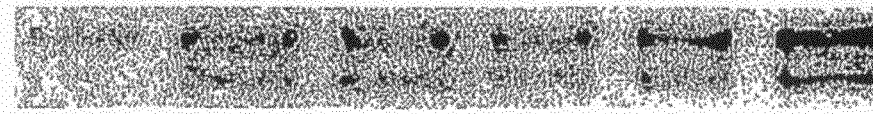
FIG. 3A

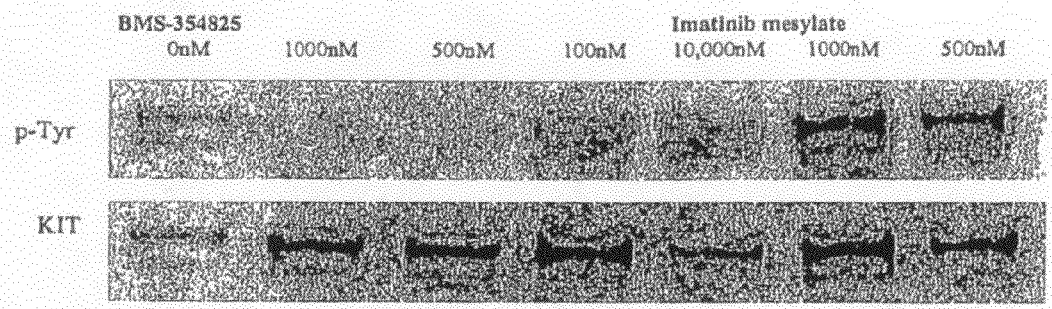
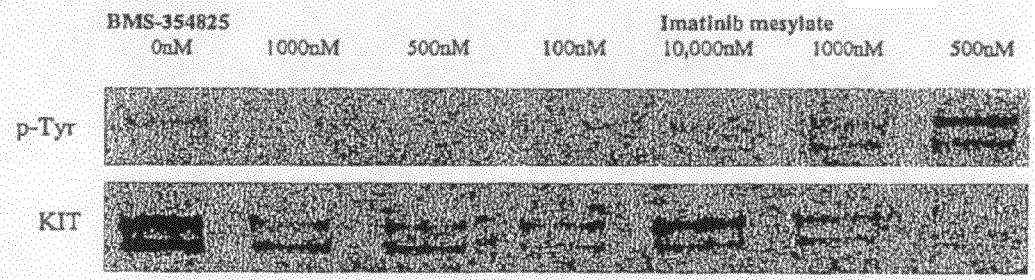
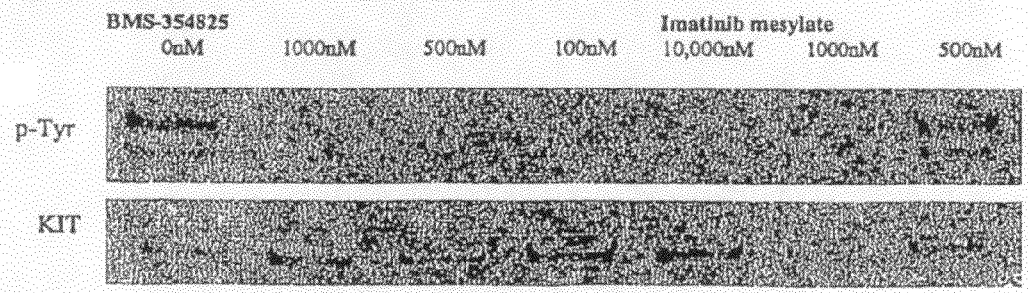
FIG. 3B

```
  1 mrgargawdf lcvllllllrv qtgssqpsvs pgepsppsih pgksdlivrv gdeirllctd
 61 pgfvkwtfei ldetnenkqn ewitekaeat ntgkytctnk hglsnsiyvf vrdpaklflv
121 drslygkedn dtlvrcpltd pevtnyslkg cqgkplpkdl rfipdpkagi miksvkrayh
181 rlclhcsvdq egksvlsekf ilkvrpafka vpvvsvskas yllregeeft vtctikdvss
241 svystwkren sqtklqekyn swhhgdfnye rqatltissa rvndsgvfmc yanntfgsan
301 vtttlevvdk gfinifpmin ttvfvndgen vdliveyeaf pkpehqqwiy mnrtftdkwe
361 dypksenesn iryvselhlt rlkgteggty tflvsnsdvn aaiafnvyvn tkpeiltydr
421 lvngmlqcva agfpeptidw yfcpgteqrc sasvlpvdvq tlnssgppfg klvvqssids
481 safkhngtve ckayndvgkt sayfnfafkg nnkeqihpht lftplligfv ivagmmciiv
541 miltykylqk pmyevqwkvv eeingnnyvy idptqlpydh kwefprnrls fgktlgagaf
601 gkvveatayg liksdaamtv avkmlkpsah lterealmse lkvlsylgnh mnivnllgac
661 tiggptlvit eyccygdlln flrrkrdsfi cskqedhaea alyknllhsk esscsdstne
721 ymdmkpgvsy vvptkadkrr svrigsyier dvtpaimedd elaldledll sfsyqvakgm
781 aflaskncih rdlaarnill thgritkicd fglardiknd snyvvkgnar lpvkwmapes
841 ifncvytfes dvwsygiflw elfslgsspy pgmpvdskfy kmikegfrml spehapaemy
901 dimktcwdad plkrptfkqi vqliekqise stnhiysnla ncspnrqkpv vdhsvrinsv
961 gstasssqpl lvhddv
```

FIG. 8

```
  1 atgagaggcg ctcgcggcgc ctgggatttt ctctgcgttc tgctcctact gcttcgcgtc
 61 cagacaggct cttctcaacc atctgtgagt ccaggggaac cgtctccacc atccatccat
121 ccaggaaaat cagacttaat agtccgcgtg ggcgacgaga ttaggctgtt atgcactgat
181 ccgggctttg tcaaatggac ttttgagatc ctggatgaaa cgaatgagaa taagcagaat
241 gaatggatca cggaaaaggc agaagccacc aacaccggca aatacacgtg caccaacaaa
301 cacggcttaa gcaattccat ttatgtgttt gttagagatc ctgccaagct tttccttgtt
361 gaccgctcct tgtatgggaa agaagacaac gacacgctgg tccgctgtcc tctcacagac
421 ccagaagtga ccaattattc cctcaagggg tgccagggga agcctcttcc caaggacttg
481 aggtttattc ctgaccccaa ggcgggcatc atgatcaaaa gtgtgaaacg cgcctaccat
541 cggctctgtc tgcattgttc tgtggaccag gagggcaagt cagtgctgtc ggaaaaattc
601 atcctgaaag tgaggccagc cttcaaagct gtgcctgttg tgtctgtgtc caaagcaagc
661 tatcttctta gggaagggga agaattcaca gtgacgtgca aataaaaga tgtgtctagt
721 tctgtgtact caacgtggaa aagagaaaac agtcagacta actacagga gaaatataat
781 agctggcatc acggtgactt caattatgaa cgtcaggcaa cgttgactat cagttcagcg
841 agagttaatg attctggagt gttcatgtgt tatgccaata atacttttgg atcagcaaat
901 gtcacaacaa ccttggaagt agtagataaa ggattcatta atatcttccc catgataaac
961 actacagtat tgtaaacga tggagaaaat gtagatttga ttgttgaata tgaagcattc
1021 cccaaacctg aacaccagca gtggatctat atgaacagaa ccttcactga taaatgggaa
1081 gattatccca gtctgagaa tgaaagtaat atcagatacg taagtgaact tcatctaacg
1141 agattaaaag gcaccgaagg aggcacttac acattcctag tgtccaattc tgacgtcaat
1201 gctgccatag catttaatgt ttatgtgaat acaaaaccag aaatcctgac ttacgacagg
1261 ctcgtgaatg gcatgctcca atgtgtggca gcaggattcc cagagcccac aatagattgg
1321 tatttttgtc caggaactga gcagagatgc tctgcttctg tactgccagt ggatgtgcag
1381 acactaaact catctgggcc accgtttgga aagctagtgg ttcagattc tatagattct
1441 agtgcattca agcacaatgg cacggttgaa tgtaaggctt acaacgatgt gggcaagact
1501 tctgcctatt ttaactttgc atttaaaggt aacaacaaag agcaaatcca tccccacacc
1561 ctgttcactc ctttgctgat tggtttcgta atcgtagctg gcatgatgtg cattattgtg
1621 atgattctga cctacaaata tttacagaaa cccatgtatg aagtacagtg gaaggttgtt
1681 gaggagataa atggaaacaa ttatgtttac atagacccaa cacaacttcc ttatgatcac
1741 aaatgggagt tcccagaaaa caggctgagt tttgggaaaa ccctgggtgc tggagctttc
1801 gggaaggttg ttgaggcaac tgcttatggc ttaattaagt cagatgcggc catgactgtc
1861 gctgtaaaga tgctcaagcc gagtgcccat ttgacagaac gggaagccct catgtctgaa
1921 ctcaaagtcc tgagttacct tggtaatcac atgaatattg tgaatctact ggagcctgc
1981 accattggag ggcccaccct ggtcattaca gaatattgtt gctatggtga tctttgaat
2041 ttttgagaa gaaacgtga ttcatttat tgttcaaagc aggaagatca tgcagaagct
2101 gcactttata agaatcttct gcattcaaag gagtcttcct gcagcgatag tactaatgag
2161 tacatggaca tgaaacctgg agtttcttat gttgtcccaa ccaaggccga caaaaggaga
2221 tctgtgagaa taggctcata catagaaaga gatgtgactc ccgccatcat ggaggatgac
2281 gagttggccc tagacttaga agacttgctg agcttttctt accaggtggc aaagggcatg
2341 gctttcctcg cctccaagaa ttgtattcac agagacttgg cagccagaaa tatcctcctt
2401 actcatggtc ggatcacaaa gatttgtgat tttggtctag ccagagacat caagaatgat
2461 tctaattatg tggttaaagg aaacgctcga ctacctgtga gtggatggc acctgaaagc
2521 attttcaact gtgtatacac gtttgaaagt gacgtctggt cctatgggat ttttctttgg
2581 gagctgttct ctttaggaag cagccctat cctggaatgc cggtcgattc taagttctac
2641 aagatgatca aggaaggctt ccggatgctc agccctgaac acgcacctgc tgaaatgtat
2701 gacataatga aagacttgct ggatgcagat ccctaaaaa gaccaacatt caagcaaatt
2761 gttcagctaa ttgaagca gatttcagag agcaccaatc atatttactc caacttagca
2821 aactgcagcc ccaaccgaca gaagccgtg gtagaccatt ctgtgcggat caattctgtc
2881 ggcagcaccg cttcctcctc ccagcctctg cttgtgcacg acgatgtctg a
```

FIG. 9

Design of mutant-specific and blocking primers

Mutant-specific primer

```
                        GTGATTTTGGTCTAGCCAGAAT-> (SEQ ID NO:6)
                        |||||||||||||||||||*|
D816V Mutant sequence   ---CACTAAAACCAGATCGGTCTCA---

GTGATTTTGGTCTAGCCAGAAT-> (SEQ ID NO:6)
                        |||||||||||||||||||*|
D816F Mutant sequence   ---CACTAAAACCAGATCGGTCTAA---

GTGATTTTGGTCTAGCCAGAAT    (SEQ ID NO:6)
                        ||||||||||||||||||||**
Wild-type sequence      ---CACTAAAACCAGATCGGTCTCT---
```

Blocking oligonucleotide

```
                        GTGATTTTGGTCTAGCCAGAAA$^x$    (SEQ ID NO:7)
                        ||||||||||||||||||||**
D816V Mutant sequence   ---CACTAAAACCAGATCGGTCTCA---

GTGATTTTGGTCTAGCCAGAAA$^x$    (SEQ ID NO:7)
                        ||||||||||||||||||||**
D816F Mutant sequence   ---CACTAAAACCAGATCGGTCTAA---

GTGATTTTGGTCTAGCCAGAAA$^x$    (SEQ ID NO:7)
                        |||||||||||||||||||*|
Wild-type sequence      ---CACTAAAACCAGATCGGTCTCT---
```

FIG. 16

Cases with known *KIT* D816 mutation

| Case | Diagnosis | DNA Source | DNA Sequence | AS-PCR |
|---|---|---|---|---|
| 1 LH AML 8;21 | AML | Fresh cells | D816V | Positive |
| 2 AML 8507 | AML | Fresh cells | D816V | Positive |
| 3 AML 7904 | AML | Fresh cells | D816V | Positive |
| 4 H01-6922 | AML | Fresh cells | D816V | Positive |
| 5 H01-8093 | AML | Fresh cells | D816V | Positive |
| 6 S-5580 | AML | Fresh cells | D816V | Positive |
| 7 AML 6446 | AML | Fresh cells | D816V | Positive |
| 8 H01-6204 | AML | Fresh cells | D816V | Positive |
| 9 UH949-25 | Seminoma | Paraffin | D816V | Positive |
| 10 S95-4633 | Seminoma | Paraffin | D816V | Positive |
| 11 UH0007-03 | Seminoma | Paraffin | D816V | Positive |
| 12 S91-3671 | Seminoma | Paraffin | D816H | Negative |
| 13 S97-1691 | Seminoma | Paraffin | D816H | Negative |
| 14 STI-2-157 post STI | GIST# | Paraffin | D816H | Negative |
| 15 SU-0002 post | GIST# | Paraffin | D816H | Negative |
| 16 ST03-781 | GIST# | Paraffin | D816G | Negative |
| 17 | GIST# | Paraffin | D816A | Negative |
| 18 H01-8816 | AML | Fresh cells | D816Y and D816V* | Positive |
| 19 H01-8213 | AML | Fresh cells | D816Y and D816V* | Positive |
| 20 SU-0010 day1 | GIST# | Paraffin | D816H | Positive |

GIST samples from patients with acquired imatinib resistance.
*D816V detected at low levels (5-10%) among subclones from exon 17 amplimers of these cases.

FIG. 19

Table 2. AS-PCR Results on samples from patients with clinically suspected mast cell disease

| Sample # | | Diagnosis | Age | Sex | Site | DNA Source | HPLC | Sequence | AS-PCR |
|---|---|---|---|---|---|---|---|---|---|
| 21 | S06-2323 | Mastocytosis | 64 | M | Skin | Paraffin | pm/snp | D816V | Positive |
| 22 | D99-3540 B | Mastocytosis | 48 | F | Skin | Paraffin | pm/snp | D816V | Positive |
| 23 | S04-1985 | Mastocytosis | 28 | M | Skin | Paraffin | pm/snp | SNP I798I & D816V | Positive |
| 24 | S04-6210 | Mastocytosis | 22 | F | LN | Paraffin | pm/snp | D816V | Positive |
| 25 | SH04-28941 | Mastocytosis | 74 | M | BM | Fresh aspirate | pm/snp | D816V | Positive |
| 26 | S06-604 | Mastocytosis | 65 | F | BM | Fresh aspirate | pm/snp | D816V | Positive |
| 27 | S05-11275 | Mastocytosis | 39 | F | BM | Fresh aspirate | pm/snp | D816V | Positive |
| 28 | S05-14307 | Mastocytosis | 56 | F | BM | Fresh aspirate | pm/snp | D816V | |
| 29 | B2225 pt118 (TL) | Mast cell leukemia | 64 | M | BM | Paraffin | pm/snp | D816V | Positive |
| 30 | H01-1516 (shavings) | SM-AML | 46 | M | BM | Fresh | pm/snp | D816V | Positive |
| 31 | H05-811 | SM-AML | 61 | M | Blood | | | | Positive |
| 32 | H04-1105 | Mastocytosis | 61 | M | Colon | Paraffin | WT | WT | Positive |
| 33 | S05-6360 | Mastocytosis | 56 | M | Skin | Paraffin | WT | ND | Positive |
| 34 | S04-8766 | Mastocytosis | 62 | M | BM | Formalin-fixed | WT | ND | Positive |
| 35 | S05-9455 | Mastocytosis | 40 | F | BM | Fresh aspirate | WT | WT | Positive |
| 36 | H01-1554 | Mastocytosis | 46 | F | BM | Paraffin | WT | WT | Positive |
| 37 | H05-1227 | Mastocytosis | 26 | F | BM | Paraffin | WT | WT | Positive |
| 38 | S06-3512 | Mastocytosis | 64 | M | BM | Fresh aspirate | WT | WT | Positive |
| 39 | S05-9450 | Mastocytosis | 55 | M | BM | Fresh aspirate | pm/snp | SNP I798I | Positive |
| 40 | S05-6361 | Mastocytosis | 61 | F | BM | Fresh aspirate | pm/snp? | WT | Positive |
| 41 | S97-14694-2 (2x) | Mastocytosis | 78 | F | Skin | Paraffin | WT | WT | Negative |
| 42 | S00-808 | Mastocytosis | 35 | M | Skin | Paraffin | WT | WT | Negative |
| 43 | S99-20010 (2X) | Mastocytosis | 31 | F | Skin | Paraffin | WT | WT | Negative |
| 44 | S02-306649-1 | Mastocytosis | 24 | F | Skin | Paraffin | WT | ND | Negative |
| 45 | S95-22103 | Mastocytosis | 71 | F | Skin | Paraffin | WT | ND | Negative |

FIG. 20A

| | | | | | | | | |
|---|---|---|---|---|---|---|---|---|
| 46 | S99-26256 | Mastocytosis | 30 | F | Skin | Paraffin | WT | | Negative |
| 47 | S92-10780-2 | Mastocytosis | 52 | F | Skin | Paraffin | WT | ND | Negative |
| 48 | D99-2246 | Mastocytosis | 44 | F | Skin | Paraffin | WT | ND | Negative |
| 49 | D98-3508 | Mastocytosis | 38 | F | Skin | Paraffin | WT | ND | Negative |
| 50 | H05-1442 | Mastocytosis | 40 | M | Blood | Blood | WT | ND | Negative |
| 51 | S05-11015 | Mastocytosis | 60 | F | BM | Paraffin | WT | ND | Negative |
| 52 | S05-11764 | Mastocytosis | 35 | F | BM | Fresh aspirate | WT | ND | Negative |
| 53 | H05-2832 | Mastocytosis? | 52 | F | BM | Fresh aspirate | WT | ND | Negative |
| 54 | S05-9691 | Mastocytosis | 18 | M | BM | Fresh aspirate | WT | ND | Negative |
| 55 | S05-9273 | Mastocytosis? | 65 | M | BM | Formalin-fixed | WT | ND | Negative |
| 56 | S02-5803 | SM-MPD | 71 | F | BM | Paraffin | WT | ND | Negative |
| 57 | Texas Mast 001 | SM-MPD | 73 | M | BM | Paraffin | WT | ND | Negative |
| 58 | (MR#1461058) DNA N05-1403 | SM-MPD | 57 | F | BM | Fresh aspirate | WT | ND | Negative |

BM – bone marrow; LN – lymph node; WT – wild-type; ND – not done;
SM-AML – acute myelogenous leukemia arising from systemic mastocytosis;
SM-MPD – myeloproliferative disorder with excess mast cells

FIG. 20B

METHODS OF IDENTIFYING AND TREATING INDIVIDUALS EXHIBITING MUTANT KIT PROTEIN

This application is a national stage filing under 35 U.S.C. §371 of International Application PCT/US2006/022564, filed Jun. 9, 2006, which claims the benefit of U.S. Provisional Applications 60/689,113, filed Jun. 9, 2005, 60/736,668, filed Nov. 15, 2005 and 60/748,418, filed Dec. 8, 2005. The entire disclosures of each of these referenced applications are incorporated herein by reference.

The instant application contains a Sequence Listing which has been submitted via EFS-Web and is hereby incorporated by reference in its entirety. Said ASCII copy, created on Oct. 28, 2011, is named Sequence_Listing.TXT, and is 24,279 bytes in size.

FIELD OF THE INVENTION

The invention described herein relates to mutant KIT proteins, and to diagnostic and therapeutic methods and compositions useful in the management of disorders, for example cancers, involving cells that express such mutant KIT proteins.

BACKGROUND OF THE INVENTION

Proto-oncogene c-kit encodes the transmembrane type m tyrosine kinase, KIT protein, which is the receptor for stem cell factor (SCF). KIT is structurally characterized by an extracellular (EC) domain with 5 immunoglobulin like repeats, a single transmembrane domain, a juxtamembrane domain ("JM") and a cytoplasmic tyrosine kinase domain. The kinase domain consists of the N-terminal (TK1) and C-terminal (TK2) lobes that are separated by a hydrophilic kinase insert. The TK2 domain contains the kinase activation loop ("AL"), a critical hinged region of the kinase that must assume a particular conformation in order to allow full kinase activation.

The single letter amino acid sequence of wild type human KIT protein is shown in FIG. 8 (SEQ ID NO:2) (NP_000213). The nucleic acid sequence of KIT is encoded by nucleotides 1-2928 of the sequence shown in FIG. 9 (SEQ ID NO: 1).

Under normal circumstances SCF binds to KIT inducing homodimerization of the receptor leading to intrinsic kinase activity and resulting in autophosphorylation of tyrosine residues. KIT then becomes the docking site for various SH2 domain signaling molecules. The KIT receptor is expressed on melanocytes, mast cells, primitive hematopoietic cells, primordial germ cells, intraepithelial lymphocytes and interstitial cells of Cajal.

Imatinib mesylate (also known as STI-571) is a potent KIT tyrosine kinase inhibitor and is now standard of care in advanced gastrointestinal stromal tumors ("GIST"), targeting autoactivating imatinib-sensitive KIT mutations that are mainly located in the JM domain in this protein. As used herein the term "imatinib" is used to refer to imatinib mesylate or STI-571. Although imatinib is a potent inhibitor of the kinase activity of wild type KIT and certain JM mutant KIT isoforms, many mutant KIT isoforms are resistant to clinically achievable doses of imatinib. Imatinib can only bind to the inactive or "closed" conformation of KIT. However, KIT AL mutations not only activate kinase activity but also stabilize the activation loop in an "open" conformation that does not allow productive imatinib binding. Activating KIT AL mutations are found in association with AML, mast cell disease, in particular systemic mastocytosis ("SM"), a subset of sinonasal NK/T-cell and Non-Hodgkin Lymphoma, seminoma/dysgerminoma and imatinib-resistant GIST. (See, e.g., US 2004/0253205; US 2005/0054617 and references cited therein).

Mastocytoses are a very heterogeneous group of disorders characterized by an abnormal accumulation of mast cells in different tissues, mainly in the skin and the bone marrow, but also in spleen, liver, lymph nodes, and the gastrointestinal tract, depending on the nature of the disease, and can be found isolated or sometimes associated with other hematological malignancies in humans. Alterations of the KIT gene have been described in a significant proportion of the patients. Particularly interesting are acquired mutations resulting in a constitutively activated receptor, possibly involved in the increased number of mast cells in tissues. Because of the extreme heterogeneity of mast cell neoplasms, the diseases have been classified into different categories of mastocytosis (See, Metcalfe, J Invest Dermatol. 96:2S-4S (1991)). Mast cells are implicated in tumoral pathologies, particularly in systemic mastocytosises that are hematological diseases similar to myeloproliferative syndromes. Mutant KIT kinase can also be found in mastocytosis associated with other malignant hemopathies, or less frequently in isolated hemopathies such as acute myeloid leukemia and myeloproliferative or myelodysplastic syndromes.

Gain-of-function point mutations of the KIT AL are associated with certain human neoplasms, including systemic mast cell disorders, AML, seminoma and GIST (both primary and imatinib-resistant GIST). In the case of mast cell disorders, seminoma, and AML, the most commonly-associated KIT mutation is the replacement of the normal aspartic acid residue at codon 816 of the activation loop with a valine residue (D816V) (Akin, C. and D. D. Melcalfe, *Ann Rev Med* 55 (2004) 419-32; Longley, B. J. and D. D. Metcalfe, *Hematology-Oncology Clinics of North America* 13. (2000) 697-701; Metcalfe, D. D. and C. Akin, *Leukemia Res* 25 (2001) 577-82; Tefferi, A. and A. Pardanani, *Curr Opin Hematol* 11 (2004) 58-64; Valent, P. et al., *Hematol. Oncol Clin North Am* 17 (2003) 1227-41). The D816V mutation results in constitutive activation of KIT kinase activity and is predicted to help stabilize the AL in the active conformation. In addition to D816V, other mutations involving codon 816 have been reported in systemic mast cell disorders (D816Y, D816F), AML (D816Y) and/or seminomas (D816Y, D816H). Consistent with the structural model of imatinib binding to KIT, the kinase activity of all of these mutants is resistant to imatinib.

In view of the imatinib resistance observed in certain cancers with cells containing certain KIT mutant isoforms, there is a need for diagnostic and therapeutic procedures and compositions tailored to address this condition. Particularly there is a need for a treatment for cancer, mastocytosis and related disorders involving mutant KIT kinase. The invention provided herein satisfies this need.

SUMMARY OF THE INVENTION

BMS-354825 is an ATP-competitive, dual SRC/ABL inhibitor (Lombardo, L. J., et al., J. Med. Chem., 47:6658-6661 (2004)). Notably, BMS-354825 can inhibit BCR-ABL AL mutations that are found in some CML patients with acquired clinical resistance to imatinib. Some small molecule SRC/ABL inhibitors also have potency against KIT kinase. The invention herein is based on the discovery that BMS-354825 inhibits the kinase activity of both wild-type and mutant KIT isoforms, and is therefore a suitable therapy for treating a host suffering from a disease associated with abnormal kinase activity.

The structure and use of BMS-354825 as an anticancer agent is described in Lombardo, L. J., et al., J. Med. Chem., 47:6658-6661 (2004) and is described in the following US patents and pending applications, incorporated herein by reference in their entirety: U.S. Pat. No. 6,596,746, granted Jul. 22, 2003; U.S. patent application Ser. No. 10/395,503, filed Mar. 24, 2003.

As described above, certain mutations in the KIT kinase cause KIT to be resistant to the therapeutic effects of imatinib. Identification of a compound that can inhibit proliferation and/or induce apoptosis of cancer cells that contain such an imatinib resistant KIT mutation is an object of the present invention. Provided herein is such a compound, useful in inhibiting proliferation and/or inducing apoptosis of cell lines that are resistant to treatment with imatinib.

Therefore, the present invention provides compositions, kits and methods for diagnosing and treating a host, preferably human, having or predisposed to a disease associated with abnormal activity of protein kinase. Specifically, the invention provides methods of identifying a mutant KIT kinase in a host having a disease associated with abnormal activity of protein kinase, and tailoring treatment of said host based upon identification of said mutant KIT kinase.

The present invention provides a method for determining the responsiveness of an individual with a protein tyrosine kinase-associated disorder to treatment with 'N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof, wherein said individual has either been previously treated with and developed at least partial resistance to a first kinase inhibitor, or is naïve to treatment with kinase inhibitors, comprising the steps of (a) providing a biological sample from said individual; (b) screening said biological sample for the presence of at least one mutation in a KIT kinase sequence; and (c) assigning the individual to a positive responder group if a mutant KIT kinase is identified. In one embodiment the mutant KIT kinase comprises an amino acid mutation that results in said KIT kinase being constitutively active. In another embodiment the protein tyrosine kinase-associated disorder is selected from the group consisting of mastocytosis and cancer. In a further embodiment the mutant KIT kinase comprises an imatinib resistant KIT mutation. The imatinib resistant KIT mutation may comprises a mutation at amino acid position 816 of SEQ ID NO:2. The mutation can be, e.g., D816Y, D816F, D816V or D816H. In some embodiments, the biological sample is selected from the group consisting of a tissue biopsy, blood, serum, plasma, lymph, ascitic fluid, cystic fluid, urine, sputum, stool, saliva, bronchial aspirate, spinal fluid and hair. The biological sample may be a tissue biopsy cell sample or cells cultured therefrom. In some embodiments the biological sample may comprise blood cells, cells removed from a solid tumor or a lysate of a cell sample.

The present invention provides a method of screening a biological sample, for example cells that do not respond, or that have stopped responding, or that have a diminished response, to kinase inhibitors used to inhibit proliferation of said cells. For example, the present invention provides a method of screening cells from an individual suffering from cancer who is being treated with imatinib, and whose cells do not respond or have stopped responding or that have a diminished response to imatinib, for the presence of KIT mutations described herein. The present invention provides certain KIT mutations that, if present, provide the basis upon which to alter treatment of such individual to inhibit proliferation of said cells.

The present invention provides a method of screening cells that do not respond, or that have stopped responding or that have a diminished response, to kinase inhibitors used to induce apoptosis of said cells. For example, the present invention provides a method of screening cells from an individual suffering from cancer who is being treated with imatinib, and whose cells do not respond or have stopped responding or that have a diminished response to imatinib, for the presence of KIT mutations described herein. The present invention provides certain KIT mutations that, if present, provide the basis upon which to alter treatment of such individual to induce apoptosis of said cells.

The present invention also provides a novel allele-specific PCR-based method for identifying individuals suffering from a disorder caused by a mutant KIT kinase. The method comprises the step of selectively amplifying the mutant KIT kinase from a biological sample of a candidate individual suspected of suffering from the disorder using a primer specific for the mutant sequence and simultaneously using a primer specific for the wild-type KIT sequence. The wild-type KIT-specific primer is designed such that it cannot be extended by PCR.

In one embodiment the method comprises the step of (a) obtaining a biological sample from an individual suspected of suffering from a disorder caused by a mutant KIT kinase, (b) providing a first primer that is specific for a nucleic acid encoding the mutant KIT linase, (c) providing a second primer that is specific for a nucleic acid encoding wildtype KIT kinase, wherein the second primer is modified so as to prevent amplification of the nucleic acid encoding the wild-type KIT kinase, (d) selectively amplifying the nucleic acid encoding the mutant KIT kinase from the biological sample using the first and second primers, and (e) detecting the presence of an amplification product, wherein presence of an amplification product indicates that the individual suffers from a disorder caused by a mutant KIT kinase. In one embodiment, the mutant KIT kinase is an imatinib resistant KIT mutation, or at least partially imatinib resistant. In another embodiment, the mutant KIT kinase is a constitutively active mutant KIT kinase. The mutant KIT kinase may comprise a mutation at amino acid residue 816 of the KIT kinase. Exemplary mutations include, without limitation, D816Y, D816F, D816V, and D816H. In some embodiments the disorder is cancer including, but not limited to, systemic mast disorder, leukemia, seminoma or gastrointestinal stromal tumor.

The present invention provides a method of treating an individual suffering from a protein-kinase-associated disorder, preferably a mutant KIT-associated disorder, comprising administering to said individual a therapeutically effective amount of 'N-(2-chloro-6-methylphenyl)-2-[[6-[4-(2-hydroxyethyl)-1-piperazinyl]-2-methyl-4-pyrimidinyl]amino]-5-thiazole carboxamide (BMS-354825), or a pharmaceutically acceptable salt or hydrate thereof. In one embodiment, the mutant KIT kinase is an imatinib resistant KIT mutation, or at least partially imatinib resistant. In another embodiment, the mutant KIT kinase is a constitutively active mutant KIT kinase. The mutant KIT kinase may comprise a mutation at amino acid residue 816 of the KIT kinase. Exemplary mutations include, without limitation, D816Y, D816F, D816V, and D816H. In some embodiments the method further comprises the administration of a therapeutically effective amount of an mTOR inhibitor. The mTOR inhibitor may be rapamycin.

Also provided is a method of treating a KIT associated disorder, particularly a mutant KIT associated disorder, comprising obtaining a sample of cells from a patient suffering from said disorder, assaying the cells for the presence of a KIT mutation, such as one or more of those described herein, and treating said patient with a compound or treatment regimen to inhibit proliferation and/or induce apoptosis of said cells. In some embodiments the method further comprises the administration of a therapeutically effective amount of an mTOR inhibitor. The mTOR inhibitor may be rapamycin.

The present invention also provides a method of treating an individual suffering from a protein tyrosine kinase associated disorder, comprising the steps of (a) providing a biological sample from the individual; (b) assaying said biological sample for the presence of a mutant KIT kinase; and if a mutant KIT kinase is identified (c) administering a therapeutically effective amount of 'N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof. In some embodiments the mutant KIT kinase comprises a mutation at amino acid position 816 of KIT kinase (SEQ ID NO:2). The mutation at amino acid position 816 of SEQ ID NO:2 may be selected from the group consisting of D816Y, D816F, D816V, and D816H. In some embodiments the method further comprises the administration of a therapeutically effective amount of an mTOR inhibitor. The mTOR inhibitor may be rapamycin.

Also provided is a method of treating an individual suffering from a protein tyrosine kinase associated disorder comprising the steps of (a) providing a biological sample from the individual; (b) assaying said biological sample for at least partial resistance to a first kinase inhibitor; (c) assaying said biological sample for the presence of a mutant KIT kinase; and if said biological sample is determined to be at least partially resistant to said first kinase inhibitor and contains a mutant KIT kinase, then (d) administering a therapeutically effective amount of 'N-(2-chloro-6-methylphenyl)-2-[[6-[4-(2-hydroxyethyl)-1-piperazinyl]-2-methyl-4-pyrimidinyl] amino]-5-thiazolecarboxamide, or a pharmaceutically acceptable salt or hydrate thereof. In some embodiments the first kinase inhibitor is a Bcr-Abl kinase inhibitor. In some embodiments the mutant KIT kinase comprises a mutation at amino acid position 816 of SEQ ID NO:2. The mutation at amino acid position 816 of SEQ ID NO:2 may be selected from the group consisting of D816Y, D816F, D816V, and D816H. In some embodiments the first kinase inhibitor comprises imatinib. In some embodiments the method further comprises the administration of a therapeutically effective amount of an mTOR inhibitor. The mTOR inhibitor may be rapamycin.

The present invention further provides a method of establishing a treatment regimen for an individual suffering from a protein tyrosine kinase associated disorder comprising the steps of (a) providing a biological sample from said individual; (b) screening said biological sample for the presence of at least one mutation in a KIT kinase sequence; and, if at least one mutation in a KIT kinase sequence is present in said biological sample, (c) administering to said individual as part of a treatment regimen a pharmaceutical composition comprising 'N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof. In some embodiments, the at least one mutation comprises a mutation at amino acid position 816 of SEQ ID NO:2. The mutation at amino acid position 816 of SEQ ID NO:2 may be selected from the group consisting of D816Y, D816F, D816V, and D816H. In some embodiments the pharmaceutical composition comprises at least one additional kinase inhibitor. In some embodiments the treatment regimen comprises a therapeutically effective amount of BMS-354825. The biological sample may be a tissue biopsy, blood, serum, plasma, lymph, ascitic fluid, cystic fluid, urine, sputum, stool, saliva, bronchial aspirate, spinal fluid or hair. In some embodiments the biological sample is a tissue biopsy cell sample or cells cultured therefrom. The biological sample may comprise blood cells, cells removed from a solid tumor or a lysate of a cell sample. In some embodiments the method further comprises the administration of a therapeutically effective amount of an mTOR inhibitor. The mTOR inhibitor may be rapamycin.

The present invention also provides a method of establishing a treatment regimen for an individual suffering from a protein tyrosine kinase associated disorder comprising the steps of (a) providing a biological sample from said individual; (b) assaying said biological sample for at least partial resistance to a first kinase inhibitor; (c) assaying said biological sample for the presence of at least one mutation in a KIT kinase sequence; and, if said biological sample is determined to be at least partially resistant to said first kinase inhibitor and contain a mutant KIT kinase, then (d) administering to said individual as part of a treatment regimen a pharmaceutical composition comprising 'N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof. In some embodiments, the at least one mutation comprises a mutation at amino acid position 816 of SEQ ID NO:2. The mutation at amino acid position 816 of SEQ ID NO:2 may be selected from the group consisting of D816Y, D816F, D816V, and D816H. In some embodiments the treatment regimen further comprises administration of at least one additional kinase inhibitor. In some embodiments the method further comprises the administration of a therapeutically effective amount of an mTOR inhibitor. The mTOR inhibitor may be rapamycin.

The present invention also provides a method of treating an individual suffering from a mutant KIT kinase associated disorder comprising the steps of (a) providing a biological sample from said individual; (b) assaying said biological sample for the presence of a mutant KIT kinase, wherein said mutant KIT kinase is constitutively active; and, if a constitutively active mutant KIT kinase is present in said sample, then (c) administering to said individual a pharmaceutical composition comprising 'N-(2-chloro-6-methylphenyl)-2-[[6-[4-(2-hydroxyethyl)-1-piperazinyl]-2-methyl-4-pyrimidinyl] amino]-5-thiazolecarboxamide, or a pharmaceutically acceptable salt or hydrate thereof. In some embodiments the method further comprises the administration of a therapeutically effective amount of an mTOR inhibitor. The mTOR inhibitor may be rapamycin.

The present invention also provides a method of treating an individual suffering from cancer associated with a mutant KIT kinase, comprising administering to said individual a therapeutically effective amount of 'N-(2-chloro-6-methylphenyl)-2-[[6-[4-(2-hydroxyethyl)-1-piperazinyl]-2-methyl-4-pyrimidinyl]amino]-5-thiazole carboxamide (BMS-354825), or a pharmaceutically acceptable or hydrate thereof. In one embodiment, the mutant KIT kinase is an imatinib resistant KIT mutation. In another embodiment, the mutant KIT kinase is a constitutively active mutant KIT kinase. The mutant KIT kinase may comprise a mutation at amino acid residue 816 of the KIT kinase. Exemplary mutations include, without limitation, D816Y, D816F, D816V, and D816H. In some embodiments the cancer is systemic mast disorder, leukemia, seminoma or gastrointestinal stromal tumor. In some embodiments, the individual is or has received administration of a first kinase inhibitor, e.g., imatinib. BMS-354825 may be administered alone or in combination with imatinib or other agents including but not limited to another protein kinase inhibitor, especially a BCR-ABL inhibitor such as $AMN_{107}$, SKI 606, AZD0530, or AP23848 (ARIAD); a tubulin stabilizing agent (e.g., pacitaxol, epothilone, taxane, Taxol, etc.); and a farnysyl transferase (FT) inhibitor (e.g., BMS-214662). In some embodiments, BMS-354825 is administered in combination with a therapeutically effective amount of an mTOR inhibitor.

The invention encompasses a method of treating an individual suffering from cancer, wherein the method comprises assaying cells from said individual to determine the presence of at least one mutation in a KIT kinase protein in said cells, wherein said at least one mutation in a KIT kinase results in said KIT kinase being constitutively activated, and thereby administering to said individual a therapeutically effective amount of BMS-354825. In some embodiments the method further comprises the administration of a therapeutically effective amount of an mTOR inhibitor. The mTOR inhibitor may be rapamycin.

The invention further encompasses a method of treating an individual suffering from cancer, wherein the method comprises assaying cells from said individual to determine the presence of at least one mutation in a KIT kinase protein in said cells, wherein said at least one mutation is selected from the group consisting of D816V, D816F, D816Y, and D816H, and, if said mutation in said KIT protein kinase is identified, administering to said individual a therapeutically effective amount of BMS-354825. In some embodiments the method further comprises the administration of a therapeutically effective amount of an mTOR inhibitor. The mTOR inhibitor may be rapamycin.

The invention further comprises a method of treating an individual suffering from cancer (especially a KIT associated cancer), wherein said individual is or has received administration of a first kinase inhibitor to which the cancer cells in said individual have become resistant or at least partially resistant, comprising assaying cells from said individual to determine the presence of at least one mutation in a KIT kinase protein in said cells, wherein said at least one mutation in a KIT kinase results in said cancer cells being resistant to said first kinase inhibitor, and, if at least one mutation is present in said KIT kinase protein, administering a therapeutically effective amount of BMS-354825 alone or in combination with said first kinase inhibitor. In some embodiments the method further comprises the administration of a therapeutically effective amount of an mTOR inhibitor. The mTOR inhibitor may be rapamycin.

The invention further comprises a method of treating an individual suffering from cancer (especially a KIT associated cancer), wherein said individual is or has received administration of imatinib to which the cancer cells in said individual have become resistant or at least partially resistant, comprising assaying cells from said individual to determine the presence of at least one mutation in a KIT kinase protein in said cells, wherein said at least one mutation in a KIT kinase results in said cancer cells being resistant or at least partially resistant to imatinib, and, if at least one mutation is present in said KIT kinase protein, administering a therapeutically effective amount of BMS-354825 alone or in combination with imatinib or other agents including, but not limited to Taxol or other protein tyrosine kinase inhibitors. Combinations comprising BMS-354825 that may be useful to practice the methods of the present invention are described in U.S. patent application Ser. No. 10/886,955, filed Jul. 8, 2004, U.S. patent application Ser. No. 11/265,843, filed Nov. 3, 2005, and U.S. patent application Ser. No. 11/418,338, filed May 4, 2006, each of which are incorporated herein by reference in its entirety. In some embodiments the method further comprises the administration of a therapeutically effective amount of an mTOR inhibitor. The mTOR inhibitor may be rapamycin.

The invention further comprises a method of treating an individual suffering from cancer, wherein said individual is or has received administration of imatinib to which the cancer cells in said individual have become resistant or at least partially resistant, comprising assaying cells from said individual to determine the presence of at least one mutation in a KIT kinase protein in said cells, wherein said at least one mutation in a KIT kinase results in said cancer cells being resistant to imatinib or at least partially resistant, and, if at least one mutation is present in said KIT kinase protein, administering a therapeutically effective amount of BMS-354825, including an increased or decreased dose (e.g., patients with certain KIT mutations, for example without limitation the D816V or D816F mutation, may require a higher dose of BMS-354825 than patients with wildtype KIT or other KIT mutations), alone or in combination with imatinib or other agents including, but not limited to Taxol or other protein tyrosine kinase inhibitors. Combinations comprising BMS-354825 that may be useful to practice the methods of the present invention are described in U.S. patent application Ser. No. 10/886,955, filed Jul. 8, 2004, U.S. patent application Ser. No. 11/265,843, filed Nov. 3, 2005, and U.S. patent application Ser. No. 11/418,338, filed May 4, 2006, each of which are incorporated herein by reference in its entirety. In some embodiments the method further comprises the administration of a therapeutically effective amount of an mTOR inhibitor. The mTOR inhibitor may be rapamycin.

The invention further comprises a method of treating an individual suffering from cancer (especially a KIT associated cancer), wherein said individual is or has received administration of a first kinase inhibitor to which the cancer cells in said individual have become resistant or at least partially resistant, comprising assaying cells from said individual to determine the presence of at least one mutation in a KIT kinase protein in said cells, wherein said at least one mutation is selected from the group consisting of D816V, D816F, D816Y and D816H, and, if said mutation is present, administering a therapeutically effective amount of BMS-354825 alone or in combination with said first kinase inhibitor. In some embodiments the method further comprises the administration of a therapeutically effective amount of an mTOR inhibitor. The mTOR inhibitor may be rapamycin.

The invention further comprises a method of treating an individual suffering from cancer (especially a KIT associated cancer), wherein said individual is or has received administration of imatinib to which the cancer cells in said individual have become resistant or at least partially resistant, comprising assaying cells from said individual to determine the presence of at least one mutation in a KIT kinase protein in said cells, wherein said at least one mutation is selected from the group consisting of D816V, D816F, D816Y and D816H, and, if said mutation is present, administering a therapeutically effective amount of BMS-354825 alone or in combination with imatinib. In some embodiments the method further comprises the administration of a therapeutically effective amount of an mTOR inhibitor. The mTOR inhibitor may be rapamycin.

The invention encompasses a method of treating an individual suffering from cancer, wherein the method comprises assaying cells from said individual to determine the presence of at least one mutation in a KIT linase protein in said cells, wherein said at least one mutation in a KIT kinase results in said KIT kinase being constitutively activated, and thereby administering to said individual a therapeutically effective amount of BMS-354825 in combination with a therapeutically effective amount of an mTOR inhibitor.

The invention further encompasses a method of treating an individual suffering from cancer, wherein the method comprises assaying cells from said individual to determine the presence of at least one mutation in a KIT kinase protein in said cells, wherein said at least one mutation is selected from the group consisting of D816V, D816F, D816Y, and D816H, and, if said mutation in said KIT protein kinase is identified, administering to said individual a therapeutically effective amount of BMS-354825 in combination with a therapeutically effective amount of an mTOR inhibitor.

The invention further comprises a method of treating an individual suffering from cancer (especially a KIT associated cancer), wherein said individual is or has received administration of a first kinase inhibitor to which the cancer cells in said individual have become resistant or at least partially resistant, comprising assaying cells from said individual to determine the presence of at least one mutation in a KIT kinase protein in said cells, wherein said at least one mutation in a KIT kinase results in said cancer cells being resistant to said first kinase inhibitor, and, if at least one mutation is present in said KIT kinase protein, administering a therapeutically effective amount of BMS-354825 alone or in combination with said first kinase inhibitor, wherein said first kinase inhibitor is a therapeutically effective amount of an mTOR inhibitor.

The invention further comprises a method of treating an individual suffering from cancer (especially a KIT associated cancer), wherein said individual is or has received administration of imatinib to which the cancer cells in said individual have become resistant or at least partially resistant, comprising assaying cells from said individual to determine the presence of at least one mutation in a KIT kinase protein in said cells, wherein said at least one mutation in a KIT kinase results in said cancer cells being resistant or at least partially resistant to imatinib, and, if at least one mutation is present in said KIT kinase protein, administering a therapeutically effective amount of BMS-354825 alone or in combination with imatinib or other agents including, but not limited to Taxol or other protein tyrosine kinase inhibitors or in combination with a therapeutically effective amount of an mTOR inhibitor. Combinations comprising BMS-354825 that may be useful to practice the methods of the present invention are described in U.S. patent application Ser. No. 10/886,955, filed Jul. 8, 2004, U.S. patent application Ser. No. 11/265,843, filed Nov. 3, 2005, and U.S. patent application Ser. No. 11/418,338, filed May 4, 2006, each of which are incorporated herein by reference in its entirety.

The invention further comprises a method of treating an individual suffering from cancer, wherein said individual is or has received administration of imatinib to which the cancer cells in said individual have become resistant or at least partially resistant, comprising assaying cells from said individual to determine the presence of at least one mutation in a KIT kinase protein in said cells, wherein said at least one mutation in a KIT kinase results in said cancer cells being resistant to imatinib or at least partially resistant, and, if at least one mutation is present in said KIT kinase protein, administering a therapeutically effective amount of BMS-354825, including an increased or decreased dose, alone or in combination with imatinib or other agents including, but not limited to Taxol or other protein tyrosine kinase inhibitors or in combination with a therapeutically effective amount of an mTOR inhibitor. Combinations comprising BMS-354825 that may be useful to practice the methods of the present invention are described in U.S. patent application Ser. No. 10/886,955, filed Jul. 8, 2004, U.S. patent application Ser. No. 11/265,843, filed Nov. 3, 2005, and U.S. patent application Ser. No. 11/418,338, filed May 4, 2006, each of which are incorporated herein by reference in its entirety.

The invention further comprises a method of treating an individual suffering from cancer (especially a KIT associated cancer), wherein said individual is or has received administration of a first kinase inhibitor to which the cancer cells in said individual have become resistant or at least partially resistant, comprising assaying cells from said individual to determine the presence of at least one mutation in a KIT kinase protein in said cells, wherein said at least one mutation is selected from the group consisting of D816V, D816F, D816Y and D816H, and, if said mutation is present, administering a therapeutically effective amount of BMS-354825 alone or in combination with said first kinase inhibitor, wherein said first kinase inhibitor is an mTOR inhibitor.

The invention further comprises a method of treating an individual suffering from cancer (especially a KIT associated cancer), wherein said individual is or has received administration of imatinib to which the cancer cells in said individual have become resistant or at least partially resistant, comprising assaying cells from said individual to determine the presence of at least one mutation in a KIT kinase protein in said cells, wherein said at least one mutation is selected from the group consisting of D816V, D816F, D816Y and D816H, and, if said mutation is present, administering a therapeutically effective amount of BMS-354825 alone or in combination with imatinib, and in combination with a therapeutically effective amount of an mTOR inhibitor.

The present invention provides kits for screening and diagnosing disorders associated with aberrant or uncontrolled cellular development and with the expression of a KIT mutant as described herein.

The present invention provides a kit for use in determining treatment strategy for an individual with a protein tyrosine kinase-associated disorder, comprising: (a) a means for detecting a mutant KIT kinase in a biological sample from said patient; and optionally (b) instructions for use and interpretation of the kit results. In some embodiments the kit comprises said instructions and said treatment strategy comprises administration of a therapeutically effective amount of 'N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof. In some embodiments the mutant KIT kinase comprises a mutation at position 816 of SEQ ID NO:2. The mutation at position 816 may be selected from the group consisting of D816V, D816Y, D816F, and D816H. In some embodiments, the kit further comprises a means for obtaining a biological sample from said individual.

Also provided is a kit for use in treating an individual with a mutant KIT kinase associated disorder, comprising: (a) a means for detecting a mutation at amino acid position 816 of a KIT kinase from a biological sample from said individual; (b) a therapeutically effective amount of 'N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof; and (c) instructions for use of said kit. In some embodiments the mutant KIT kinase comprises a mutation at position 816 of SEQ ID NO:2. The mutation at position 816 may be selected from the group consisting of D8S6V, D816Y, D816F, and D816H. In some embodiments, the kit further comprises a means for obtaining a biological sample from said individual.

BRIEF DESCRIPTION OF THE FIGURES

FIG. 1 BMS-354825 potently inhibits kinase activity of the WT KIT cell line M-07e. M-07e cells were treated with varying concentrations of BMS-354825 or imatinib mesylate for 90 minutes before preparation of cellular lysates. Immunoblotting for phosphorylated (PY20 antibody) and total forms of KIT were performed to evaluate the inhibitory effect of BMS-354825 or imatinib mesylate on KIT activation (autophosphorylation) (FIG. 1A). KIT autophosphorylation in these cells is SCF-dependent and BMS-354825 or imatinib inhibits phosphorylation of KIT with $IC_{50s}$, of 1-10 nM (BMS-354825) and 100-1000 nM (imatinib), respectively. (FIG. 1B) M-07e cells were treated with BMS-354825+/− SCF (100 ng/mL) or GM-CSF (100 ng/mL) for 72 h and cellular proliferation was measured using an XTT-based assay. BMS-354825 inhibited the proliferation of SCF-stimulated M-07e cells with an $IC_{50}$ of 5-10 nM, but BMS-354825 doses of 1000 nM had no significant effect on the GM-CSF-dependent growth of these cells. The result of a representative experiment is shown (error bars indicate one standard deviation). The dose-effect plot indicates the computed $IC_{50}$ for the experimental results shown in the bar graph figure.

FIG. 2 BMS-354825 potently inhibits kinase activity of murine KIT D814Y mutation that is homologous to human D814Y. p815 cells were treated with varying concentrations of BMS-354825 or imatinib mesylate as described above. The potency of these agents was evaluated by immunoblotting for phosphorylated and total forms of KIT (FIG. 2A), an XTT-based assay to assess inhibition of cellular proliferation (FIG. 2B), and a flow cytometric assay of apoptosis induction (FIG. 2C). Representative experimental results are shown in FIGS. 2A-2C. The error bars in FIG. 2B indicate one standard deviation. The dose-effect plots indicate the computed $IC_{50}$ for the experimental results shown immediately to the left. BMS-354825 potently inhibits autophosphorylation of KIT and consequently leads to inhibition of cellular proliferation and induction of apoptosis. In contrast, high dose imatinib (1,000 nM) partially inhibited the autophosphorylation of D814Y, but had only a moderate inhibitory effect on cellular proliferation, and does not induce apoptosis in the tested dose range.

FIG. 3 KIT D816V, D816F and D816Y mutations demonstrate differential sensitivity to BMS-354825. Ba/F3 KIT D816V/F/Y cells were treated with varying concentrations of BMS-354825 or imatinib mesylate for 90 minutes. Protein lysates from these cells were immunoprecipitated using an anti-KIT antibody, and/or sequentially immunoblotted using antibodies to phosphorylated tyrosine residues (p-TYR), tyrosine 568/570 and 703-specific p-KIT, or total KIT (FIG. 3A). In panel (FIG. 3B), protein lysates were directly immunoblotted, using antibodies to p-TYR or KIT. (FIG. 3A) BMS-354825 potently inhibits the autophosphorylation of mutant KIT with $IC_{50s}$ of approximately 250-100 nM (D816V), 10-100 nM (D816F), and 1-10 nM (D816Y). As shown for D816V, immunoblotting with the phospho-KIT (Tyr719) antisera or the pan-phosphotyrosyl antibody (PY20) produces identical results. (FIG. 3B) BMS-354825 potently inhibits mutant KIT isoforms in the same dose range as shown in FIG. 2A. In contrast, imatinib mesylate has no significant effect on autophosphorylation of D816V or D816F. However, high-dose imatinib (10,000 nM) does completely inhibit the autophosphorylation of D816Y.

FIG. 8 shows the amino acid sequence of wild type human KIT protein tyrosine kinase (Genbank Accession No. gi|NP_000213; SEQ ID NO:1).

FIG. 9 shows the nucleic acid sequence encoding the amino acid sequence of wild type human KIT protein tyrosine kinase (Genbank Accession No. gi|34084; SEQ ID NO:2).

FIG. 16 shows the sequences of the mutant-specific primer (SEQ ID NO:6) and the blocking primer (SEQ ID NO:7) as compared to wild-type (SEQ ID NO: 10) and mutant KIT sequences D816V and D816F (SEQ ID NO: 8 and SEQ ID NO: 9, respectively). The mutant-specific primer has a single mismatch (indicated by the *) immediately 5' to the 2447 T>A substitution that results in D816V, but is matched to the mutant A and still allows extension. When bound to the wild-type allele, this primer is doubly mismatched at the 3' end and makes a poor substrate for extension. The blocking oligonucleotide is designed with a reverse strategy, such that it has a double mismatch to the mutant allele. In addition, the 3' terminal nucleotide of this oligonucleotide is chemically reversed (3' to 5') so that it cannot serve as a primer (indicated by the $^x$).

FIG. 19 is a table showing the results of AS-PCR using DNA samples from patients known to have mutations at residue 816 in KIT.

FIG. 20A-B is a table comparing the results of AS-PCR, HPLC and sequencing to detect mutations in KIT using DNA samples from patients with clinically suspected cast cell disease.

DETAILED DESCRIPTION OF THE INVENTION

Figure 4:
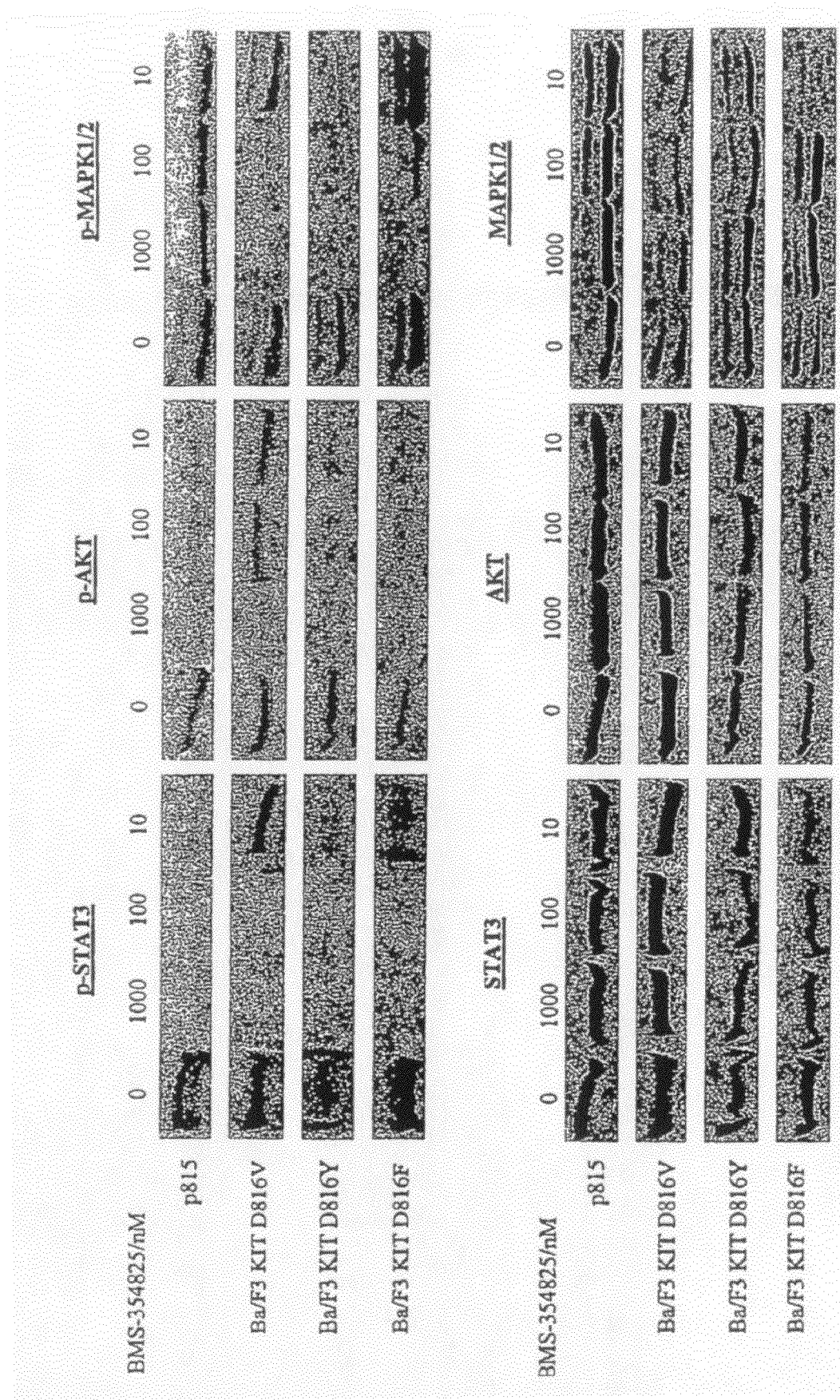
FIG. 4 BMS-354825-mediated inhibition of AL-mutant KIT kinase activity blocks the activation of major downstream pathways. Cell lines expressing KIT AL mutations were treated with varying concentrations of BMS-354825 for 90 minutes before isolation of cellular protein lysates. 200 µg of protein lysate from each cell line was immunoblotted for phosphorylated (p-STAT3, p-AKT and p-MAPK1/2) and total forms of STAT3, AKT and MAPK1/2. Downstream pathways affecting phosphorylation of AKT, STAT3 and MAP kinases are activated in all untreated cell lines. Treatment with BMS-354825 leads to a marked decrease in the concentration of activated forms of STAT3, AKT and MAPK1/2.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., 1989, Molecular Cloning: A Laboratory Manual, 2d ed., Cold Spring Harbor Laboratory Press, Cold Spring Harbor, N.Y. and Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

Throughout this specification and claims, the word "comprise," or variations such as "comprises" or "comprising" will be understood to imply the inclusion of a stated integer or group of integers but not the exclusion of any other integer or group of integers.

As used herein, the term "polynucleotide" means a polymeric form of nucleotides of at least about 10 bases or base pairs in length, either ribonucleotides or deoxynucleotides or a modified form of either type of nucleotide, and is meant to include single and double stranded forms of DNA.

As used herein, the term "polypeptide" means a polymer of at least about 6 amino acids. Throughout the specification, standard three letter or single letter designations for amino acids are used.

As used herein, a polynucleotide is said to be "isolated" when it is substantially separated from contaminant polynucleotides that correspond or are complementary to genes other than, for example, the KIT mutant genes or that encode polypeptides other than KIT mutant gene product or fragments thereof, As used herein, a polypeptide is said to be "isolated" when it is substantially separated from contaminant polypeptide that correspond to polypeptides other than the KIT mutant polypeptides or fragments thereof. A skilled artisan can readily employ polynucleotide or polypeptide isolation procedures to obtain said isolated polynucleotides and/or polypeptides.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37° C. and temperatures for washing in 0.1×SSC/0.1% SDS are above 55° C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", are known to those of skill in the art and as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1× SSC containing EDTA at 55° C.

"Moderately stringent conditions" may be identified as described by Sambrook et al., 1989, Molecular Cloning: A Laboratory Manual, New York: Cold Spring Harbor Press, and include the use of washing solution and hybridization conditions (e.g., temperature, ionic strength and % SDS) less stringent than those described above. A non-limiting example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

For purposes of shorthand designation of the KIT mutant variants described herein, it is noted that numbers refer to the amino acid residue position along the amino acid sequence of the KIT polypeptide. For example, D816 refers to the amino acid aspartic acid at position 816. Amino acid substitutions at a particular position are written as the wild type amino acid, position number, and amino acid substituted therein, in that order. For example, D816V refers to a valine for aspartic acid substitution at position 816. Amino acid identification uses the single-letter alphabet of ammo acids, i.e.,

| Asp | D | Aspartic acid | Ile | I | Isoleucine |
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

In the context of amino acid sequence comparisons, the term "identity" is used to identify and express the percentage of amino acid residues at the same relative positions that are the same. Also in this context, the term "homology" is used to identify and express the percentage of amino acid residues at the same relative positions that are either identical or are similar, using the conserved amino acid criteria of BLAST analysis, as is generally understood in the art. For example, identity and homology values may be generated by WU-BLAST-2 (Altschul et al., Methods in Enzymology, 266: 460-480 (1996): http://blast.wustl/edu/b-last/README-.html).

"Percent (%) amino acid sequence identity" with respect to the sequences identified herein is defined as the percentage of amino acid residues in a candidate sequence that are identical with the amino acid residues in the KIT sequence, after aligning the sequences and introducing gaps, if necessary, to achieve the maximum percent sequence identity. Alignment for purposes of determining percent amino acid sequence identity can be achieved in various ways that are within the skill in the art and can be determined using appropriate parameters for measuring alignment, including assigning algorithms needed to achieve maximal alignment over the full-length sequences being compared.

Those having skill in the art will know how to determine percent identity between/among sequences using, for example, algorithms such as those based on the CLUSTALW computer program (J. D. Thompson et al., 1994, *Nucleic Acids Research*, 2(22):46734680), or FASTDB, (Brutlag et al., 1990, *Comp. App. Biosci.*, 6:237-245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations.

The term "antibody" refers to intact molecules as well as fragments thereof, such as Fab, F(ab')$_2$, Fv, which are capable of binding an epitopic or antigenic determinant. Antibodies that bind to KIT or KIT mutant polypeptides can be prepared using intact polypeptides or fragments containing small peptides of interest, which may be prepared recombinantly for use as the immunizing antigen. The polypeptide or oligopeptide used to immunize an animal can be derived from the transition of RNA or synthesized chemically, and can be conjugated to a carrier protein, if desired. Commonly used carriers that are chemically coupled to peptides include, but are not limited to, bovine serum albumin (BSA), keyhole limpet hemocyanin (KLH), and thyroglobulin. The coupled peptide is then used to immunize the animal (e.g, a mouse, a rat, or a rabbit).

The term "antigenic determinant" refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; each of these regions or structures is referred to as an antigenic determinant. An antigenic determinant may compete with the intact antigen (i.e., the immunogen used to elicit the immune response) for binding to an antibody.

The terms "specific binding" or "specifically binding" refer to the interaction between a protein or peptide and a binding molecule, such as an agonist, an antagonist, or an antibody. The interaction is dependent upon the presence of a particular structure (i.e., an antigenic determinant or epitope) of the protein that is recognized by the binding molecule. For purposes of the present invention compounds, for example small molecules, may be considered for their ability to specifically bind to wild type KIT and/or KIT mutants described herein.

The terms "cancer", "cancerous", or "malignant" refer to or describe the physiological condition in mammals that is typically characterized by unregulated cell growth. Examples of cancer include but are not limited to, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia, and chronic lymphocytic leukemia.

"Protein tyrosine kinase-associated disorders" are those disorders which result from aberrant tyrosine kinase activity, and/or which are alleviated by the inhibition of one or more of these enzymes. Disorders included in the scope of the present invention may include mastocytosis and any symptom associated with mastocytosis. More specifically, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, and mast cell leukemia. Various cancers are also included within the scope of protein tyrosine kinase-associated disorders including (but not limited to) the following: carcinoma, including that of the bladder, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma.

Protein tyrosine kinase-associated disorders of particular interest herein are those disorders which result, at least in part, from aberrant KIT (WT or mutant) activity and/or which are alleviated by the inhibition of KIT (WT or mutant) referred to herein as "KIT associated disorders" or in the case if cancer "KIT associated cancer."

"Mutant KIT kinase" encompasses a KIT kinase with an amino acid sequence that differs from wild type KIT kinase by one or more amino acid substitutions, additions or deletions. For example a substitution of the D816 amino acid with another amino acid would result in a mutant KIT kinase. Encompassed in the present invention are mutant KIT kinases comprising mutations at D816. Amino acid D816 may be substituted with any of the other available amino acids. In one embodiment D816 is substituted with a non-polar, non-acidic amino acid. Discussed herein are several mutant KIT kinases including those with mutations D816V, D816F, D816Y and D816H. KIT necessarily encompasses the v-KIT, c-KIT, KIT, and other forms.

"Mutant KIT kinase associated disorder" is used to describe a protein tyrosine kinase-associated disorder in which the cells involved in said disorder are or become resistant to treatment with a kinase inhibitor used to treat said disorder as a result of a mutation in KIT kinase. As disclosed herein mutations that result in constitutively active KIT kinase are of particular interest. For example, a kinase inhibitor compound may be used to treat a cancerous condition, which compound inhibits the activity of wild type KIT which will inhibit proliferation and/or induce apoptosis of cancerous cells. Over time, a mutation may be introduced into the gene encoding KIT kinase, which may alter the amino acid sequence of KIT kinase and cause the cancer cells to become resistant to treatment with the compound. Alternatively, a mutation may already be present within the gene encoding KIT kinase, either genetically or as a consequence of an oncogenic event, independent of treatment with a protein tyrosine kinase inhibitor, which may be one factor resulting in these cells propensity to differentiate into a cancerous or proliferative state, and also result in these cells being less sensitive to treatment with a protein tyrosine kinase inhibitor. Such situations are expected to result, either directly or indirectly, in a "mutant KIT kinase associated disorder" and treatment of such condition will require a compound that is at least partially effective against the mutant KIT, preferably against both wild type KIT and the mutant KIT. In the instance where an individual develops at least partial resistance to the kinase inhibitor imatinib, the mutant KIT associated disorder is one that results from an imatinib-resistant KIT mutation.

"Imatinib-resistant KIT mutation" refers to a specific mutation in the amino acid sequence of KIT that confers upon cells that express said mutation resistance to treatment with imatinib. As discussed herein such mutations may include mutations at the D816 position of KIT. Contemplated within the invention is a mutation in the KIT sequence selected from the group consisting of D816V, D816Y, D816F and D816H.

"mTOR inhibitor" refers to any molecule capable of inhibiting the expression level and/or activity of mTOR. Non-limiting examples of such molecules are rapamycin (sirolimus), RAD001 (everolimus), temsirolimus (CCI-779), wortmannin, AP23573, PI-103, 13,14-bis(cis-3,5-dimethyl-1-piperazinyl)-beta-elemene (IIi), 13,14-bis[2-(2-thiophenyl)ethylamino]-beta-elemene (IIm), 13,14-bis(cyclohexamino)-beta-elemene (IIn), Clofibrate, and Curcumin in addition to any other mTOR inhibitor known in the art.

The terms "treating", "treatment" and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

Additional definitions are provided throughout the specification.

The invention provides a method of treating cancers, including both primary and metastatic cancers, including solid tumors such as those of the breast, colon, and prostate, as well as lymphomas and leukemias (including CML, AML and ALL), cancers of endothelial tissues, and including cancers which are resistant to other therapies, including other therapies involving administration of kinase inhibitors such as imatinib. Specifically, the invention provides the use of BMS-354825 for treating disorders, for example cancers, which are resistant to other therapies involving administration of kinase inhibitors such as imatinib.

The invention provides that BMS-354825, both as monotherapy and in combination therapies, will be useful against cancers which are resistant to one or more other anticancer agents, including among others cancers which are resistant in whole or part to other anticancer agents, specifically including imatinib and other kinase inhibitors, and specifically including cancers involving one or more mutations in KIT kinase.

The invention also contemplates a method for identifying an individual for treatment comprising screening cells from an individual to identify a mutant KIT kinase expressed in said cells, and if a mutant KIT mutant kinase is present, administering a therapeutically effective amount of an inhibitor of said mutant KIT kinase, or an increased therapeutically effective amount of an inhibitor of said mutant KIT kinase. According to the present invention the identification of a mutation at the D816 position of KIT kinase would indicate an individual selected for treatment. Included within the invention is a D816 mutation selected from the group consisting of D816V, D816Y, D816F and D816H.

Methods of identifying the amino acid and nucleic acid of a mutant KIT kinase are known in the art. Standard molecular biology techniques are contemplated for precisely determining a KIT mutation in the cells of a given individual.

Antibodies that immunospecifically bind to a mutant KIT kinase may be used in identifying one or more of the KIT mutants described herein. Contemplated herein are antibodies that specifically bind to a mutant KIT kinase and that do not bind (or bind weakly) to wild type KIT protein or polypeptides. Anti-mutant KIT kinase antibodies include monoclonal and polyclonal antibodies as well as fragments containing the antigen binding domain and/or one or more complementarity determining regions of these antibodies.

For some applications, it may be desirable to generate antibodies which specifically react with a particular mutant KIT kinase protein and/or an epitope within a particular structural domain. For example, preferred antibodies useful for diagnostic purposes are those which react with an epitope in a mutated region of the KIT protein as expressed in cancer cells. For example, antibodies that bind specifically to a D816V, D816Y, D816F or D816H mutant KIT kinase. Such antibodies may be generated by using the mutant KIT kinase protein described herein, or using peptides derived from various domains thereof, as an immunogen.

Mutant KIT kinase antibodies of the invention may be particularly useful in cancer (e.g., GIST, chronic myclogenous leukemia) therapeutic strategies, diagnostic and prognostic assays, and imaging methodologies. Similarly, such antibodies may be useful in the diagnosis, and/or prognosis of other cancers, to the extent such mutant KIT kinase is also expressed or overexpressed in other types of cancer. The invention provides various immunological assays useful for the detection and quantification of mutant KIT kinase proteins and polypeptides. Such assays generally comprise one or more mutant KIT kinase antibodies capable of recognizing and binding a mutant KIT kinase protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancer cells are also provided by the invention, including but limited to imaging methods using labeled mutant KIT kinase antibodies. Such assays may be used clinically in the detection, monitoring, and prognosis of cancers.

Another aspect of the present invention relates to methods for detecting mutant KIT kinase polynucleotides and mutant KIT kinase proteins, as well as methods for identifying a cell that expresses mutant KIT kinase. The expression profile of mutant KIT kinases makes them diagnostic markers for disease states. The status of mutant KIT kinase gene products in patient samples may be analyzed by a variety protocols that are well known in the art including the following non-limiting types of assays: PCR-free genotyping methods, Single-step homogeneous methods, Homogeneous detection with fluorescence polarization, Pyrosequencing, "Tag" based DNA chip system, Bead-based methods, fluorescent dye chemistry, Mass spectrometry based genotyping assays, TaqMan genotype assays, Invader genotype assays, microfluidic genotype assays, immunohistochemical analysis, the variety of Northern blotting techniques including in situ hybridization, RT-PCR analysis (for example on laser capture micro-dissected samples), western blot analysis, tissue array analysis, and any other methods known in the art or described elsewhere herein.

Determining the KIT gene mutation status in cases of AML is relatively straightforward, as tumor cells typically dominate blood, bone marrow aspirate and bone marrow biopsy samples. In contrast, mutation analysis in mastocytosis presents a greater challenge. The degree of mast cell infiltration in affected organs varies widely and may represent as little as 1% of the cell population in a given biopsy. In patients with GISTs, denaturing HPLC has been used to screen for KIT gene mutations with a sensitivity of approximately 10-20% mutant allele. Methods used to detect KIT mutations in patients with suspected SM include cDNA amplification and sequencing, analyses of genomic DNA by direct sequencing, RPLP and SSCP, and real-time PCR using peptide-nucleic acid probes, in addition to other methods disclosed herein or otherwise known in the art.

The present invention provides highly sensitive methods for detecting mutations in KIT using a PCR-based assay. This allele-specific PCR (AS-PCR) assay is based on using a combination of a mutation-directed primer and a wild-type blocking oligonucleotide, and can reproducibly detect either KIT D816V or D816F present at low levels in DNA extracted from paraffin-embedded tissue.

The sensitivity of the AS-PCR assay may be increased by suppressing the amplification of the corresponding wild-type allele. For example, a restriction endonuclease can be used to cleave wild-type sequence prior to amplification, if an appropriate site is available. Alternatively, a blocking oligonucleotide can be used to prevent priming or elongation of a target sequence. A blocking oligonucleotide constructed of locked nucleic acids can substantially suppress the amplification of wild-type sequence in an assay employing Stoffel-fragment polymerase. This approach may prove useful when several mutations of interest occur in a given exon.

Specifically encompassed by the present invention are the following, non-limiting genotyping methods: Landegren, U., Nilsson, M. & Kwok, P. Genome Res 8, 769-776 (1998); Kwok, P., Pharmacogenomics 1, 95-100 (2000); Gut, I., Hum Mutat 17, 475-492 (2001); Whitecombe, D., Newton, C. & Little, S., Curr Opin Biotechnol 9, 602-608 (1998); Tillib, S. & Mirzabekov, A., Curr Opin Biotechnol 12, 53-58 (2001); Winzeler, E. et al., Science 281, 1194-1197 (1998); Lyamichev, V. et al., Nat Biotechnol 17, 292-296 (1999); Hall, J. et al., Proc Natl Acad Sci USA 97, 8272-8277 (2000); Mein, C. et al., Genome Res 10, 333-343 (2000); Ohnishi, Y. et al., J Hum Genet 46, 471-477 (2001); Nilsson, M. et al., Science 265, 2085-2088 (1994); Baner, J., Nilsson, M., Mendel-Hartvig, M. & Landegren, U., Nucleic Acids Res 26, 5073-5078 (1998); Baner, J. et al., Curr Opin Biotechnol 12, 11-15 (2001); Hatch, A., Sano, T., Misasi, J. & Smith, C., Genet Anal 15, 35-40 (1999); Lizardi, P. et al., Nat Genet 19, 225-232 (1998); Zhong, X., Lizardi, P., Huang, X., Bray-Ward, P. & Ward, D., Proc Natl Acad Sci USA 98, 3940-3945 (2001); Faruqi, F. et al. BMC Genomics 2, 4 (2001); Livak, K., Genet Anal 14, 143-149 (1999); Marras, S., Kramer, F. & Tyagi, S., Genet Anal 14, 151-156 (1999); Ranade, K. et al., Genome Res 11, 1262-1268 (2001); Myakishev, M., Khripin, Y., Hu, S. & Hamer, D., Genome Re 11, 163-169 (2001); Beaudet, L., Bedard, J., Breton, B., Mercuri, P, & Budarf, M., Genome Res 11, 600-608 (2001); Chen, X., Levine, L. & PY, K., Genome Res 9, 492-498 (1999); Gibson, N. et al., Clin Chem 43, 1336-1341 (1997); Latif, S., Bauer-Sardina, I., Ranade, K., Livak, K. & PY, K., Genome Res 11, 436-440 (2001); Hsu, T., Law, S., Duan, S., Neri, B. & Kwok, P., Clin Chem 47, 1373-1377 (2001); Alderbom, A., Kristofferson, A. & Hammerling, U., Genome Res 10, 1249-1258 (2000); Ronaghi, M., Uhlen, M. & Nyren, P., Science 281, 363, 365 (1998); Ronaghi, M., Genome Res 11, 3-11 (2001); Pease, A. et al., Proc Natl Acad Sci USA 91, 5022-5026 (1994); Southern, E., Maskos, U. & Elder, J., Genomics 13, 1008-1017 (1993); Wang, D. et al., Science 280, 1077-1082 (1998); Brown, P. & Botstein, D., Nat Genet 21, 33-37 (1999); Cargill, M. et al. Nat Genet 22, 231-238 (1999); Dong, S. et al., Genome Res 11, 1418-1424 (2001); Halushka, M. et al., Nat Genet 22, 239-247 (1999); Hacia, J., Nat Genet 21, 42-47 (1999); Lipshutz, R., Fodor, S., Gingeras, T. & Lockhart, D., Nat Genet 21, 20-24 (1999); Sapolsky, R. et al., Genet Anal 14, 187-192 (1999); Tsuchihashi, Z. & Brown, P., J Virol 68, 5863 (1994); Herschlag, D., J Biol Chem 270, 20871-20874 (1995); Head, S. et al., Nucleic Acids Res 25, 5065-5071 (1997); Nikiforov, T. et al., Nucleic Acids Res 22, 41674175 (1994); Syvanen, A. et al., Genomics 12, 590-595 (1992); Shumaker, J., Metspalu, A. & Caskey, C., Hum Mutat 7, 346-354 (1996); Lindroos, K., Liljedahl, U., Raitio, M. & Syvanen, A., Nucleic Acids Res 29, E69-9 (2001); Lindblad-Toh, K. et al., Nat Genet 24, 381-386 (2000); Pastinen, T. et al., Genome Res 10, 1031-1042 (2000); Fan, J. et al., Genome Res 10, 853-860 (2000); Hirschhorn, J. et al., Proc Natl Acad Sci USA 97, 12164-12169 (2000); Bouchie, A., Nat Biotechnol 19, 704 (2001); Hensel, M. et al., Science 269, 400-403 (1995); Shoemaker, D., Lashkari, D., Morris, D., Mittmann, M. & Davis, R. Nat Genet 14, 450-456 (1996); Gerry, N. et al., J Mol Biol 292, 251-262 (1999); Ladner, D. et al., Lab Invest 81, 1079-1086 (2001); Iannone, M. et al. Cytometry 39, 131-140 (2000); Fulton, R., McDade, R., Smith, P., Kienker, L. & Kettman, J. J., Clin Chem 43, 1749-1756 (1997); Armstrong, B., Stewart, M. & Mazumder, A., Cytometry 40, 102-108 (2000); Cai, H. et al., Genomics 69, 395 (2000); Chen, J. et al., Genome Res 10, 549-557 (2000); Ye, F. et al. Hum Mutat 17, 305-316 (2001); Michael, K., Taylor, L., Schultz, S. & Walt, D., Anal Chem 70, 1242-1248 (1998); Steemers, F., Ferguson, J. & Walt, D., Nat Biotechnol 18, 91-94 (2000); Chan, W. & Nie, S., Science 281, 2016-2018 (1998); Han, M., Gao, X., Su, J. & Nie, S., Nat Biotechnol 19, 631-635 (2001); Griffin, T. & Smith, L., Trends Biotechnol 18, 77-84 (2000); Jackson, P., Scholl, P. & Groopman, J., Mol Med Today 6, 271-276 (2000); Haff, L. & Smirnov, I., Genome Res 7, 378-388 (1997); Ross, P., Hall, L., Smirnov, I. & Haff, L., Nat Biotechnol 16, 1347-1351 (1998); Bray, M., Boerwinkle, E. & Doris, P. Hum Mutat 17, 296-304 (2001); Sauer, S. et al., Nucleic Acids Res 28, E13 (2000); Sauer, S. et al., Nucleic Acids Res 28, E100 (2000); Sun, X., Ding, H., Hung, K. & Guo, B., Nucleic Acids Res 28, E68 (2000); Tang, K. et al., Proc Natl Acad Sci USA 91, 10016-10020 (1999); Li, J. et al., Electrophoresis 20, 1258-1265 (1999); Little, D., Braun, A., O'Donnell, M. & Koster, H., Nat Med 3, 1413-1416 (1997); Little, D. et al. Anal Chem 69, 4540-4546 (1997); Griffin, T., Tang, W. & Smith, L., Nat Biotechnol 15, 1368-1372 (1997); Ross, P., Lee, K. & Belgrader, P., Anal Chem 69, 4197-4202 (1997); Jiang-Baucom, P., Girard, J., Butler, J. & Belgrader, P., Anal Chem 69, 489-44898 (1997); Griffin, T., Hall, J., Prudent, J. & Smith, L., Proc Natl Acad Sci USA 96, 6301-6306 (1999); Kokoris, M. et al., Mol Diagn 5, 329-340 (2000); Jurinke, C., van den Boom, D., Cantor, C. & Koster, H. (2001); and/or Taranenko, N. et al., Genet Anal 13, 87-94 (1996).

The following additional genotyping methods are also encompassed by the present invention: the methods described and/or claimed in U.S. Pat. No. 6,458,540; and the methods described and/or claimed in U.S. Pat. No. 6,440,707.

Probes and primers can be designed so as to be specific to such mutation analysis and are derived from the wild type KIT sequence, segments and complementary sequences thereof.

Additionally, the invention provides assays for the detection of mutant KIT kinase polynucleotides in a biological sample, such as cell preparations, and the like. A number of methods for amplifying and/or detecting the presence of mutant KIT kinase polynucleotides are well known in the art and may be employed in the practice of this aspect of the invention.

In one embodiment, a method for detecting a mutant KIT kinase mRNA in a biological sample comprises producing cDNA from the sample by reverse transcription using at least one primer; amplifying the cDNA so produced using mutant KIT kinase polynucleotides as sense and antisense primers to amplify mutant KIT kinase cDNAs therein; and detecting the presence of the amplified mutant KIT kinase cDNA. Any number of appropriate sense and antisense probe combinations may be designed from the nucleotide sequences provided for a mutant KIT kinase and used for this purpose.

The invention also provides assays for detecting the presence of a mutant KIT kinase protein in a biological sample. Methods for detecting a mutant KIT kinase protein are also well known and include, for example, immunoprecipitation, immunohistochemical analysis, Western Blot analysis, molecular binding assays, ELISA, ELIFA and the like. For example, in one embodiment, a method of detecting the presence of a mutant KIT kinase protein in a biological sample comprises first contacting the sample with a KIT antibody, a mutant KIT kinase-reactive fragment thereof, or a recombinant protein containing an antigen binding region of a mutant KIT kinase antibody, and then detecting the binding of mutant KIT kinase protein in the sample thereto.

Methods for identifying a cell that expresses mutant KIT kinase are also provided. In one embodiment, an assay for identifying a cell that expresses a mutant KIT kinase gene comprises detecting the presence of mutant KIT kinase mRNA in the cell. Methods for the detection of particular mRNAs in cells are well known and include, for example, hybridization assays using complementary DNA probes (such as in situ hybridization using labeled mutant KIT kinase riboprobes, Northern blot and related techniques) and various nucleic acid amplification assays (such as RT-PCR using complementary primers specific for a mutant KIT kinase, and other amplification type detection methods, such as, for example, branched DNA, SISBA, TMA and the like).

The invention encompasses treatment methods based upon the discovery that certain mutant KIT kinases that confer some level of resistance to kinase inhibitors such as imatinib are sensitive to BMS-354825. Thus the methods of the present invention can be used in determining whether or not to treat an individual with a specific tyrosine kinase inhibitor, such as BMS-354825. One embodiment of the invention is a method of identifying a mutation in a KIT polynucleotide in a mammalian cell, wherein the mutation in a KIT polynucleotide is associated with resistance to inhibition of KIT kinase activity by imatinib, the method comprising determining the sequence of at least one KIT polynucleotide expressed by the mammalian cell and comparing the sequence of the KIT polynucleotide to the wild type KIT polynucleotide sequence. As described herein the polynucleotide identified may encode a polynucleotide having at least one amino acid difference from the wild type KIT amino acid sequence.

Treatment regimens may be established based upon the presence of one or more mutant KIT kinases disclosed herein. For example, the invention encompasses screening cells from an individual who may suffer from, or is suffering from, a disorder that is commonly treated with a kinase inhibitor. Such a disorder may include mastocytosis or disorders associated therewith, or cancers described herein. The cells of an individual are screened, using methods known in the art, for identification of a mutation in a KIT kinase. Mutations of interest are those that result in KIT kinase being constitutively activated. Specific mutations include D816V (where the aspartic acid at position 816 is replaced with a valine), D816F (wherein the aspartic acid at position 816 is replaced with a phenylalanine), D816Y (wherein the aspartic acid at position 816 is replaced with a tyrosine), and D816H (wherein the aspartic acid at position 816 is replaced with a histidine).

If an activating KIT kinase mutation is found in the cells from said individual, treatment regimens can be developed appropriately. For example, an identified mutation may indicate that said cells are or will become resistant to commonly used kinase inhibitors. Such an inhibitor includes the kinase inhibitor imatinib. If the cells in an individual are or are expected to become resistant to treatment with a kinase inhibitor such as imatinib, then, as disclosed herein, treatment should include the use of BMS-354825. BMS-354825 can be administered alone or, since for a given disease such as GIST, an individual may present with cells expressing WT KIT as well as cells expressing one or more mutant KIT kinases, in combination with other kinase inhibitors such as imatinib, as well as with other agents suitable for treating the disorder.

Additionally, dosage regimens may be established based upon the presence of a specific amino acid mutation in a KIT kinase. As disclosed herein, a specific amino acid mutation in KIT kinase may make said mutant KIT kinase more sensitive to treatment with a kinase inhibitor that another amino acid substitution. As described, cells exhibiting the D816Y mutant KIT kinase are more sensitive to treatment with BMS-354825 than cells that exhibit the D816V or D816F mutant KIT kinase. This discovery is useful in determining the dosage regimen for an individual whose cells exhibit such a mutation. For example, a lower dosage of inhibitor BMS-354825 may be employed if cells exhibit a D816Y mutant KIT kinase; alternatively a higher dosage of inhibitor BMS-354825 may be employed if cells exhibit a D816V or D816F mutant kinase. In one embodiment, an increased or decreased level of dasatinib would be about 10, 20, 30, 40, 50, 60, 70, 80, 90, or 95% more than the typical dasatinib dose for a particular indication or for individual, or about 1.5×, 2×, 2.5×, 3×, 3.5×, 4×, 4.5×, or 5× more dasatinib than the typical dasatinib dose for a particular indication or for individual.

A therapeutically effective amount of Compound I can be orally administered as an acid salt or hydrate of Compound I. The actual dosage employed may be varied depending upon the requirements of the patient and the severity of the condition being treated. Determination of the proper dosage for a particular situation is within the skill of the art. The effective amount of Compound I (and Compound I salt or hydrate) may be determined by one of ordinary skill in the art, and includes exemplary dosage amounts for an adult human of from about 0.05 to about 100 mg/kg of body weight of Compound I per day, which may be administered in a single dose or in the form of individual divided doses, such as from 1, 2, 3, or 4 times per day. In one embodiment, Compound I is administered 2 times per day at 70 mg. Alternatively, it may be dosed at 50, 70, 90, 100, 110, or 120 BID, or 100, 140, or 180 once daily. It will be understood that the specific dose level and frequency of dosing for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, and the like, subject to protein tyrosine kinase-associated disorders.

In the method disclosed above, the mammalian cell may be a human cancer cell. The human cancer cell may be one obtained from an individual treated with imatinib. Optionally the amino acid substitution in the KIT polypeptide expressed in said human cancer cell confers resistance to inhibition of tyrosine kinase activity by imatinib.

A method of determining the responsiveness of an individual suffering from a protein tyrosine kinase-associated disorder to a kinase inhibitor, such as BMS-354825, is also disclosed herein. For example, an individual may be determined to be a positive responder (or cells from said individual would be expected to have a degree of sensitivity) to a certain kinase inhibitor based upon the presence of a mutant KIT kinase. As disclosed herein, cells that exhibit certain mutations at amino acid position 816 of KIT kinase develop resistance to imatinib. Therefore, individuals suffering from a protein tyrosine kinase-associated disorder whose cells exhibit such a mutation are or would be expected to be negative responders to treatment with imatinib. The present discovery established for the first time that cells with a mutation at amino acid position 816 in KIT kinase that confers resistance to imatinib are sensitive to BMS-354825. Therefore, an individual whose cells exhibit a mutant KIT kinase as disclosed herein may be identified as a positive responder to BMS-354825 in spite of a negative response to imatinib. Treatment regimens are then established for such individuals accordingly.

Treatment regimens based upon the presence of a mutant KIT kinase are also provided herein. A treatment regimen is a course of therapy administered to an individual suffering from a protein kinase associated disorder that may include treatment with one or more kinase inhibitors, as well as other therapies such as radiation and/or other agents. When more than one therapy is administered, the therapies may be administered concurrently or consecutively (for example, more than one kinase inhibitor may be administered together or at different times, on a different schedule). Administration of more than one therapy may be at different times (i.e., consecutively) and still be part of the same treatment regimen. As disclosed herein, for example, cells from an individual suffering from a protein kinase associated disorder may be found to develop resistance to imatinib. Based upon the present discovery that such cells may be sensitive to BMS-354825 a treatment regiment can be established that includes treatment with BMS-354825 either as a monotherapy, or in combination with imatinib or another kinase inhibitor. Additionally, BMS-354825 can be administered with radiation or other known treatments.

Therefore the present invention includes a method for establishing a treatment regimen for an individual suffering from a protein tyrosine kinase associated disorder comprising: (a) providing a sample of cells from said individual; (b) screening said sample of cells for the presence of at least one mutation in a KIT kinase sequence; and, if at least one mutation in a KIT kinase sequence is present in said sample of cells, (c) administering to said individual as part of a treatment regimen a pharmaceutical composition comprising BMS-354825. When screening the cells from an individual suffering from a protein kinase associated disorder one may look for a mutation in the nucleic acid sequence encoding KIT kinase, or for a resulting mutation in the amino acid sequence of KIT kinase.

Wherever the term "BMS-354825" is used herein, it is understood (unless otherwise indicated) that the compound 'N-(2-chloro-6-methylphenyl)-2-[[6-[4-(2-hydroxyethyl)-1-piperazinyl]-2-methyl-4-pyrimidinyl]amino]-5-thiazolecarboxamide having the following structure (I):

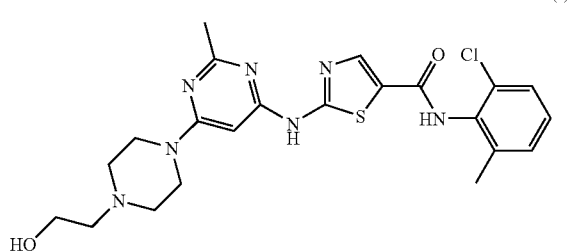

(I)

is intended, as well as all pharmaceutically acceptable salts or hydrates thereof. Compound (I) is also referred to as N-(2-chloro-6-methylphenyl)-2-((6-(4-(2-hydroxyethyl)-1-piperazinyl)-2-methyl-4-pyrimidinyl)amino)-1,3-thiazole-5-carboxamide in accordance with IUPAC nomenclature. Use of the term encompasses (unless otherwise indicated) solvates (including hydrates) and polymorphic forms of the compound (I) or its salts or hydrates (such as the monohydrate form of (I) described in U.S. patent application Ser. No. 11/051,208, filed Feb. 4, 2005, incorporated herein by reference in its entirety). Pharmaceutical compositions of BMS-354825 include all pharmaceutically acceptable compositions comprising BMS-354825 and one or more diluents, vehicles and/or excipients, such as those compositions described in U.S. patent application Ser. No. 11/402,502, filed Apr. 12, 2006, incorporated herein by reference in its entirety.

Wherein the term "a farnysyl transferase inhibitor (e.g., BMS-214662)" herein, it is understood (unless otherwise indicated) that the compound have formula (II), (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, hydrochloride salt, is an anti-cancer agent. The compound of formula (II) is a cytotoxic FT inhibitor which is known to kill non-proliferating cancer cells preferentially. The compound of formula (II) may further be useful in killing stem cells.

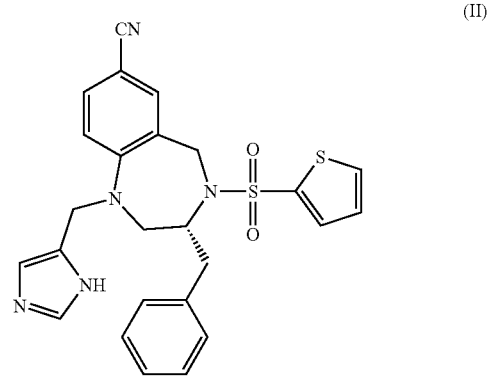

(II)

The compound of formula (II), its preparation, and uses thereof are described in U.S. Pat. No. 6,011,029, which is herein incorporated by reference in its entirety. The uses of the compound of formula (II) are also described in WO2004/015130, published Feb. 19, 2004, which is herein incorporated by reference in its entirety.

In practicing the many aspects of the invention herein, biological samples may be selected from many sources such as tissue biopsy (including cell sample or cells cultured therefrom; biopsy of bone marrow or solid tissue, for example cells from a solid tumor), blood, blood cells (red blood cells or white blood cells), serum, plasma, lymph, ascetic fluid, cystic fluid, urine, sputum, stool, saliva, bronchial aspirate, CSF or hair. Cells from a sample may be used, or a lysate of a cell sample may be used.

Analysis of the expression of a mutant KIT kinase described herein may also be useful as a tool for identifying and evaluating agents that modulate expression of a nucleic acid sequence encoding mutant KIT kinase, for example, an antisense or sRNAi polynucleotide that would block expression of mutant KIT kinase. Identification of a molecule of biologic agent that could inhibit mutant KIT kinase activity is of therapeutic value. An agent that specifically binds to a nucleic acid sequence encoding a polypeptide comprising amino acid 816 of KIT, wherein amino acid 816 comprises a mutation selected from the group consisting of D816V, D816Y, D816F and D816H is of therapeutic value.

Pharmaceutical compositions for use in the present invention include compositions comprising an inhibitor of a mutant KIT kinase in an effective amount to achieve the intended purpose. The determination of an effective dose of a pharmaceutical composition of the invention is well within the capability of those skilled in the art. A therapeutically effective dose refers to that amount of active ingredient which ameliorates the symptoms or condition. Therapeutic efficacy and toxicity may be determined by standard pharmaceutical procedures in cell cultures or experimental animals, for example the ED50 (the dose therapeutically effective in 50% of the population) and LD50 (the dose lethal to 50% of the population).

Dosage regimens involving BMS-354825 useful in practicing the present invention are described in U.S. patent application Ser. No. 10/395,503, filed Mar. 24, 2003; and *Blood* (ASH Annual Meeting Abstracts) 2004, Volume 104: Abstract 20, "Hematologic and Cytogenetic Responses in Imatinib-Resistant Accelerated and Blast Phase Chronic Myeloid Leukemia (CML) Patients Treated with the Dual SRC/ABL Kinase Inhibitor BMS-354825: Results from a Phase I Dose Escalation Study.", by Moshe Talpaz, et al; which are hereby incorporated herein by reference in its entirety.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

A "therapeutically effective amount" of an inhibitor of a mutant KIT kinase may be a function of the mutation present. For example the present invention discloses cell lines with certain mutations in KIT kinase are more sensitive to BMS-354825 than cell lines with different KU kinase mutations. As disclosed herein, cells comprising a D816Y mutation in KIT kinase are ten-fold more sensitive to BMS-354825 than cell lines expressing a D816V mutation. Therefore a therapeutically effective amount of BMS-354825 when treating an individual with cells that express a D816Y KIT mutation may be lower than a therapeutically effective amount of BMS-354825 when treating an individual with cells that express a D816V KIT mutation. Once skilled in the art will appreciate the difference in sensitivity of the mutant KIT kinase cells and determine a therapeutically effective dose accordingly.

The present invention provides a method of treating an individual suffering from a protein-kinase-associated disorder, preferably a mutant KIT-associated disorder, e.g., a mutant KIT-associated cancer, comprising administering to said individual a therapeutically effective amount of 'N-(2-chloro-6-methylphenyl)-2-[[6-[4-(2-hydroxyethyl)-1-piperazinyl]-2-methyl-4-pyrimidinyl]amino]-5-thiazole carboxamide, or a pharmaceutically acceptable salt or hydrate thereof. In one embodiment, the mutant KIT kinase is an imatinib resistant KIT mutation. In another embodiment, the mutant KIT kinase is a constitutively active mutant KIT kinase. The mutant KIT kinase may comprise a mutation at amino acid residue 816 of the KIT kinase. Exemplary mutations include, without limitation, D816Y, D816F, D816V, and D816H.

In one embodiment the cancer is systemic mast disorder, leukemia, seminoma or gastrointestinal stromal tumor. In some embodiments, the individual is or has received administration of a first kinase inhibitor, e.g., imatinib. BMS-354825 may be administered alone or in combination with imatinib or another protein kinase inhibitor, especially a BCR-ABL inhibitor such AMN107, SKI 606, AZDO530, or AP23848 (ARIAD); and/or a tubulin stabilizing agent, (e.g., pacitaxol, epothilone, taxane, Taxol, etc.), and/or in combination with a farnysyl transferase inhibitor (e.g., BMS-214662). In some embodiments, BMS-354825 is administered in combination with a therapeutically effective amount of an mTOR inhibitor.

Therefore, the present invention provides a method of treating an individual suffering from a protein tyrosine kinase-associated disorder (where such individual is naïve to treatment with a kinase inhibitor (i.e., has not previously been treated with such) or has been treated with one or more kinase inhibitors (for example, has been treated with imatnib)), such as a KIT associated disorder (for example, a KIT-associated cancer), comprising: (a) providing a biological sample from said individual (whether as-is or manipulated (such as lysed), for example, to facilitate assaying); (b) assaying said biological sample for the presence of one or more mutant KIT kinase(s); and, based on the results of said assay, such as where one or more mutant KIT kinase(s) is(are) present in said sample, then (c) administering to said individual BMS-354825, preferably as an active agent in a pharmaceutical composition, alone, or in combination with another kinase inhibitor and/or with another agent suitable for the treatment of said protein tyrosine kinase-associated disorder, said other kinase inhibitor and/or other agent being administered simultaneously or sequentially with the administration of BMS-354825) wherein, for example, and without limitation:

(1) identification of at least one mutant KIT kinase which is at least partially sensitive to inhibition with BMS-354825 may optionally be used to select treatment with BMS-354825 preferentially to other kinase inhibitor(s) (for example, where it is expected that BMS-354825 will be effective against said mutant at therapeutically useful doses better tolerated by patients than doses of such other kinase inhibitor(s));

(2) identification of at least one mutant KIT kinase may optionally be used to select the dose of BMS-354825, including increasing or decreasing the dose thereof (either for individuals naïve to BMS-354825 or those undergoing treatment with BMS-354825), for example, where the mutant KIT kinase is inhibited by BMS-354825 to a lesser or greater degree, respectively, relative to WT KIT kinase; and/or (3) identification of at least one mutant KIT kinase may optionally be used to select co-administration of another agent suitable for treatment of said protein tyrosine kinase-associated disorder (including another kinase inhibitor such as imatinib) with BMS-354825, for example, where such agent is at least partially effective in inhibiting said mutant KIT kinase.

Rational drug design screening methods are also encompassed by the present invention. With the discovery that BMS-354825 is an effective inhibitor of imatinib resistant mutant KIT kinases, one skilled in the art will be able to design compounds in the context of a crystal structure of a mutant KIT kinase bound to BMS-354825. This definition of the crystal structure allows one skilled in the art to evaluate the conformation of a mutant KIT kinase and the amino acid residues or domains critical to compound binding and activity. Thus the present invention provides the basis for a variety of comparative analyses as well as rational drug design.

In this regard, the invention contemplates a method for treating a mammal suffering from a mutant KIT associated disorder comprising administering to a mammal in need of such treatment a compound that is a selective and potent inhibitor of a mutant KIT kinase obtainable by a screening method which comprises: (1) bringing a mutant KIT kinase into contact with BMS-354825 under conditions that allow the mutant KIT kinase to form a complex with BMS-354825, (2) resolving the crystal structure of the mutant KIT kinase/BMS-354825 complex to identify a binding domain, (3) designing compounds expected to fit within an identified binding domain, and (4) testing said designed compounds for activity in inhibiting said mutant KIT kinase.

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a mutant KIT kinase protein or a mutant KIT kinase gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

Kits useful in practicing therapeutic methods disclosed herein may also contain a compound that is capable of inhibiting a mutant KIT kinase. Specifically contemplated by the invention is a kit comprising BMS-354825 useful in treating mammals suffering from a mutant KIT associated disorder. For example, kits useful in identifying a mutant KIT kinase in a mammalian patient (e.g., a human) suffering from a cancer that is resistant to, or has developed resistance to, imatinib and where said kits also comprise a therapeutically effective amount of BMS-354825 are contemplated herein.

The following representative examples contain important additional information, exemplification and guidance which can be adapted to the practice of this invention in its various embodiments and the equivalents thereof. These examples are intended to help illustrate the invention, and are not intended to, nor should they be construed to, limit its scope.

EXAMPLES

Materials and Methods for Examples 1-9

Cell Lines

The wild-type FLT3 Ba/F3 cell line, a murine interleukin 3 (IL-3)-dependent hematopoietic pro-B cell line, the chinese hamster ovary cell line CHO-$K_i$ and the murine p815 mast cell line was obtained from the American Type Culture Collection (ATCC, Manassas, Va.). The murine D814Y mutation described in this cell line is homologous to the human KIT D816Y mutation. The human steel factor (SLF) dependent M-07e cell line was obtained from Dr. Hal Broxmeyer (Department of, Microbiology and Immunology, Walther Oncology Center, Idiana University School of Medicine, Indianapolis, Ind.). All cell lines were grown in RPMI 1640 supplemented with 10% fetal bovine serum (FBS) (HyClone, South Logan, Utah), 1% Penicillin G (10,000 units/mL) and Streptomycin (10,000 ug/mg), 2 mM L-Glutamine (both Gibco-Invitrogen, Carlsbad, Calif.). Filtered IL3 containing supernatant (10%) from WEHI-3 cells (ATCC, Manassas, Va.) was added to the growth medium for the parental Ba/F3 cell line. M-07e cells were cultured using recombinant human granulocyte-macrophage colony stimulating factor as a growth supplement as described in Heinrich, et al., Blood, 96:925-932 (2000).

Site Directed Mutagenesis and Generation of a Ba/F3 Cell Line Expressing Mutant KIT KIT cDNA was generously provided by Dr. Axel Ullrich (Department of Molecular Biology, Max Planck Institute for Biochemistry, Martinsried, Munich, Germany) and cloned into the pLXSN retroviral vector plasmid (BD Biosciences, Palo Alto, Calif.), the pcDNA3.1 vector plasmid or the M5gNeo plasmid (Lu, L., et al., Blood, 94:2319-2332 (1999)). Site directed mutagenesis was used to create the D816V, D816Y, D816F mutations (QuickChange Kit, Stratagene, La Jolla, Calif.) and all mutations were confirmed by bidirectional sequencing (O'Farrell, A. M., et al., Blood, 101: 3597-3605 (2003)). Retroviral transduction was performed and Ba/F3 cell lines stably expressing mutant KIT isoforms were generated by double selection for G418 resistance and IL-3 independent growth (Yee, K. W., et al., Blood, 100:2941-2949 (2002);Yee, K. W., et al., Blood, 104:4202-4209 (2004); Tse, K. F., et al., Leukemia, 14:1766-1776 (2000); Schittenhelm, M. M., et al., manuscript submitted (2005)). Transient transfections of CHO-K1 chinese hamster cell lines with KIT wild type ("WT") or mutant isoforms were performed using a lipofection-assay (LipofectAMINE-kit purchased from Gibco-Invitrogen, Carlsbad, Calif.). Cells were treated with BMS-354825 24 hours after transfection (Heinrich, M. C., et al., Journal of Clinical Oncology, 21:4342-4349 (2003)).

Antibodies and Reagents

An anti-KIT rabbit polyclonal antibody, an anti-STAT3 mouse monoclonal antibody (both Santa Cruz Biotechnology, Santa Cruz, Calif.), an anti-AKT (polyclonal) rabbit antibody (Cell Signaling Technology, Beverly Mass.) and an anti-MAP kinase 1/2 (Erk 1/2) rabbit monoclonal antibody (Upstate Biotechnology, Lake Placid, N.Y.) were used at a 1:5000 to 1:2000 dilution. Anti-phosphotyrosine KIT antibodies (Tyr568/570 and Tyr703), an anti-phosphothreonine/tyrosine MAP kinase (Thr202/Tyr204) antibody, an anti-phosphothreonine C1 hr308) and an anti-phosphoserine (Ser473) AKT antibody, an anti-phosphotyrosine (Tyr705) STAT3 antibody and an unspecific anti-phosphotyrosine antibody (clone pY20) were used at dilutions of 1:100 to 1:2000 (all Cell Signaling Technology, Beverly Mass.). Peroxidase conjugated goat anti-mouse antibody and goat anti-rabbit antibody were used at 1:5000 and 1:10,000 dilutions respectively (BioRad; Hercules, Calif.). Protein A/G PLUS-Agarose immunoprecipitation reagent was purchased from Santa Cruz Biotechnology (Santa Cruz, Calif.). The small molecule compound BMS-354825 was obtained from Bristol-Myers Squibb (Princeton, N.J.). Imfatinib mesylate (STI-571/Gleevec®) was purchased from the Oregon Health Science University Hospital pharmacy (Portland, Oreg.). Imatinib and BMS-354825 were dissolved in DMSO to create 10 mM stock solutions and stored at −20° C.

Western Blots

~5×10$^7$ cells were exposed to varying concentrations of BMS-354825 and cultured for 90 minutes at 37° C. in a 5% $CO_2$ atmosphere. Cell pellets were lysed with 100-150 μL of protein lysis buffer (50 mM Tris, 150 mM NaCl, 1% NP-40, 0.25% deoxycholate with added inhibitors aprotinin, ABBSF, leupeptin, pepstatin, sodium orthovanadate, and sodium pyruvate). 500-2000 microgram of protein from cell lysates were used for imnimunoprecipitation experiments and 75-200 microgram of protein from cell lysates were used for whole cell protein analysis by western inimunoblot assays as previously described in Hoatlin, M. E., et al., Blood, 91:1418-1425 (1998).

Proliferation Assays

Cells were added to 96-well plates at densities 30,000 cells/well. BMS-354825 was added and proliferation was measured at 72 hours using an XTT-based assay (Roche Molecular Biochemicals; Indianapolis, Ind.) (Heinrich, M. C., et al., Blood, 96:925-932 (2000)).

Apoptosis Assays

Cells were incubated with BMS-354825 for 48-72 hours and translocation of phosphatidylserine from the inner to the outer leaflet of the plasma membrane as an early indicator of apoptosis was analysed using an Annexin V-FITC kit (Immunotech, Marseille, France) (Heinrich, M. C., et al., Blood, 96:925-932 (2000)) and a FACScalibur flow cytometer loaded with CellQuest analysis software (BD, Heidelberg, Germany).

Data Analysis

Dose-effect plots were created to calculate the $IC_{50}$ for the treatment effect of BMS-354825 for each cell line (Yee, K. W., et al., Blood, 104:4202-4209 (2004); Chou, T. C., et al., Adv. Enzyme Regul., 22:27-55 (1984). (Calcusyn Software available from Biosoft, Cambridge, UK). The results are expressed as an $IC_{50}$, which is the drug concentration required to inhibit cell proliferation (i.e. absorbance at 492 nM) to 50% of that of untreated control cells.

Example 1

BMS-354825 Inhibits the Kinase Activity of Wild Type and JM-mutant KIT Isoforms

BMS-354825 is a potent dual SRC/ABL kinase inhibitor that is currently in phase I/II clinical studies of CML and solid tumors. We now show herein that BMS-354825 potently inhibited the ligand-dependent autophosphorylation of wild-type KIT kinase in the SCF-dependent human myeloid leukemia cell line M-07e with an $IC_{50}$ of 1-10 nM. BMS-354825 also inhibited SCF-dependent proliferation of these cells with a similar $IC_{50}$ ($IC_{50}$ 5-10 nM. In comparison, the $IC_{50s}$ for imatinib inhibition of autophosphorylation and proliferation are 50-100 nM, respectively (Heinrch, M. C., et al., Science, 299:708-710 (2003) (FIG. 1A-B). BMS-354825 had little effect on the GM-CSF dependent proliferation of these cells ($IC_{50}$>10,000 nM), suggesting that the effect of BMS-354825 on SCF-dependent proliferation is due to its inhibition of KIT kinase rather than direct effects on downstream kinases (e.g., SRC family members) that might be common to both the KIT and GM-CSF receptors (FIG. 1B).

Gain-of-function mutations involving the KIT juxtamembrane domain ("JM"), occur in some cases of mast cell disease (Akin, C., et al., Blood, 103:3222-3225 (2004)) and acute myelogenous leukemia ("AML") (Beghini, A., et al., Haematologica, 89:920-925 (2004)). In addition, KIT JM mutations are found in approximately two-thirds of gastrointestinal stromal tumors (GISTs), and this GIST subset has the best clinical response to imatinib (Heinrich, M. C., et al., Journal of Clinical Oncology, 21:4342-4349 (2003); Heinrich, M. C., et al., Blood, 96:925-932 (2000), Corless, C. L., et al., J. Clin. Oncol., 22:3813-3825 (2004); Debiec-Rychter, M., et al., Eur. J. Cancer, 40:689-695 (2004); Heinrich, M. C., et al., Hum. Pathol., 33:484-495 (2002)).

We tested the activity of BMS-354825 against KIT JM mutations. Both BMS-354825 and imatinib inhibited cellular proliferation of the KIT V560G mutant cells with an $IC_{50}$ of 5-10 mM (data not shown). However BMS-354825 induced apoptosis of KIT V560G mutant cells with an $IC_{50}$ of 14 nM, whereas the $IC_{50}$ for imatinib was ~70 nM (data not shown).

Example 2

BMS-354825 Inhibits the Kinase Activity of Imatinib-resistant KIT AL Mutations Found in Hematological Malignancies Although imatinib potently inhibits the kinase activity of WT and mutant JM KIT kinase, it has minimal activity against KIT D816Y, D816F or D816V mutant kinases (Ma, Y., et al., Blood, 99:1741-1744 (2002)). The inability of imatinib to inhibit these mutant KIT isoforms is due to steric clash between imatinib and the "open" (or active) conformation of the KIT AL (Lombardo, L. J., et al., J. Med. Chem., 47:6658-6661 (2004); Shah, N. P., et al., Science, 305:399-401 (2004)). The predicted structural model of BMS-354825 binding to ABL suggests that changes in AL conformation might not significantly impact drug binding. Therefore, BMS-354825 inhibition activity was tested against mutant KIT kinases involving codon 816 using the spontaneously occurring murine mastocytosis cell line, p815, which expresses a murine KIT D814Y mutation that is homologous to the human D816Y mutation. BMS-354825 potently inhibited KIT autophosphorylation with an $IC_{50}$ of 1-10 nM and inhibited the cellular proliferation and induced apoptosis of p815 cells with $IC_{50s}$ of 10-25 nM and ~25 nM, respectively (FIG. 2A-FIG. 2C). Therefore, BMS-354825 inhibition of KIT kinase in p815 cells is strongly correlated with inhibition of cellular proliferation and induction of apoptosis. In contrast, 1200 nM imatinib only inhibited the proliferation of p815 cells by 30% and did not induce programmed cell death.

Example 3

Effects of Different Amino Acid Substitutions of KIT Aspartic Acid 816 (D816) on Sensitivity to BMS-354825

In order to assess whether BMS-354825 might have different potency against different KIT 816 mutants, such as the D816Y, D816V, and D816F mutations, we generated isogenic factor-independent Ba/F3 cell lines expressing SM-associated codon 816 mutations with an interchange of aspartic acid to valine, (D816V), tyrosine (D816Y), or phenylalanine (D816F). BMS-354825 inhibited the autophosphorylation of the human KIT D816V and D816F mutations with an $IC_{50}$ of approximately 100 nM. However, the $IC_{50}$ for inhibition of autophosphorylation of the KIT D816Y mutation was significantly lower ($IC_{50}$ 1-10 nM, FIG. 3A).

In comparison, imatinib in doses of up to 10,000 nM did not significantly inhibit KIT-autophosphorylation in D816V and D816F cells. However, D816Y cells were moderately sensitive to imatinib therapy with doses of >1000 nM but<10,000 nM completely inhibiting KIT autophosphorylation (FIG. 3B). These findings are in agreement with our results for the murine p815 (D814Y) cell line shown in FIG. 2A-2C.

Example 4

BMS-354825 Inhibits KIT-dependent Activation of Downstream Signaling Pathways

We also studied the effects of inhibition of KIT kinase by BMS-354825 on the activation status of KIT-dependent downstream signaling pathways, including MAPK, AKT and STAT3. FIG. 4 shows representative western blots for factor-independent Ba/F3 cells expressing human KIT D816V, D816F or D816Y mutations. For comparison, we also show the effects of BMS-354825 on activation of MAPK1/2, AKT, and STAT3 in p815 cells. MAP kinase 1/2 (ERK1/2), STAT3 and AKT are constitutively activated in these cells. The phosphorylation of STAT3 and MAPK1 was potently and completely inhibited in BMS-354825-treated cells with $IC_{50s}$ that are similar to those for inhibition of KIT autophosphorylation. AKT activation is potently but incompletely inhibited using BMS-354825 doses of 10-1000 nM. Similarly, MAPK2 activation was also less potently inhibited than MAPK1 (FIG. 4).

Example 5

Figure 5A:
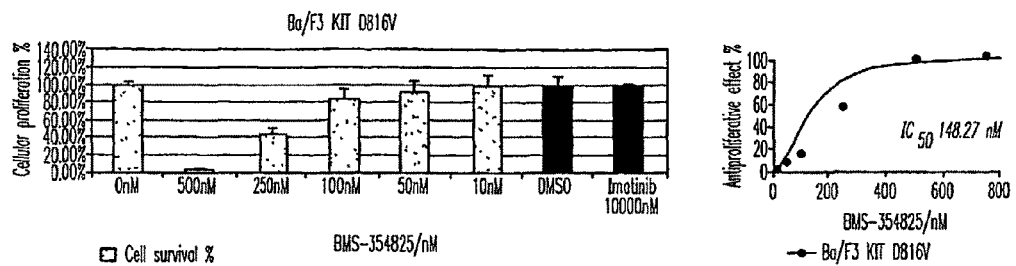
FIG. 5 BMS-354825 inhibits cellular proliferation of Ba/F3 KIT D816V/F/Y cells in a dose-dependent manner. Ba/F3 KIT D816V/F/Y cells were treated with BMS-354825, imatinib mesylate, or vehicle only for 72 h before measuring cellular proliferation using an XTT-based assay. Representative experimental results are shown in the bar graph figures (error bars indicate one standard deviation). The dose-effect plots indicate the computed $IC_{50}$ for the experiments shown immediately to the left of the plot. BMS-354825 successfully inhibited proliferation of Ba/F3 KIT D816V/F/Y cells with an $IC_{50}$ of 150 nM (D816V, FIG. 5A), 100 nM (D816F, FIG. 5B) and 5 nM (D816Y, FIG. 5C), respectively. Imatinib in contrast has no or only moderate antiproliferative effects up to a tested dose range of 10,000 nM.
Figure 5B:
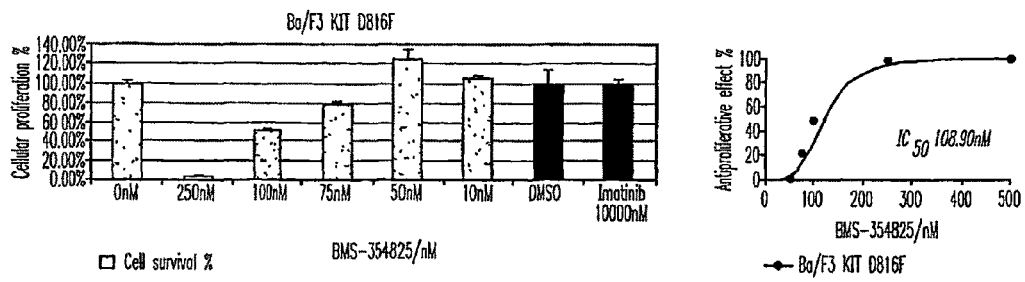
Figure 5C:
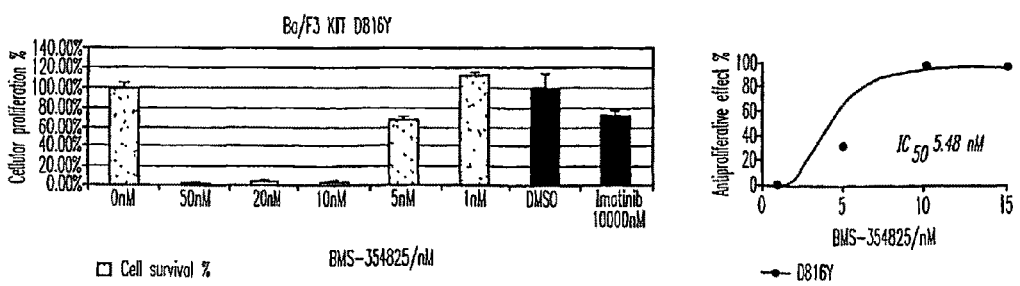
Figure 6A:
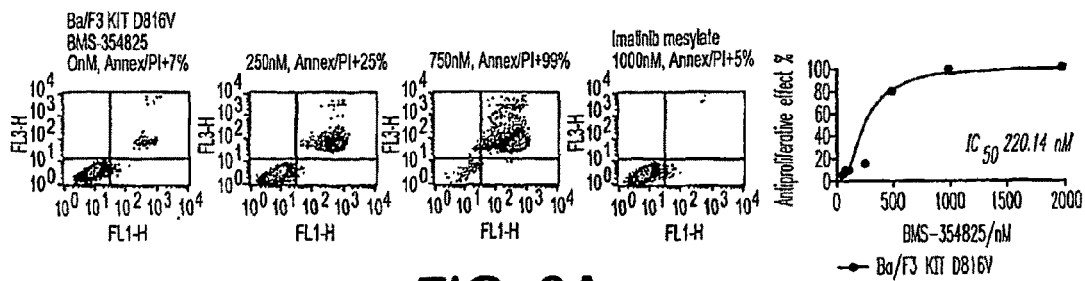
FIG. 6 BMS-354825 induces apoptosis of Ba/F3 KIT D816V/F/Y cells in a dose-dependent manner. Ba/F3 KIT D816V/F/Y cells were treated with BMS-354825, imatinib mesylate, or vehicle only for 48-72 h before assessing apoptosis using a flow cytometric-based assay. Representative experimental results are shown in the flow cytometry dot-plot figures. The dose-effect plots indicate the computed $IC_{50}$ for the flow cytometry experiments shown immediately to the left. BMS-354825 potently induced apoptosis in Ba/F3 KIT D816V/F/Y cells with $IC_{50s}$ of 220 nM (D816V, FIG. 6A), 120 nM (D816F, FIG. 6B) and 15 nM (D816Y, FIG. 6C), respectively. In contrast, 1000 nM imatinib did not induce apoptosis of any of these cell lines.
Figure 6B:
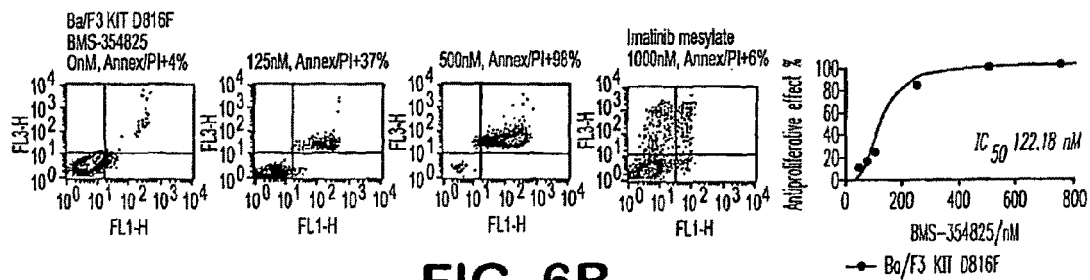
Figure 6C:
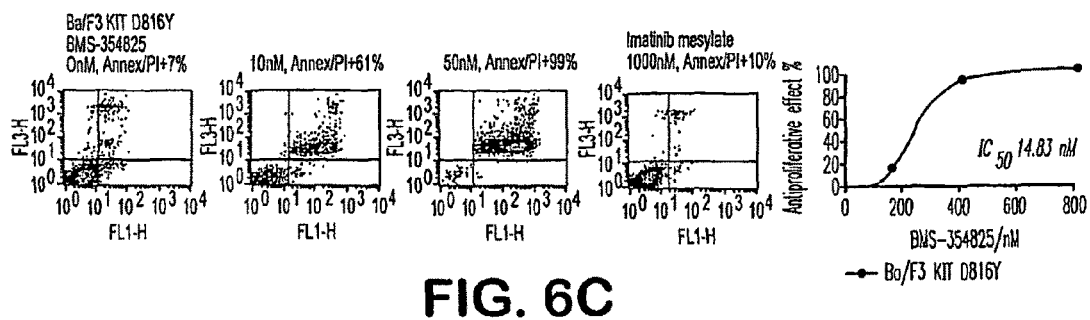

Effects of BMS-354825 on Cellular Proliferation and Survival of Isogenic Cells Expressing KIT D816F/V/Y Consistent with the results of our biochemical studies, BMS-354825 inhibited the proliferation of Ba/F3 KIT D816V and D816F cells with an $IC_{50}$ of 100-150 nM and with an $IC_{50}$ of 5 nM for inhibition of proliferation of Ba/F3 D816Y cells. In contrast, imatinib had no significant inhibitory effect on the growth of these three cell lines ($IC_{50}$>10,000 nM, FIG. 5A-FIG. 5C). BMS-354825 also potently induced apoptosis of the Ba/F3 KIT D816V and D816F cell lines with calculated $IC_{50s}$ of 220 mM and 120 nM, respectively. The $IC_{50}$ for induction of apoptosis of the Ba/F3 D816Y cell line was 15 nM (FIG. 6C). As shown, BMS-354825 is at least one log more potent against KIT D816Y than against KIT D816V/F (FIG. 6A-6C).

Example 6

Figure 7:
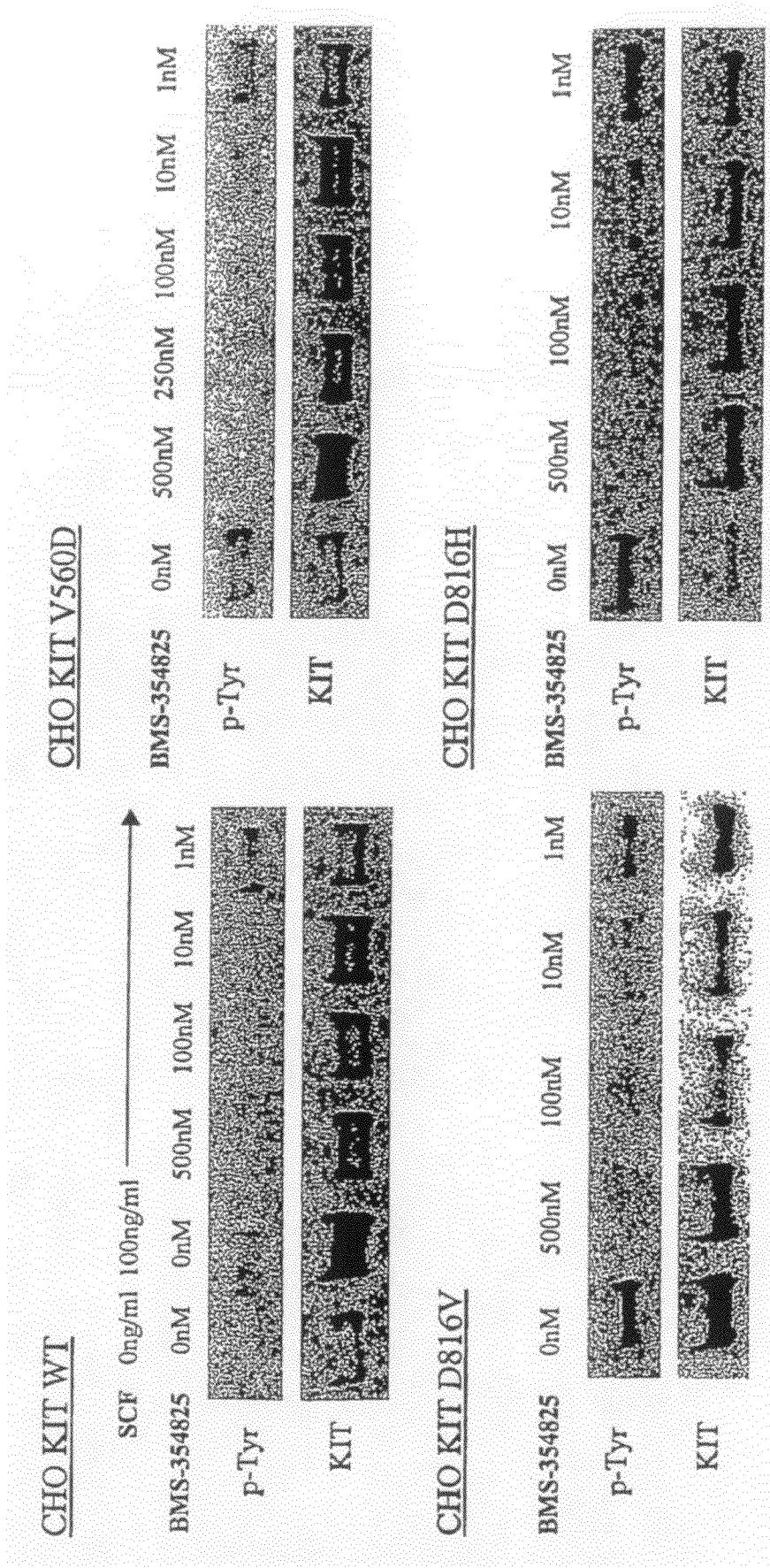
FIG. 7 BMS-354825 has differential potency against WT or JM-Mutant KIT isoform compared with AL-mutant KIT isoform. Transient transfected CHO-K1 cells harboring WT KIT or a mutant KIT isoform were treated with varying concentrations of BMS-354825 for 90 minutes. In addition, SCF ligand was added to cells transfected with the WT KIT construct. Protein lysates were immunoblotted with an anti-KIT antibody, before immunoblotting for phosphorylated tyrosine residues (p-TYR) or total KIT. BMS-354825 potently inhibits SCF-induced phosphorylation of WT KIT with an $IC_{50}$ of approximately 1-10 nM ("CHO KIT WT"). Autophosphorylation of the V560D JM mutation, is inhibited by BMS-354825 with an $IC_{50}$ of ~10 nM ("CHO KIT V560D"), and the AL mutations D816V and D816H are inhibited with $IC_{50s}$ in the range of 100 nM (("CHO KIT D816V"; "CHO KIT D816H"; respectively)).
Figure 10A:
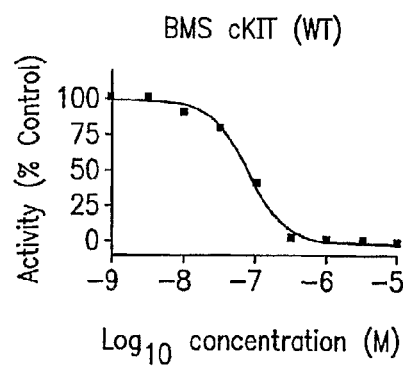
FIG. 10 shows inhibition of the kinase activity of human wild-type and mutant (D816V) c-KIT by BMS-354825 (FIG. 10A and FIG. 10B) and imatinib (FIG. OC and FIG. 10D). Kinase activity was conducted on N-terminal GST tagged recombinant c-KIT (amino acids 544-end).
Figure 10B:
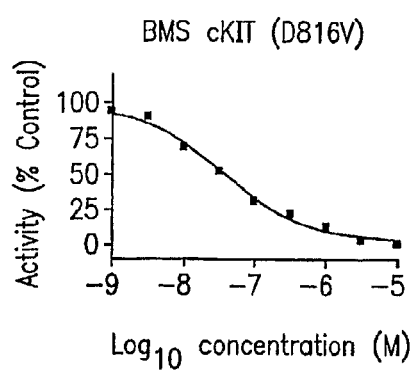
Figure 10C:
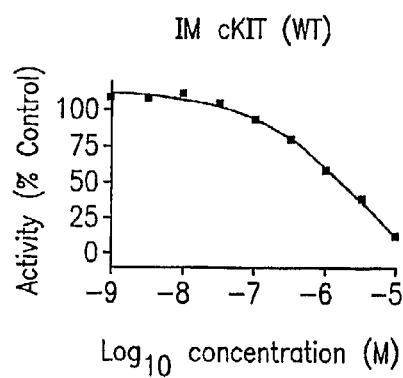
Figure 10D:
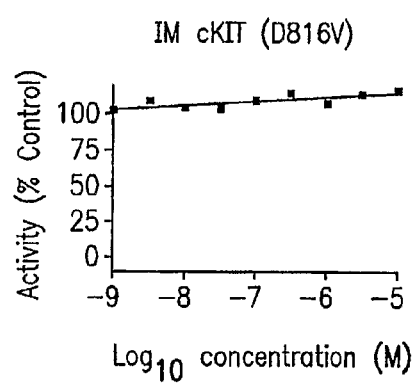

BMS-354825 is One-log More Potent Against WT or JM-mutant KIT Isoforms than AL-mutant KIT Isoforms In order to compare WT KIT to AL-mutant KIT in the same cellular context, additional experiments were performed in which CHO cells were transiently transfected with expression vectors encoding WT or mutant KIT isoforms. Transfected cells were treated with BMS-354825 and biochemically analyzed as described above. BMS-354825 inhibited the autophosphorylation of SCF-stimulated WT KIT (analogous to M-07eE) or JM-mutant KIT with an $IC_{50}$ of 1-10 nM, whereas the $IC_{50}$ for inhibition of autophosphorylation of the KIT D816V and the D816H mutations (reported in <5% of SM (Valent, P., et al., Leuk. Lymphoma, 46:35-48 (2005) and 7% of seminoma cases (Kemmer, K., et al., Am. J. Pathol., 164:305-313 (2004)), was approximately 100-500 nM (FIG. 7).

Example 7

Inhibition of the Kinase Activity of Human Wild-type and Mutant (D816V) c-KIT by BMS-354825

In a final reaction volume of 25 µl, WT KIT kinase or mutant KIT kinase (D816V) (5-10 mU) was incubated with 8 mM MOPS pH 7.0, 0.2 mM EDTA, 10 mM MnCl$_2$, 0.1 mg/nl poly(Glu/Tyr) 4:1, 10 mM MgAcetate and [γ-$^{33}$P-ATP] (specific activity approx. 500 cpm/µmol, concentration as required). The reaction was initiated by the addition of the MgATP mix. After incubation for 40 minutes at room temperature, the reaction was stopped by the addition of 5 µl of a 3% phosphoric acid solution. 10 µl of the reaction was then spotted onto a Filtermat A and washed three times for 5 minutes in 75 mM phosphoric acid and once in methanol prior to drying and scintillation counting. As shown in FIG. 10, BMS-354825 effectively inhibits the kinase activity of mutant KIT kinase containing a D816V mutation.

Example 8

Inhibition of Cell Growth of the p815 Murine Mastocytosis Cell Line Harboring a KIT Mutant (D814Y)

Figure 11A:
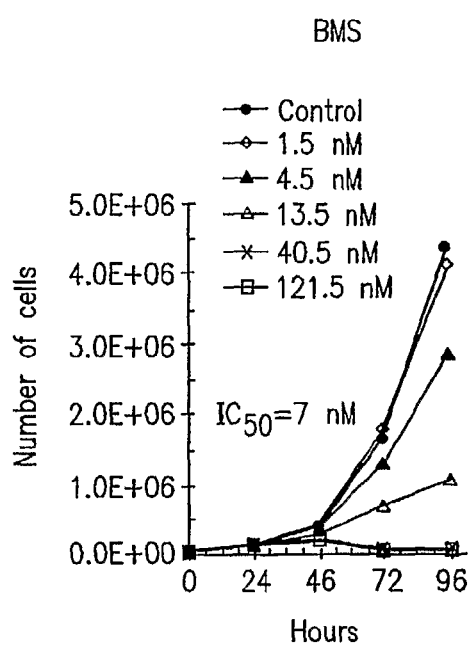
FIG. 11 shows inhibition of cell growth of the p815 murine mastocytosis cell line harboring a cKIT mutation (D814Y). Cells were grown in the presence of varying concentrations of BMS-354825 (FIG. 11A) or imatinib (FIG. 11B). Days in culture at the time of analysis is indicated. Concentrations of the inhibitors are listed in nM.
Figure 11B:
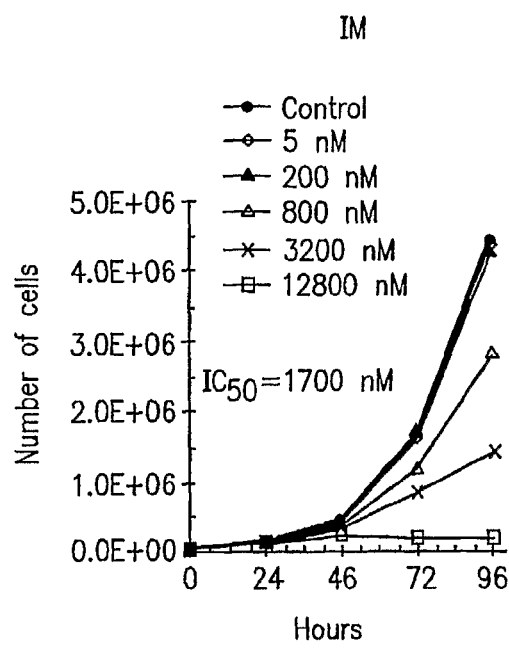

The murine P815 mastocytoma cell line expressing the D814Y mutation (corresponding to human D816Y) was purchased from American Type Culture Collection (ATCC, Culture Collection (ATCC; Manassas, Va.)). The cells were cultured in RPMI 1640 medium supplemented with 10% fetal bovine serum (FBS) and 25 mM HEPES buffer at 37° C./5% $CO_2$. As shown in FIG. 11 the $IC_{50}$ for inhibition of cell growth for BMS-354825 was 7 nM, while the $IC_{50}$ for inhibition of cell growth for imatinib was 1700 nM.

As discussed above, gain-of-function point mutations of the KIT activation loop ("AL") are associated with certain human neoplasms, including systemic mast cell disorders, AML, seminoma and GIST (both primary and imatinib-resistant GIST). In the case of mast cell disorders, seminoma, and AML, the most commonly-associated KIT mutation is the replacement of the normal aspartic acid residue at codon 816 of the activation loop with a valine residue (D816V). The D816V mutation results in constitutive activation of KIT kinase activity and is predicted to help stabilize the AL in the active conformation. In addition to D816V, other mutations involving codon 816 have been reported in systemic mast cell disorders (D816Y, D816F), AML (D816Y) and/or seminomas (D816Y, D816H). Consistent with the structural model of imatinib binding to KIT, the kinase activity of all of these mutants is resistant to imatinib.

As described in the present invention BMS-354825 was determined to be a potent inhibitor of wild type KIT with an $IC_{50}$ for inhibition of autophosphorylation and cellular proliferation of 5-10 nM. In comparison, the $IC_{50}$ for inhibition of autophosphorylation and proliferation in these same cells by imatinib was 10- to 20-fold higher (~100 nM).

Juxtamembrane ("JM") mutations of KIT are commonly associated with human GISTs, and a minority of cases of SM and AML. BMS-354825 also potently inhibits KIT JM-mutations with an $IC_{50}$ of 1-10 nM. BMS-354825 had similar potency to imatinib for inhibition of KIT autophosphorylation and cellular proliferation in a mast cell line expressing JM-mutant KIT (data not shown) and was even more potent than imatinib for inducing apoptosis of this cell line, with $IC_{50s}$ of ~15nM (BMS-354825) and ~70 nM (imatinib), respectively (data not shown).

BMS-354825 is a much more potent inhibitor of KIT AL-mutants than imatinib, with $IC_{50s}$ for inhibition of autophosphorylation of KIT D816 mutants in the range of 10-100 nM. The potency of BMS-354825 against KIT kinase is differentially influenced by various AL mutations. For example, KIT D816Y is 10-fold more sensitive to BMS-354825 than KIT D816V or KIT D816F. In addition, KIT D816F is approximately 2-fold more sensitive to BMS-354825 compared with KIT D816V.

As described herein inhibition of KIT kinase in human mastocytosis cell lines (data not shown) and p815 (murine mastocytosis) resulted in inhibition of cellular proliferation and induction of apoptosis. Since it is known that KIT kinase inhibition is developmentally required for mast cell formation; inhibition of an alternative oncogenic kinase (FIP1L1-PDGFRA) results in marked clinical responses in variant SM associated with this genomic alteration; and inhibition of KIT D816V by the kinase inhibitor PKC412, resulted in hematological and clinical improvement in a patient with mast cell leukemia, the data disclosed herein supports the aspect of the present invention that therapeutic inhibition of KIT kinase would be effective for human mastocytosis that is associated with KIT D816 mutations.

As disclosed herein BMS-354825 is expected to have biological and clinical activity against human diseases associated with KIT AL-mutations, including mast cell disease, in particular systemic mastocytosis ("SM"), AML, seminoma and imatinib-resistant GIST.

Example 9

Activating Mutations of the Activation Loop (AL) of Kit are Associated with Certain Human Neoplasms, Including a Subset of Patients with AML and Systemic Mast Cell Disorders (SM)

KIT AL mutations such as D816V that are typically found in AML and SM are resistant to imatinib (IM, $IC_{50}$>5-10 µM). Dasatinib (BMS-354825) is a novel, oral, multi-targeted kinase inhibitor that targets BCR-ABL and SRC. Due to its potent inhibition of these kinases, dasatinib is currently being tested in patients with imatinib-resistant/-intolerant CML/Ph+ ALL in clinical trials. Based on previous observations of the ability of certain SRC/ABL inhibitors to also inhibit KIT kinase, we hypothesized that dasatinib might inhibit the kinase activity of both WT and mutant KIT isoforms. The inhibitory potential of dasatinib against WT KIT, KIT mutant isoforms and KIT-dependent downstream pathways was evaluated by immunoblotting. In addition, we evaluated the effects of dasatinib on cellular proliferation and induction of apoptosis. Dasatinib potently inhibited WT, juxtamembrane- (JM and AL-mutant KIT autophosphorylation. Based on the ability of dasatinib to bind to BCR-ABL irrespective of the ATP AL conformation (inactive versus active), dasatinib was expected to be insensitive to KIT AL conformation. In contrast, we found that the $IC_{50}$ for KIT autophosphorylation varied significantly among the various KIT mutant isoforms: WT KIT, D816Y, V560G (JM mutation) [$IC_{50}$ 1-10 nM]<D816F [$IC_{50}$ 100 nM]<D816V [$IC_{50}$ 200-250 nM]. These results indicate that the conformation of the KIT AL does influence dasatinib potency. Inhibition of KIT kinase activity by dasatinib reduced cellular proliferation and induced apoptosis in mast cell/leukemia cell lines expressing mutant KIT isoforms. In these cell lines, KIT activates downstream pathways important for cell viability and cell survival such as RAS/MAPK, JAK/STAT and PI3K/AKT. Dasatinib potently blocked activation of MAPK1/2 and STAT3. Inhibition of KIT by dasatinib abrogated phosphorylation of AKT S473, but not AKT T308. This partial inhibition of AKT activation was insufficient to inhibit phosphorylation of p70S6K, a kinase downstream of AKT and mTOR. Combining dasatinib with rapamycin, a known mTOR inhibitor, had an additive to synergistic anti-proliferative effect on cells expressing KIT D816V. Our studies suggest that dastatinib may have clinical efficacy against human neoplasms that are associated with gain-of-function KIT mutations such as AML or SM. Combining dasatinib with mTOR inhibitors may further increase efficacy against KIT-driven malignancies.

Experiments were performed as described herein for the murine p815 and human BaF3 D816V cell lines. Specifically, apoptosis assays on the p815 cell lines were as described using the Annexin V-FITC kit assay (Immunotech, Marseille, France), and as described in the Heinrich, M. C., et al. (Journal of Clinical Oncology, 21:4342-4349 (2003) for BaF3 D816V.

Figure 12:
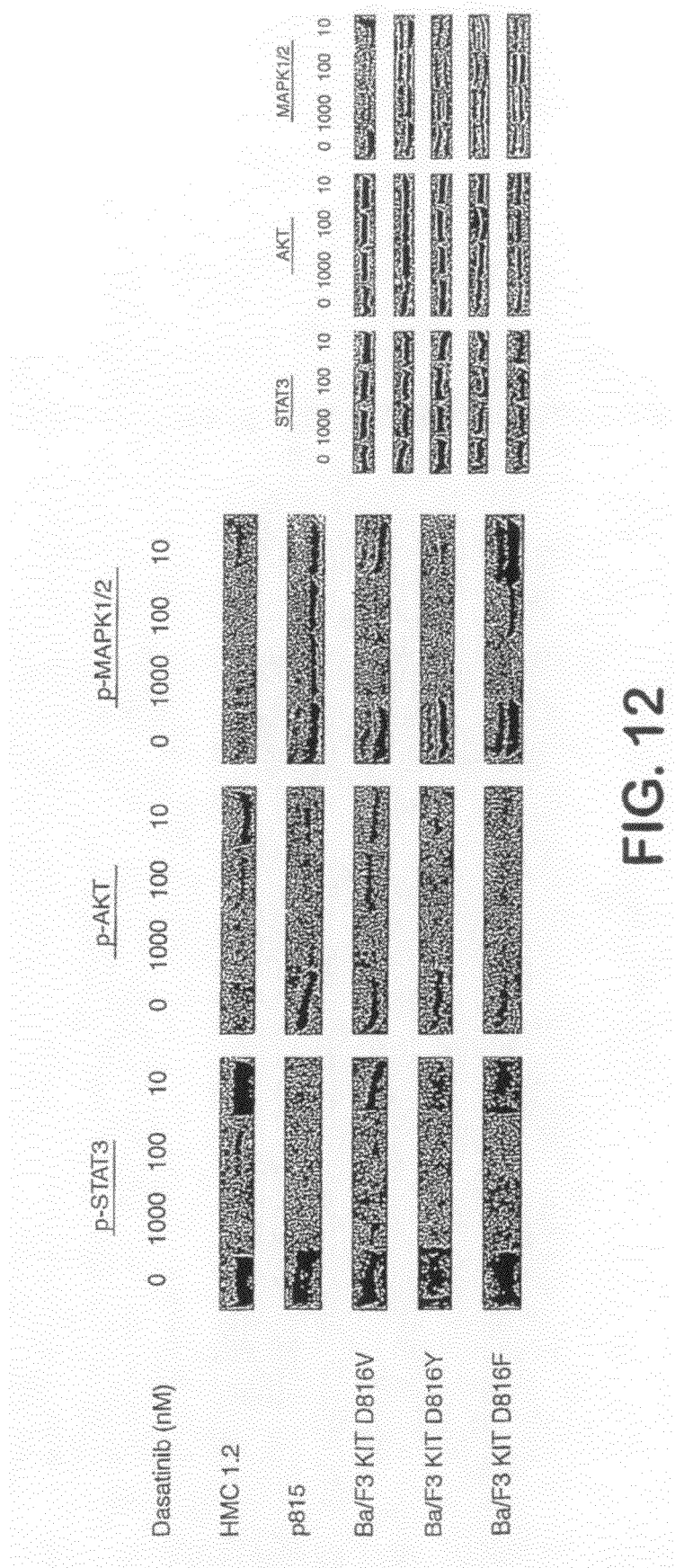
FIG. 12 shows dasatinib-mediated inhibition of AL-mutant KIT kinase activity blocks the activation of major downstream pathways. Cells with the indicated KIT AL mutations were grown in the presence of varying concentrations of BMS-354825, and protein lysates from each cell were immunoblotted for phosphorylated p-STAT3, p-AKT, and p-MAPK1/2, as well as total forms of STAT3, AKT, and MAPK1/2. Downstream pathways affecting phosphorylation of AKT, STAT3, and MAP kinases were activated in all untreated cell lines. As shown, treatment with dasatinib led to a marked decrease in the concentration of activated forms of STAT3, AKT, and MAPK1/2. Concentrations of the inhibitors are listed in nM.

As shown in FIG. 12, dasatinib-mediated inhibition of AL-mutant KIT kinase activity blocks the activation of major downstream pathways, including STAT3, AKT and MAPK1/2.

Figure 13:
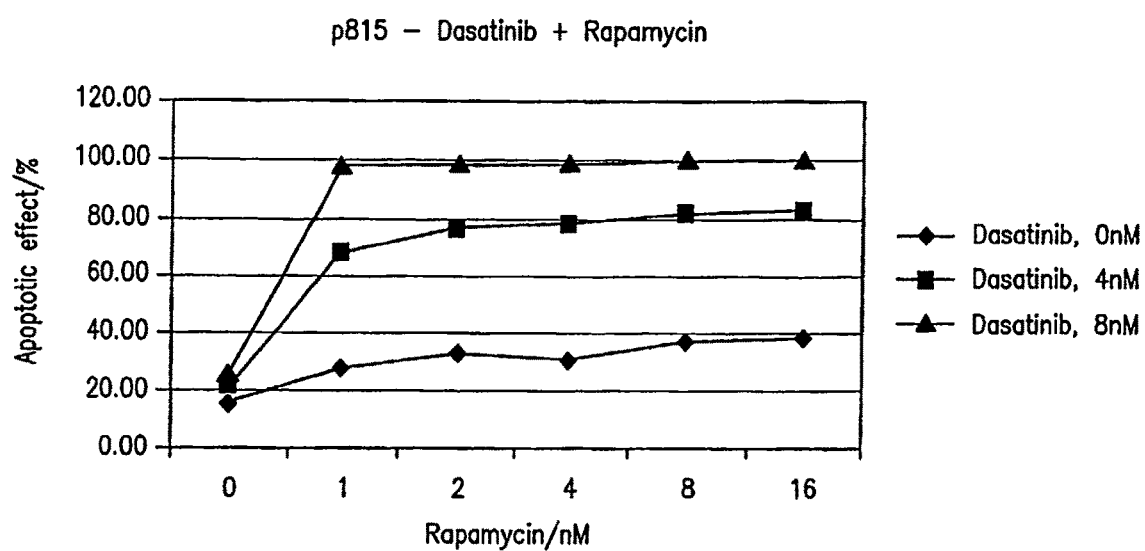
FIG. 13 shows the combination of BMS-354825 ("dasatinib") and Rapamycin synergistically induces apoptosis and mediates antiproliferative effects in a p815 mast cell line. In addition, dasatinib alone was found to not inhibit the phosphorylation status of p70S6kinase, a kinase downstream of AKT and mTOR, while rapamycin alone or in combination with dasatinib completely inhibited phospho-p70S6kinase in therapy relevant doses. Cells were grown in the presence of varying concentrations of Rapamycin with the indicated concentrations of BMS-354825. Concentrations are listed in nM.
Figure 14A:
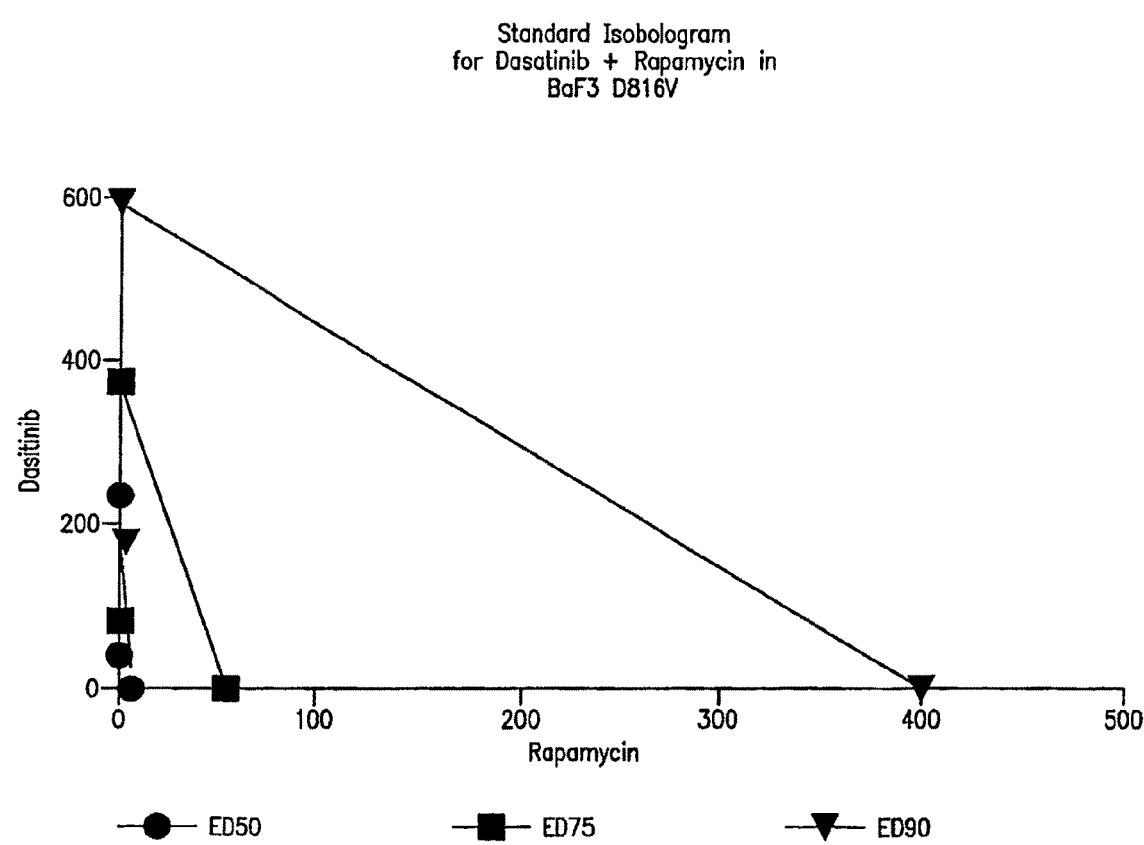
FIG. 14 shows a standard (FIG. 14A) and conservative (FIG. 14B) isobologram comparing the antiproliferative effects achieved in BaF3 KIT D816V cell lines by the combination of BMS-354825 ("dasatinib") and Rapamycin for ED of 50%, 75%, and 90%. As shown, the combination of BMS-354825 ("dasatinib") and Rapamycin are strongly synergistic. Cells were grown in the presence of varying concentrations of Rapamycin with the indicated concentrations of BMS-354825. Concentrations are listed in nM.
Figure 14B:
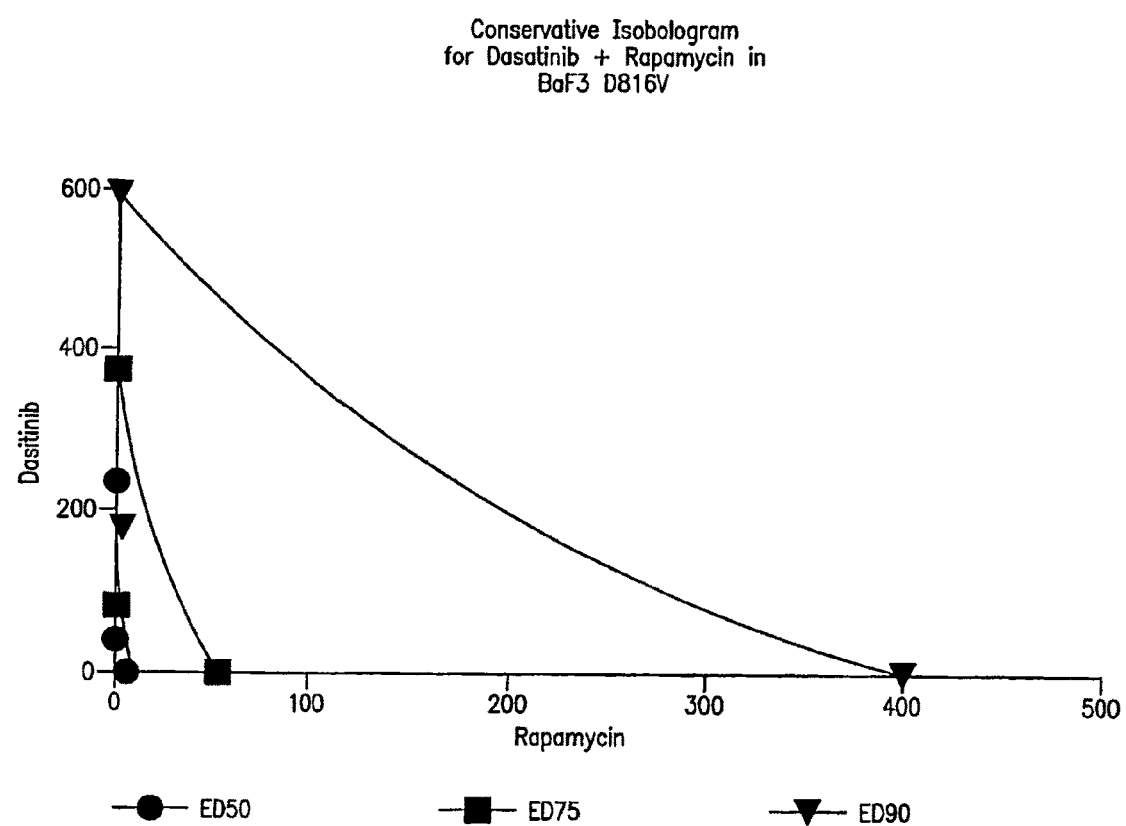
Figure 15:
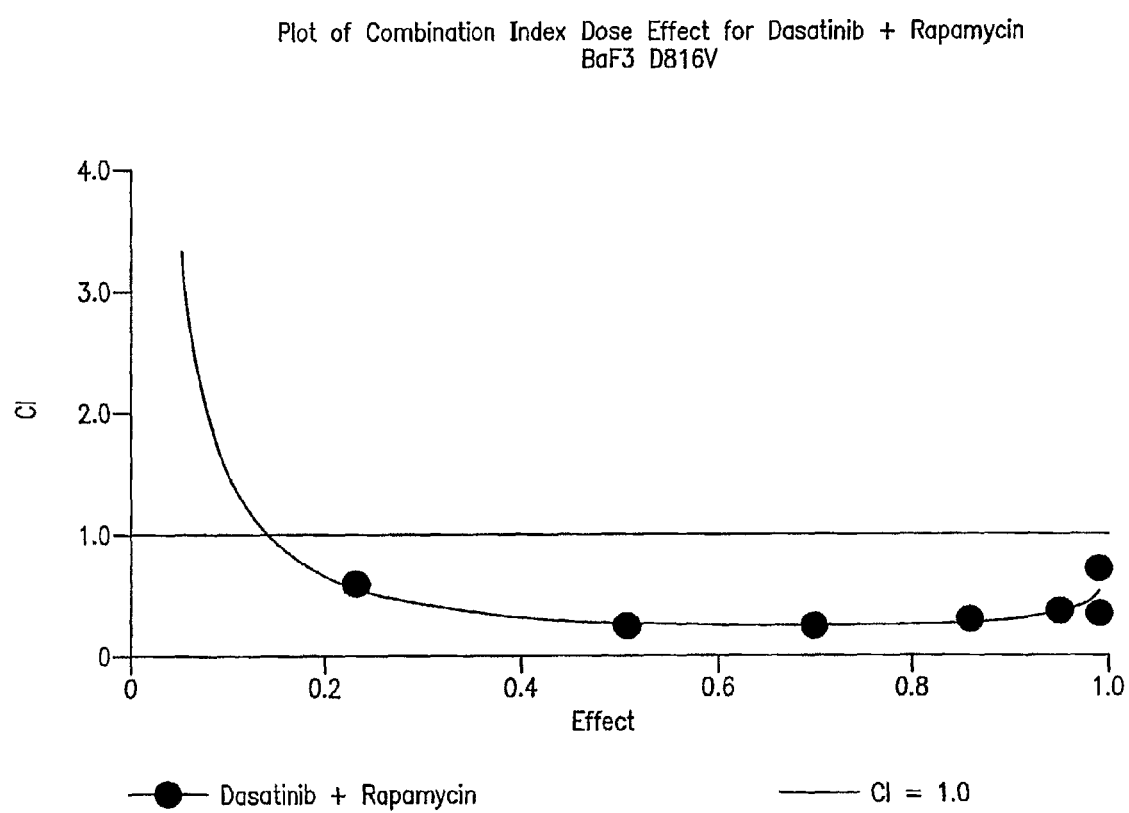
FIG. 15 shows the plot of a combination index for the combination of BMS-354825 ("dasatinib") and Rapamycin measuring the antiproliferative effects achieved in BaF3 KIT D816V cell lines. A CI of less than 1 is indicative of a synergistic effect, a CI of 1 equals an additive effect, while a CI greater than 1 indicates an antagonistic effect. As shown, the combination of BMS-354825 ("dasatinib") and Rapamycin is strongly synergistic. Cells were grown in the presence of varying concentrations of Rapamycin with the indicated concentrations of BMS-354825. Concentrations are listed in mM. CI values were calculated using Calcusyn software (Biosoft) version 1.1.1.

As shown in FIGS. 13 to 15, the combination of dasatinib and rapamycin resulted in a strong synergistic effect on cellular antiproliferative and apoptosis of cells harboring the KIT D816V mutation.

The combination of dastatinib and rapamycin resulted in Combination Indices (CI) of 0.30, 0.26, and 0.32 for antiproliferative effects of 50, 75 and 90% (ED50, ED75, and ED90). A CI<1 is indicative of a synergistic effect, a CI=1 is indicative of an additive effect, and a CI>1 is indicative of an antagonistic effect. CI values were calculated using Calcusyn software (Biosoft) version 1.1.1.

According to the data obtained to date and as demonstrated herein, dasatinib can inhibit virtually all of the cellular proliferation and induce apoptosis in the cell lines tested when used in sufficient doses, whereas the maximal anti-proliferative effect of rapamycin was determined to only be around 50-60% inhibition using relevant doses for treating humans. However, levels as low as 4 nM of Dasatinib and 1 nM of rapamycin in p815 cells (harboring a mutation analogous to the human D816Y mutant) induced apoptosis of ~70% of p815 cells in an Annexin V/PI-experiment.

On the protein level, dasatinib alone was not able to inhibit the phosphorylation status of p70S6kinase, which is downstream of AKT and mTOR. In contrast, rapamycin alone or in combination with dasatinib completely inhibits phospho-p70S6kinase in therapy relevant doses. This might explain the synergistic cellular cytotoxic effect observed in p815 and Ba/F3 KIT D816V (data not shown) cell lines.

The synergistic effect of dasatinib and rapaamycin may be appreciated by calculating the theoretical level of these compounds required to achieve a certain level of anti-proliferative effect or apoptosis, both individually and in combination. For example, to inhibit cellular proliferation by 50% would require dasatinib dose of about 236 nM or a rapamycin dose of about 7.2 nm based upon the CI and the isobologram values described herein. However, using a combination of 40 nM of dasatinib+0.8 nM rapamycin, would result in 50% inhibition of cellular proliferation for the D816V mutant (the 1 log higher level of dasatinib required relative to the D814Y is consistent with the decreased dasatinib sensitivity observed for the D816V mutant). Alternatively, if the target inhibition of proliferation were 95%, 600 nM of dasatinib would be required and a very high concentration of rapamycin (>1 micromolar) would be required based upon the CI and the isobologram values described herein, with the latter level of rapamycin possibly being unachievable in humans. However, using a combination of 295 nM dasatinib and 5.9 nM rapamycin, one could achieve this level of antiproliferative effect for the D816V mutant.

Materials and Methods for Example 10

Tumor Samples and Cell Lines

Tumor samples were obtained from the Tissue Bank of the Oregon Health & Science University (OHSU) Cancer Institute, from the OHSU Departments of Pathology and Dermatology, the University of Chicago Section of Dermatology, and the Department of Pathology of the Brigham and Women's Hospital, Boston. LoVo cells (a colon cancer cell line that is wild-type for KIT) were obtained from the American Type Culture Collection. The stably transfected clones of Ba/F3 cells (murine interleukin 3-dependent hematopoietic pro-B cells) expressing wild-type, D816V, D816F or D816Y isoforms of human KIT cDNA are described in Schittenhelm et al. *Cancer Res* 66:473-81 (2006). DNA extracted from the Ba/F3 subclones was used in validation experiments.

DNA Preparation

DNA was extracted from LoVo and Ba/F3 cells with the QIAamp DNA mini kit (Qiagen #51306). The same kit was used to extract genomic DNA from blood and bone marrow aspirates, as well as from formalin-fixed tissue (unembedded), and formalin-fixed paraffin embedded tissue samples, in accordance with the manufacturer's recommendations.

Standard PCR

KIT exon 17 amplimers were generated from genomic DNA as previously described (Kemmer et al., *Am J Pathol* 164:305-13 (2004)). For the standard (control) PCR reaction, the forward primer was 5' TGTATTCACAGAGACTTGGC 3' (SEQ ID NO:3) and the reverse primer was 5' TAATGTTCAGCATACCATGCAA 3' (SEQ ID NO:4). This reverse primer matches sequences in KIT intron 17 and was also used in the allele-specific PCR. To amplify KIT cDNA sequences from Ba/F3 subclones, the same forward primer was matched with the reverse primer 5' GCTCCCAAAGAAAAATCCCATAGG 3' (SEQ ID NO:5).

Allele-specific PCR

Allele-specific PCR reactions were performed using 200 ng DNA and a master mix based on the Expand High Fidelity Polymerase kit (Roche # 11759078001), with 1.4 units of polymerase, 160 uM dNTP (Stratagene, Cedar Creek, Tex.), 400 nM mutation-specific primer (see FIG. 16), 200 nM blocking oligonucleotide (see FIG. 16), and 800 nM reverse primer (5' TAATGTTCAGCATACCATGCAA 3' (SEQ ID NO:4)). The cycling conditions were as follows: 95° C. for 1 min. followed by 45 cycles of 94° C. for 1 min, 55° C. for 1 min and 72° C. for 1 min, and a final 7 min incubation at 73° C.

HPLC and DNA Sequencing

PCR products Were analyzed on a denaturing HPLC system (WAVE™, Transgenomic, Inc., Omaha, Nebr.), as previously described (Corless et al., *J Clin Oncol* 22:3813-25 (2004)). DNA sequencing was performed using the BIGDye terminator kit (ABI) and analyzed on an ABI 310 capillary sequencer (Heinrich et al., *J Clin Oicol* 21:4342-49 (2003)).

Example 10

Allele-specific PCR Assay for Detecting D816V and D816F Mutations

Oncogenic mutations of KIT contribute to the pathogenesis of gastrointestinal stromal tumors, systemic mastocytosis (SM), and some cases of acute myelogenous leukemia (AML). The D816V and D816F substitutions in the activation loop of KIT result in complete resistance to the kinase inhibitor imatinib (Gleevec™). Because these mutations are particularly common in SM and AML, their detection has diagnostic and predictive significance. Unfortunately, the fraction of mutation-positive cells in clinical samples from SM patients is often below the 20-30% threshold needed for detection by direct DNA sequencing. We have developed an allele-specific PCR (AS-PCR) assay using a mutation-specific primer in combination with a wild-type blocking oligonucleotide that reproducibly amplifies D816V or D816F with an estimated sensitivity of 1% mutant allele in DNA extracted from formalin-fixed, paraffin-embedded tissue. The level of sensitivity is even higher when using DNA from unfixed tissue (e.g., bone marrow aspirate).

A) D816V Mutation

The mutation-specific primer (MSP) and the blocking oligonucleotide are shown in FIG. 16. The MSP is designed to prime from the mutant A of the T>A substitution of D816V, but includes an intentional mismatch in the penultimate 3' nucleotide. When aligned with wild-type (WT) sequence, the MSP is doubly mismatched at the 3' end, which limits its ability to prime. The MSP can also prime from the second nucleotide of the two-nucleotide substitution that results in D816F (FIG. 16), which is another mutation associated with systemic mastocytosis. The MSP may also amplify D816I and D816M (both perfect matches), as well as D816L (penultimate mismatch). However, these mutations have not been detected in systemic mastocytosis. On the other hand, the known mastocytosis-associated mutations D816H and D816Y would not be expected to amplify, as both are doubly mismatched to the last two MSP nucleotides.

The design of the blocking oligonucleotide (B-oligo) is the reverse of the MSP, such that it is doubly mismatched to the mutant D816V and D816F sequences, but only singly mismatched to WT. In addition, the 3' terminal nucleotide of the B-oligo was linked in a chemically reversed configuration (3' to 5') to eliminate any possibility of priming.

Studies were performed using DNA purified from cells that are heterozygous for the D816V mutation. The expected sequence of the amplified product was confirmed by bi-directional sequencing. The optimal hybridization temperature was 55° C. Addition of the B-oligo increased the sensitivity of the assay by 10 to 100-fold. Molar ratios of MSP to B-oligo ranging from 2:1 to 1:2 were tested and the most consistent results were observed at a 2:1 ratio, which was used in all subsequent assays. Additionally, doubling the concentration of the reverse primer relative to the MSP yielded more consistent amplifications.

Figure 17:
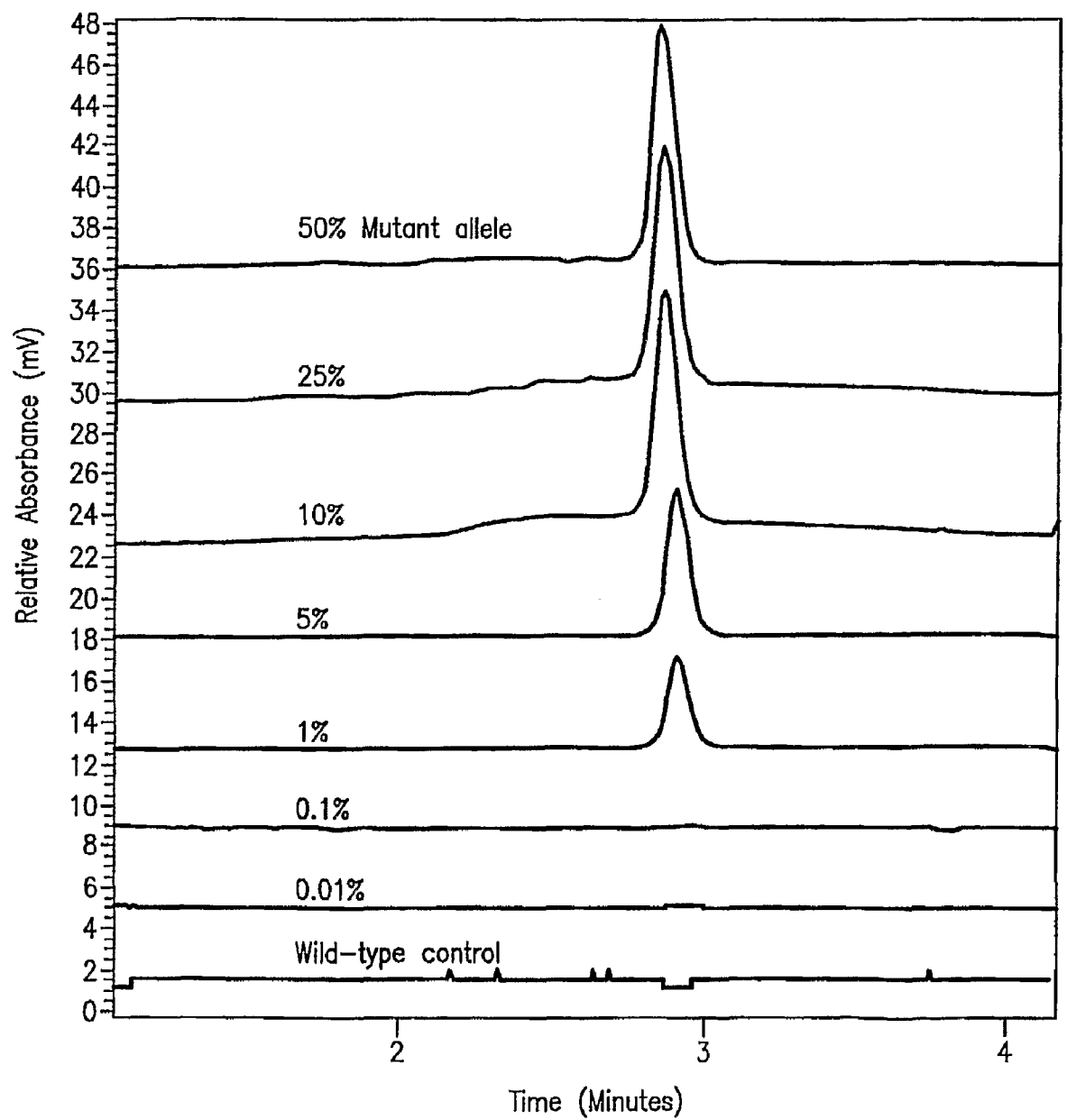
FIG. 17 shows the sensitivity of AS-PCR for detecting D816V in paraffin-derived DNA. DNA was extracted from formalin-fixed, paraffin-embedded seminoma heterozygous for KIT D816V (50% mutant allele) and was diluted with increasing amounts of KIT wild-type DNA (LoVo cell line) before amplification by AS-PCR.

The sensitivity of the AS-PCR assay for KIT D816V was influenced by the quality of the template DNA. Positive signals were routinely detectable at a level of 0.1% mutant allele using DNA extracted from cells, which are heterozygous for the D816V mutation, diluted into wild-type DNA from LoVo cells. The detection threshold was higher when paraffin-derived DNA from a seminoma heterozygous for D816V was diluted with the same wild-type LoVo DNA (FIG. 17). The D816V mutation in paraffin-derived DNA was reproducibly detected at the level of 1%. The positive control used for all AS-PCR reactions was a parallel tube containing the same reverse primer matched to a generic exon 17 forward primer, which was 5' to the allele-specific primer and yielded a larger amplicon.

B) D816F Mutation

KIT D816F is a rare mutation in mast cell disease and has not been reported in seminoma or GIST. cDNA from a KIT D816F-expressing BA/F3 clone was used as template to test detection of this mutation. The mutation was detectable in the range of 1% to 5%.

C) Validation of AS-PCR Assay

The AS-PCR assay was validated through the analysis of five types of samples. First, 64 samples of genomic DNA wild-type for KIT exon 17 were tested in the allele-specific reaction. No amplifications were observed with the MSP/B-oligo mixture, while control primers showed strong signals. The wild-type status of KIT in these 64 samples was determined by denaturing HPLC screening; 31 of the samples were also shown to be wild-type for KIT by direct sequencing. Because 20 of the samples were derived from cell lines (n=3) or fresh-frozen tumor tissue (6 AML, 3 GIST, 7 myxoid chondrosarcoma, 1 lymphoma), the quality of the DNA was not a factor in these AS-PCR reactions. The remaining 44 samples were from paraffin-embedded tumors (GIST, non-GIST sarcoma, hemangioma, thymic carcinoma, renal cell carcinoma, renal oncocytoma, fibromatosis) that carry wild type KIT exon 17. Genomic DNA from a cell line wild-type for KIT exon 17 (LoVo cells) was included as a negative control in all subsequent reactions.

Figure 18:
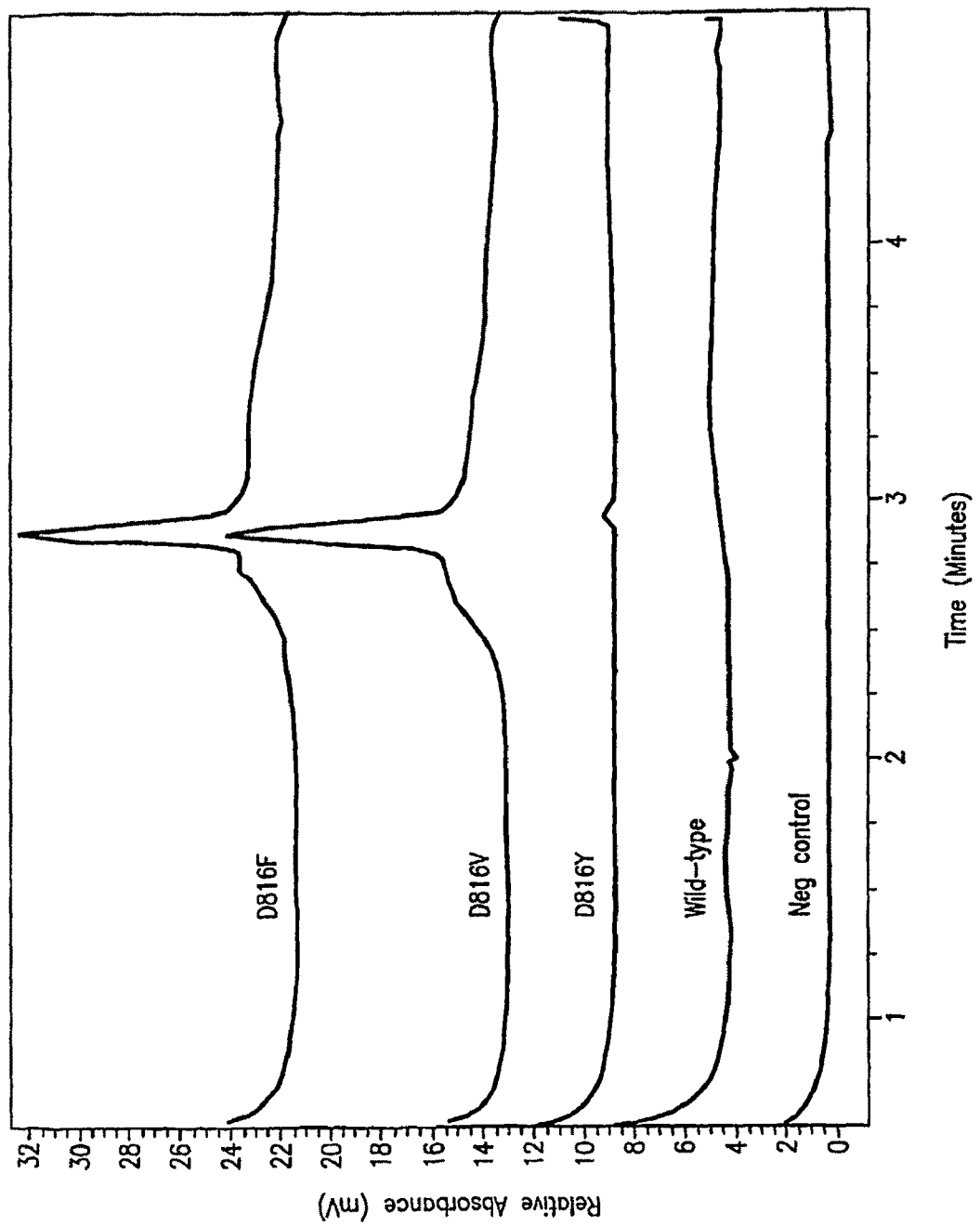
FIG. 18 shows results from AS-PCR of wild-type and mutant KIT cDNAs. cDNA prepared from stably transfected Ba/F3 subclones expressing various isoforms of KIT cDNA was tested by AS-PCR. Positive AS-PCR signals (minimum 2 mV) were obtained from cells expressing D816V or D816F cDNA, but not from cells transfected the wild-type or D816Y forms of KIT.

A group of BaF3 subclones expressing various isoforms of KIT cDNA were also tested. As illustrated in FIG. 18, positive AS-PCR signals were obtained from cells stably transfected with D816V or D816F cDNA, but not from cells containing WT or D816Y forms of KIT. Control PCR reactions for KIT exon 17 sequences were positive in all cases. Because the amplification target in these cell lines was cDNA, a different reverse primer was used in the AS-PCR reactions. The results illustrate the specificity of the MSP/B-oligo combination for the D816V and D816F mutations.

A series of tumors known to be positive for D816V was analyzed with the AS-PCR assay. These included 8 samples of AML (DNA from fresh cells) and 3 samples of paraffin-embedded seminoma (FIG. 19, samples 1-11). AU of these samples yielded positive amplimers by AS-PCR. As noted above, we could not further validate the AS-PCR reaction for the D816F mutation because none of our tumor samples had this substitution.

D) Other Mutations

We next examined a group of tumors with alternate mutations of codon 816 using the AS-PCR assay. Two seminomas with D816H did not amplify any product by AS-PCR, as expected (FIG. 19, samples 12 & 13). D816H is also a mutation found in GISTs from patients with acquired resistance to imatinib, and two such tumors were negative by AS-PCR despite robust amplifications with the control primers (FIG. 19, samples 14 & 15). Imatinib-resistant GISTs with D816G or D816A were AS-PCR negative, as well (FIG. 19, samples 16 & 17, respectively).

Interestingly, 2 AML samples that harbored a D816Y mutation by standard PCR and sequencing turned up positive by AS-PCR (FIG. 19, samples 18 & 19). Topo subclones were prepared (Invitrogen) and sequenced from these amplification products and D816V-positive clones were detected at low levels (FIG. 19, 1 of 20 from case 18, 1 of 10 from case 19). These results are consistent with the estimated sensitivity of the AS-PCR assay and provide evidence that there is heterogeneity among KIT mutations that occur in AML. Mutation heterogeneity may account for the small positive AS-PCR signal observed in one of the imatinib-resistant GISTs that appeared to be D816H by direct sequencing (FIG. 19, sample 20).

Example 11

Screening of Biopsies from Patients

A group of biopsies from adult patients with suspected mast cell disease was screened for KIT exon 17 mutation using standard PCR reaction and HPLC, with confirmatory sequencing as necessary, and by AS-PCCR. Among 21 bone marrow samples (aspirates or cores), 6 were positive by both assays, 7 were positive by AS-PCR only, and the remaining 8 were negative by both assays (FIG. 20A-B). The tested marrows were predominantly referral samples from patients with suspected systemic mastocytosis. Marrow samples from a patient with mast cell leukemia (FIG. 20A-B, sample 29) and a patient with SM-AML (FIG. 20A-B, sample 30) were positive by both the standard and AS-PCR assays. In contrast, marrow samples from 3 patients with a clinical diagnosis of SM-MPD (FIG. 20A-B, samples 56-58) were all negative by both assays. Interestingly, one of these was found to be positive for a JAK2 D617F mutation.

Eight skin biopsies from patients with mast cell infiltrates were screened for KIT exon 17 mutations using standard PCR reaction and HPLC, with confirmatory sequencing as necessary, and by AS-PCR. Three were positive by both the standard assay and AS-PCR, another was AS-PCR positive only, and the remaining 4 were completely negative (FIG. 20A-B). As no attempt was made to microdissect the areas involved by mast cells, it is possible that the negative cases had too few mast cells to allow detection even by AS-PCR. Alternatively, the infiltrates may not have been related to a mutant KIT-driven neoplasia. Other examples of tissues that yielded positive AS-PCR results included 1 colon biopsy, 1 lymph node and 1 of 2 blood samples (FIG. 20A-B).

The results summarized in FIG. 20A-B demonstrate an excellent correlation between the standard PCR/HPLC assay and AS-PCR results, but with a clear advantage for the latter. Sequential biopsies from one particular patient are of interest in this regard. A colon biopsy from a 61 year old male (FIG. 20A-B, sample 32) was morphologically consistent with the clinical diagnosis of systemic mastocytosis, but was negative for an exon 17 mutation by the standard assay. The AS-PCR assay using this sample produced a clearly positive signal. The patient subsequently developed AML and a blood sample (FIG. 20A-B, sample 31) was positive using both the standard assay (D816V for sequencing) and the AS-PCR assay.

The entire disclosure of each document cited (including patents, patent applications, journal articles, abstracts, laboratory manuals, books, Genbank Accession numbers, SWISS-PROT Accession numbers, or other disclosures) in the Background of the Invention, Detailed Description, Brief Description of the Figures, and Examples is hereby incorporated herein by reference in their entirety. Further, the hard copy of the Sequence Listing submitted herewith, in addition to its corresponding Computer Readable Form, are incorporated herein by reference in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A method of treating an individual suffering from a mutant KIT kinase disorder comprising administering to the individual a therapeutically effective amount of 'N-(2-chloro-6-methylphenyl)-2-[[6-[4- (2-hydroxyethyl)-1-piperazinyl]-2-methyl-4-pyrimidinyl]amino]-5-thiazolecarboxamide, or a pharmaceutically acceptable salt or hydrate thereof, and a therapeutically effective amount of rapamycin, wherein administration of the 'N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof in combination with rapamycin results in synergistic inhibition of the mutant KIT kinase, wherein the mutant KIT kinase disorder is selected from the group consisting of mast cell disease, gastrointestinal stromal tumors, leukemia, and testicular seminorna, wherein said mutant KIT kinase comprises a mutation at amino acid residue 816 of KIT kinase (SEQ ID NO:2).

2. The method of claim 1, wherein said mutation at amino acid residue 816 of SEQ ID NO:2 is selected from the group consisting of D816Y, D816F, D816V and D816H.

3. The method according to claim 1, wherein the mutant KIT kinase disorder is selected from the group consisting of systemic mast cell disorders, mastocytosis, acute lymphocytic leukemia, acute lymphoblastic leukemia, acute myelogenous leukemia, chronic myelogenous leukemia, and promyelocytic leukemia.

4. The method according to claim 1, wherein said mutant KIT kinase is at least partially resistant to a first kinase inhibitor.

5. The method according to claim 4, wherein said first kinase inhibitor is a Bcr-Abl kinase inhibitor.

6. The method according to claim 4 or 5 wherein said first kinase inhibitor comprises imatinib.

7. The method according to claim 1, wherein said mutant KIT kinase is constitutively active.

8. The method according to claim 1, wherein said mutant KIT kinase comprises an imatinib-resistant KIT mutation.

9. The method according to claim 1, wherein said disorder is mastocytosis, gastrointestinal stromal tumor, acute myelogenous leukemia, or testicular seminoma.

10. The method according to claim 1, wherein the 'N-(2-chloro-6-methylphenyl)-2-[[6-[4-(2-hydroxyethyl)-1-piperazinyl]-2-methyl-4-pyriniidinyl]amino]-5-thiazolecarboxamide, or a pharmaceutically acceptable salt or hydrate thereof, and the rapamycin are administered simultaneously.

11. The method according to claim 10, wherein the 'N-(2-chloro-6-methylphenyl)-2-[[6-[4-(2-hydroxyethyl)-1-piperazinyl]-2-methyl-4-pyrimidirtyl]amino]-5-thiazolecarboxamide, or a pharmaceutically acceptable salt or hydrate thereof, and the rapamycin are formulated in a pharmaceutical composition.

12. The method according to claim 1, wherein the 'N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt or hydrate thereof, and the rapamycin are administered sequentially.

* * * * *

UNITED STATES PATENT AND TRADEMARK OFFICE
CERTIFICATE OF CORRECTION

PATENT NO. : 8,247,419 B2  
APPLICATION NO. : 11/921781  
DATED : August 21, 2012  
INVENTOR(S) : Francis Y. Lee et al.

Page 1 of 1

It is certified that error appears in the above-identified patent and that said Letters Patent is hereby corrected as shown below:

Title Page, Column 2, line 4, under Other Publications, delete "weisenthal", second occurrence and insert -- wiesenthal --, therefor.

Title Page, Column 2, line 28, under Other Publications, delete "Metacalf" and insert -- Metcalfe --, therefor.

In the Claims

Col. 55, Line 41, in Claim 1, delete "seminorna," and insert -- seminoma, --, therefor.

Col. 56, Line 29, in Claim 6, delete "5" and insert -- 5, --, therefor.

Col. 56, Line 40, in Claim 10, delete "4-pyriniidinyl]" and insert -- 4-pyrimidinyl] --, therefor.

Col. 56, Line 45, in Claim 11, delete "4-pyrimidirtyl]" and insert -- 4-pyrimidinyl] --, therefor.

Signed and Sealed this  
Eighth Day of January, 2013

David J. Kappos  
*Director of the United States Patent and Trademark Office*

SEQUENCE LISTING

```
<160> NUMBER OF SEQ ID NOS: 10

<210> SEQ ID NO 1
<211> LENGTH: 2931
<212> TYPE: DNA
<213> ORGANISM: Homo sapiens
<220> FEATURE:
<221> NAME/KEY: CDS
<222> LOCATION: (1)..(2928)

<400> SEQUENCE: 1 atg aga ggc gct cgc ggc gcc tgg gat ttt ctc tgc gtt ctg ctc cta      48
Met Arg Gly Ala Arg Gly Ala Trp Asp Phe Leu Cys Val Leu Leu Leu
1               5                   10                  15 ctg ctt cgc gtc cag aca ggc tct tct caa cca tct gtg agt cca ggg      96
Leu Leu Arg Val Gln Thr Gly Ser Ser Gln Pro Ser Val Ser Pro Gly
            20                  25                  30 gaa ccg tct cca cca tcc atc cat cca gga aaa tca gac tta ata gtc     144
Glu Pro Ser Pro Pro Ser Ile His Pro Gly Lys Ser Asp Leu Ile Val
        35                  40                  45 cgc gtg ggc gac gag att agg ctg tta tgc act gat ccg ggc ttt gtc     192
Arg Val Gly Asp Glu Ile Arg Leu Leu Cys Thr Asp Pro Gly Phe Val
    50                  55                  60 aaa tgg act ttt gag atc ctg gat gaa acg aat gag aat aag cag aat     240
Lys Trp Thr Phe Glu Ile Leu Asp Glu Thr Asn Glu Asn Lys Gln Asn
65                  70                  75                  80 gaa tgg atc acg gaa aag gca gaa gcc acc aac acc ggc aaa tac acg     288
Glu Trp Ile Thr Glu Lys Ala Glu Ala Thr Asn Thr Gly Lys Tyr Thr
                85                  90                  95 tgc acc aac aaa cac ggc tta agc aat tcc att tat gtg ttt gtt aga     336
Cys Thr Asn Lys His Gly Leu Ser Asn Ser Ile Tyr Val Phe Val Arg
            100                 105                 110 gat cct gcc aag ctt ttc ctt gtt gac cgc tcc ttg tat ggg aaa gaa     384
Asp Pro Ala Lys Leu Phe Leu Val Asp Arg Ser Leu Tyr Gly Lys Glu
        115                 120                 125
```

-continued

| | |
|---|---|
| gac aac gac acg ctg gtc cgc tgt cct ctc aca gac cca gaa gtg acc<br>Asp Asn Asp Thr Leu Val Arg Cys Pro Leu Thr Asp Pro Glu Val Thr<br>130                         135                   140 | 432 |
| aat tat tcc ctc aag ggg tgc cag ggg aag cct ctt ccc aag gac ttg<br>Asn Tyr Ser Leu Lys Gly Cys Gln Gly Lys Pro Leu Pro Lys Asp Leu<br>145                       150                   155                 160 | 480 |
| agg ttt att cct gac ccc aag gcg ggc atc atg atc aaa agt gtg aaa<br>Arg Phe Ile Pro Asp Pro Lys Ala Gly Ile Met Ile Lys Ser Val Lys<br>                 165                 170                 175 | 528 |
| cgc gcc tac cat cgg ctc tgt ctg cat tgt tct gtg gac cag gag ggc<br>Arg Ala Tyr His Arg Leu Cys Leu His Cys Ser Val Asp Gln Glu Gly<br>                 180                 185                 190 | 576 |
| aag tca gtg ctg tcg gaa aaa ttc atc ctg aaa gtg agg cca gcc ttc<br>Lys Ser Val Leu Ser Glu Lys Phe Ile Leu Lys Val Arg Pro Ala Phe<br>195                       200                   205 | 624 |
| aaa gct gtg cct gtt gtg tct gtg tcc aaa gca agc tat ctt ctt agg<br>Lys Ala Val Pro Val Val Ser Val Ser Lys Ala Ser Tyr Leu Leu Arg<br>210                       215                   220 | 672 |
| gaa ggg gaa gaa ttc aca gtg acg tgc aca ata aaa gat gtg tct agt<br>Glu Gly Glu Glu Phe Thr Val Thr Cys Thr Ile Lys Asp Val Ser Ser<br>225                         230                   235                 240 | 720 |
| tct gtg tac tca acg tgg aaa aga gaa aac agt cag act aaa cta cag<br>Ser Val Tyr Ser Thr Trp Lys Arg Glu Asn Ser Gln Thr Lys Leu Gln<br>                 245                 250                 255 | 768 |
| gag aaa tat aat agc tgg cat cac ggt gac ttc aat tat gaa cgt cag<br>Glu Lys Tyr Asn Ser Trp His His Gly Asp Phe Asn Tyr Glu Arg Gln<br>260                       265                   270 | 816 |
| gca acg ttg act atc agt tca gcg aga gtt aat gat tct gga gtg ttc<br>Ala Thr Leu Thr Ile Ser Ser Ala Arg Val Asn Asp Ser Gly Val Phe<br>                 275                 280                 285 | 864 |
| atg tgt tat gcc aat aat act ttt gga tca gca aat gtc aca aca acc<br>Met Cys Tyr Ala Asn Asn Thr Phe Gly Ser Ala Asn Val Thr Thr Thr<br>290                       295                   300 | 912 |
| ttg gaa gta gta gat aaa gga ttc att aat atc ttc ccc atg ata aac<br>Leu Glu Val Val Asp Lys Gly Phe Ile Asn Ile Phe Pro Met Ile Asn<br>305                         310                   315                 320 | 960 |
| act aca gta ttt gta aac gat gga gaa aat gta gat ttg att gtt gaa<br>Thr Thr Val Phe Val Asn Asp Gly Glu Asn Val Asp Leu Ile Val Glu<br>                 325                 330                 335 | 1008 |
| tat gaa gca ttc ccc aaa cct gaa cac cag cag tgg atc tat atg aac<br>Tyr Glu Ala Phe Pro Lys Pro Glu His Gln Gln Trp Ile Tyr Met Asn<br>                 340                 345                 350 | 1056 |
| aga acc ttc act gat aaa tgg gaa gat tat ccc aag tct gag aat gaa<br>Arg Thr Phe Thr Asp Lys Trp Glu Asp Tyr Pro Lys Ser Glu Asn Glu<br>                 355                 360                 365 | 1104 |
| agt aat atc aga tac gta agt gaa ctt cat cta acg aga tta aaa ggc<br>Ser Asn Ile Arg Tyr Val Ser Glu Leu His Leu Thr Arg Leu Lys Gly<br>370                       375                   380 | 1152 |
| acc gaa gga ggc act tac aca ttc cta gtg tcc aat tct gac gtc aat<br>Thr Glu Gly Gly Thr Tyr Thr Phe Leu Val Ser Asn Ser Asp Val Asn<br>385                       390                   395                 400 | 1200 |
| gct gcc ata gca ttt aat gtt tat gtg aat aca aaa cca gaa atc ctg<br>Ala Ala Ile Ala Phe Asn Val Tyr Val Asn Thr Lys Pro Glu Ile Leu<br>                 405                 410                 415 | 1248 |
| act tac gac agg ctc gtg aat ggc atg ctc caa tgt gtg gca gca gga<br>Thr Tyr Asp Arg Leu Val Asn Gly Met Leu Gln Cys Val Ala Ala Gly<br>                 420                 425                 430 | 1296 |
| ttc cca gag ccc aca ata gat tgg tat ttt tgt cca gga act gag cag<br>Phe Pro Glu Pro Thr Ile Asp Trp Tyr Phe Cys Pro Gly Thr Glu Gln<br>435                       440                   445 | 1344 |

```
aga tgc tct gct tct gta ctg cca gtg gat gtg cag aca cta aac tca      1392
Arg Cys Ser Ala Ser Val Leu Pro Val Asp Val Gln Thr Leu Asn Ser
    450             455                 460 tct ggg cca ccg ttt gga aag cta gtg gtt cag agt tct ata gat tct      1440
Ser Gly Pro Pro Phe Gly Lys Leu Val Val Gln Ser Ser Ile Asp Ser
465             470                 475                 480 agt gca ttc aag cac aat ggc acg gtt gaa tgt aag gct tac aac gat      1488
Ser Ala Phe Lys His Asn Gly Thr Val Glu Cys Lys Ala Tyr Asn Asp
                    485                 490                 495 gtg ggc aag act tct gcc tat ttt aac ttt gca ttt aaa ggt aac aac      1536
Val Gly Lys Thr Ser Ala Tyr Phe Asn Phe Ala Phe Lys Gly Asn Asn
                500                 505                 510 aaa gag caa atc cat ccc cac acc ctg ttc act cct ttg ctg att ggt      1584
Lys Glu Gln Ile His Pro His Thr Leu Phe Thr Pro Leu Leu Ile Gly
            515                 520                 525 ttc gta atc gta gct ggc atg atg tgc att att gtg atg att ctg acc      1632
Phe Val Ile Val Ala Gly Met Met Cys Ile Ile Val Met Ile Leu Thr
        530                 535                 540 tac aaa tat tta cag aaa ccc atg tat gaa gta cag tgg aag gtt gtt      1680
Tyr Lys Tyr Leu Gln Lys Pro Met Tyr Glu Val Gln Trp Lys Val Val
545             550                 555                 560 gag gag ata aat gga aac aat tat gtt tac ata gac cca aca caa ctt      1728
Glu Glu Ile Asn Gly Asn Asn Tyr Val Tyr Ile Asp Pro Thr Gln Leu
                565                 570                 575 cct tat gat cac aaa tgg gag ttt ccc aga aac agg ctg agt ttt ggg      1776
Pro Tyr Asp His Lys Trp Glu Phe Pro Arg Asn Arg Leu Ser Phe Gly
                    580                 585                 590 aaa acc ctg ggt gct gga gct ttc ggg aag gtt gtt gag gca act gct      1824
Lys Thr Leu Gly Ala Gly Ala Phe Gly Lys Val Val Glu Ala Thr Ala
                595                 600                 605 tat ggc tta att aag tca gat gcg gcc atg act gtc gct gta aag atg      1872
Tyr Gly Leu Ile Lys Ser Asp Ala Ala Met Thr Val Ala Val Lys Met
            610                 615                 620 ctc aag ccg agt gcc cat ttg aca gaa cgg gaa gcc ctc atg tct gaa      1920
Leu Lys Pro Ser Ala His Leu Thr Glu Arg Glu Ala Leu Met Ser Glu
625             630                 635                 640 ctc aaa gtc ctg agt tac ctt ggt aat cac atg aat att gtg aat cta      1968
Leu Lys Val Leu Ser Tyr Leu Gly Asn His Met Asn Ile Val Asn Leu
                645                 650                 655 ctt gga gcc tgc acc att gga ggg ccc acc ctg gtc att aca gaa tat      2016
Leu Gly Ala Cys Thr Ile Gly Gly Pro Thr Leu Val Ile Thr Glu Tyr
                    660                 665                 670 tgt tgc tat ggt gat ctt ttg aat ttt ttg aga aga aaa cgt gat tca      2064
Cys Cys Tyr Gly Asp Leu Leu Asn Phe Leu Arg Arg Lys Arg Asp Ser
                675                 680                 685 ttt att tgt tca aag cag gaa gat cat gca gaa gct gca ctt tat aag      2112
Phe Ile Cys Ser Lys Gln Glu Asp His Ala Glu Ala Ala Leu Tyr Lys
            690                 695                 700 aat ctt ctg cat tca aag gag tct tcc tgc agc gat agt act aat gag      2160
Asn Leu Leu His Ser Lys Glu Ser Ser Cys Ser Asp Ser Thr Asn Glu
705             710                 715                 720 tac atg gac atg aaa cct gga gtt tct tat gtt gtc cca acc aag gcc      2208
Tyr Met Asp Met Lys Pro Gly Val Ser Tyr Val Val Pro Thr Lys Ala
                725                 730                 735 gac aaa agg aga tct gtg aga ata ggc tca tac ata gaa aga gat gtg      2256
Asp Lys Arg Arg Ser Val Arg Ile Gly Ser Tyr Ile Glu Arg Asp Val
                740                 745                 750 act ccc gcc atc atg gag gat gac gag ttg gcc cta gac tta gaa gac      2304
Thr Pro Ala Ile Met Glu Asp Asp Glu Leu Ala Leu Asp Leu Glu Asp
            755                 760                 765
```

| | | | | | | | | | | | | | | | |
|---|---|---|---|---|---|---|---|---|---|---|---|---|---|---|---|
| ttg | ctg | agc | ttt | tct | tac | cag | gtg | gca | aag | ggc | atg | gct | ttc | ctc | gcc | 2352 |
| Leu | Leu | Ser | Phe | Ser | Tyr | Gln | Val | Ala | Lys | Gly | Met | Ala | Phe | Leu | Ala | |
| | 770 | | | | 775 | | | | | 780 | | | | | | | tcc aag aat tgt att cac aga gac ttg gca gcc aga aat atc ctc ctt 2400
Ser Lys Asn Cys Ile His Arg Asp Leu Ala Ala Arg Asn Ile Leu Leu
785                 790                 795                 800 act cat ggt cgg atc aca aag att tgt gat ttt ggt cta gcc aga gac 2448
Thr His Gly Arg Ile Thr Lys Ile Cys Asp Phe Gly Leu Ala Arg Asp
                    805                 810                 815 atc aag aat gat tct aat tat gtg gtt aaa gga aac gct cga cta cct 2496
Ile Lys Asn Asp Ser Asn Tyr Val Val Lys Gly Asn Ala Arg Leu Pro
            820                 825                 830 gtg aag tgg atg gca cct gaa agc att ttc aac tgt gta tac acg ttt 2544
Val Lys Trp Met Ala Pro Glu Ser Ile Phe Asn Cys Val Tyr Thr Phe
        835                 840                 845 gaa agt gac gtc tgg tcc tat ggg att ttt ctt tgg gag ctg ttc tct 2592
Glu Ser Asp Val Trp Ser Tyr Gly Ile Phe Leu Trp Glu Leu Phe Ser
850                 855                 860 tta gga agc agc ccc tat cct gga atg ccg gtc gat tct aag ttc tac 2640
Leu Gly Ser Ser Pro Tyr Pro Gly Met Pro Val Asp Ser Lys Phe Tyr
865                 870                 875                 880 aag atg atc aag gaa ggc ttc cgg atg ctc agc cct gaa cac gca cct 2688
Lys Met Ile Lys Glu Gly Phe Arg Met Leu Ser Pro Glu His Ala Pro
                    885                 890                 895 gct gaa atg tat gac ata atg aag act tgc tgg gat gca gat ccc cta 2736
Ala Glu Met Tyr Asp Ile Met Lys Thr Cys Trp Asp Ala Asp Pro Leu
            900                 905                 910 aaa aga cca aca ttc aag caa att gtt cag cta att gag aag cag att 2784
Lys Arg Pro Thr Phe Lys Gln Ile Val Gln Leu Ile Glu Lys Gln Ile
        915                 920                 925 tca gag agc acc aat cat att tac tcc aac tta gca aac tgc agc ccc 2832
Ser Glu Ser Thr Asn His Ile Tyr Ser Asn Leu Ala Asn Cys Ser Pro
930                 935                 940 aac cga cag aag ccc gtg gta gac cat tct gtg cgg atc aat tct gtc 2880
Asn Arg Gln Lys Pro Val Val Asp His Ser Val Arg Ile Asn Ser Val
945                 950                 955                 960 ggc agc acc gct tcc tcc tcc cag cct ctg ctt gtg cac gac gat gtc 2928
Gly Ser Thr Ala Ser Ser Ser Gln Pro Leu Leu Val His Asp Asp Val
                    965                 970                 975 tga 2931

<210> SEQ ID NO 2
<211> LENGTH: 976
<212> TYPE: PRT
<213> ORGANISM: Homo sapiens

<400> SEQUENCE: 2

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

-continued

```
Cys Thr Asn Lys His Gly Leu Ser Asn Ser Ile Tyr Val Phe Val Arg
                100                 105                 110
Asp Pro Ala Lys Leu Phe Leu Val Asp Arg Ser Leu Tyr Gly Lys Glu
            115                 120                 125
Asp Asn Asp Thr Leu Val Arg Cys Pro Leu Thr Asp Pro Glu Val Thr
130                 135                 140
Asn Tyr Ser Leu Lys Gly Cys Gln Gly Lys Pro Leu Pro Lys Asp Leu
145                 150                 155                 160
Arg Phe Ile Pro Asp Pro Lys Ala Gly Ile Met Ile Lys Ser Val Lys
                165                 170                 175
Arg Ala Tyr His Arg Leu Cys Leu His Cys Ser Val Asp Gln Glu Gly
            180                 185                 190
Lys Ser Val Leu Ser Glu Lys Phe Ile Leu Lys Val Arg Pro Ala Phe
        195                 200                 205
Lys Ala Val Pro Val Val Ser Val Ser Lys Ala Ser Tyr Leu Leu Arg
210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                245                 250                 255
Glu Lys Tyr Asn Ser Trp His His Gly Asp Phe Asn Tyr Glu Arg Gln
            260                 265                 270
Ala Thr Leu Thr Ile Ser Ser Ala Arg Val Asn Asp Ser Gly Val Phe
        275                 280                 285
Met Cys Tyr Ala Asn Asn Thr Phe Gly Ser Ala Asn Val Thr Thr Thr
            290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
            340                 345                 350
Arg Thr Phe Thr Asp Lys Trp Glu Asp Tyr Pro Lys Ser Glu Asn Glu
        355                 360                 365
Ser Asn Ile Arg Tyr Val Ser Glu Leu His Leu Thr Arg Leu Lys Gly
370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
            420                 425                 430
Phe Pro Glu Pro Thr Ile Asp Trp Tyr Phe Cys Pro Gly Thr Glu Gln
        435                 440                 445
Arg Cys Ser Ala Ser Val Leu Pro Val Asp Val Gln Thr Leu Asn Ser
        450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Gly Asn Asn
            500                 505                 510
Lys Glu Gln Ile His Pro His Thr Leu Phe Thr Pro Leu Leu Ile Gly
        515                 520                 525
```

-continued

Phe Val Ile Val Ala Gly Met Met Cys Ile Ile Val Met Ile Leu Thr
530                     535                     540

Tyr Lys Tyr Leu Gln Lys Pro Met Tyr Glu Val Gln Trp Lys Val Val
545                     550                     555                     560

Glu Glu Ile Asn Gly Asn Asn Tyr Val Tyr Ile Asp Pro Thr Gln Leu
                565                     570                     575

Pro Tyr Asp His Lys Trp Glu Phe Pro Arg Asn Arg Leu Ser Phe Gly
                580                     585                     590

Lys Thr Leu Gly Ala Gly Ala Phe Gly Lys Val Val Glu Ala Thr Ala
        595                     600                     605

Tyr Gly Leu Ile Lys Ser Asp Ala Ala Met Thr Val Ala Val Lys Met
610                     615                     620

Leu Lys Pro Ser Ala His Leu Thr Glu Arg Glu Ala Leu Met Ser Glu
625                     630                     635                     640

Leu Lys Val Leu Ser Tyr Leu Gly Asn His Met Asn Ile Val Asn Leu
                645                     650                     655

Leu Gly Ala Cys Thr Ile Gly Gly Pro Thr Leu Val Ile Thr Glu Tyr
                660                     665                     670

Cys Cys Tyr Gly Asp Leu Leu Asn Phe Leu Arg Arg Lys Arg Asp Ser
        675                     680                     685

Phe Ile Cys Ser Lys Gln Glu Asp His Ala Glu Ala Ala Leu Tyr Lys
690                     695                     700

Asn Leu Leu His Ser Lys Glu Ser Ser Cys Ser Asp Ser Thr Asn Glu
705                     710                     715                     720

Tyr Met Asp Met Lys Pro Gly Val Ser Tyr Val Val Pro Thr Lys Ala
                725                     730                     735

Asp Lys Arg Arg Ser Val Arg Ile Gly Ser Tyr Ile Glu Arg Asp Val
                740                     745                     750

Thr Pro Ala Ile Met Glu Asp Asp Glu Leu Ala Leu Asp Leu Glu Asp
        755                     760                     765

Leu Leu Ser Phe Ser Tyr Gln Val Ala Lys Gly Met Ala Phe Leu Ala
770                     775                     780

Ser Lys Asn Cys Ile His Arg Asp Leu Ala Ala Arg Asn Ile Leu Leu
785                     790                     795                     800

Thr His Gly Arg Ile Thr Lys Ile Cys Asp Phe Gly Leu Ala Arg Asp
                805                     810                     815

Ile Lys Asn Asp Ser Asn Tyr Val Val Lys Gly Asn Ala Arg Leu Pro
                820                     825                     830

Val Lys Trp Met Ala Pro Glu Ser Ile Phe Asn Cys Val Tyr Thr Phe
        835                     840                     845

Glu Ser Asp Val Trp Ser Tyr Gly Ile Phe Leu Trp Glu Leu Phe Ser
850                     855                     860

Leu Gly Ser Ser Pro Tyr Pro Gly Met Pro Val Asp Ser Lys Phe Tyr
865                     870                     875                     880

Lys Met Ile Lys Glu Gly Phe Arg Met Leu Ser Pro Glu His Ala Pro
                885                     890                     895

Ala Glu Met Tyr Asp Ile Met Lys Thr Cys Trp Asp Ala Asp Pro Leu
                900                     905                     910

Lys Arg Pro Thr Phe Lys Gln Ile Val Gln Leu Ile Glu Lys Gln Ile
        915                     920                     925

Ser Glu Ser Thr Asn His Ile Tyr Ser Asn Leu Ala Asn Cys Ser Pro
930                     935                     940

```
Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 3
<211> LENGTH: 20
<212> TYPE: DNA
<213> ORGANISM: Artificial
<220> FEATURE:
<223> OTHER INFORMATION: Forward primer

<400> SEQUENCE: 3
tgtattcaca gagacttggc                                                        20

<210> SEQ ID NO 4
<211> LENGTH: 22
<212> TYPE: DNA
<213> ORGANISM: Artificial
<220> FEATURE:
<223> OTHER INFORMATION: Reverse primer

<400> SEQUENCE: 4
taatgttcag cataccatgc aa                                                     22

<210> SEQ ID NO 5
<211> LENGTH: 24
<212> TYPE: DNA
<213> ORGANISM: Artificial
<220> FEATURE:
<223> OTHER INFORMATION: Reverse primer

<400> SEQUENCE: 5
gctcccaaag aaaaatccca tagg                                                   24

<210> SEQ ID NO 6
<211> LENGTH: 22
<212> TYPE: DNA
<213> ORGANISM: Artificial
<220> FEATURE:
<223> OTHER INFORMATION: Primer sequence

<400> SEQUENCE: 6
gtgattttgg tctagccaga at                                                     22

<210> SEQ ID NO 7
<211> LENGTH: 22
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (22)..(22)
<223> OTHER INFORMATION: n is A (adenine) linked in a chemically
      reversed configuration (3' to 5')

<400> SEQUENCE: 7
gtgattttgg tctagccaga an                                                     22

<210> SEQ ID NO 8
<211> LENGTH: 22
<212> TYPE: DNA
<213> ORGANISM: Artificial
<220> FEATURE:
<223> OTHER INFORMATION: D816V Mutant sequence
```

```
<400> SEQUENCE: 8
cactaaaacc agatcggtct ca                                              22

<210> SEQ ID NO 9
<211> LENGTH: 22
<212> TYPE: DNA
<213> ORGANISM: Artificial
<220> FEATURE:
<223> OTHER INFORMATION: D816F Mutant sequence

<400> SEQUENCE: 9
cactaaaacc agatcggtct aa                                              22

<210> SEQ ID NO 10
<211> LENGTH: 22
<212> TYPE: DNA
<213> ORGANISM: Artificial
<220> FEATURE:
<223> OTHER INFORMATION: Wild-type sequence

<400> SEQUENCE: 10
gtgattttgg tctagccaga ct                                              22
```